(12) United States Patent
Finkelstein et al.

(10) Patent No.: US 7,541,377 B2
(45) Date of Patent: Jun. 2, 2009

(54) SUBSTITUTED ANTHRANILAMIDES FOR CONTROLLING INVERTEBRATE PESTS

(75) Inventors: Bruce Lawrence Finkelstein, Newark, DE (US); George Philip Lahm, Wilmington, DE (US); Stephen Frederick McCann, Newark, DE (US); Thomas Paul Selby, Hockessin, DE (US); Ying Song, Hockessin, DE (US); Thomas Martin Stevenson, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/700,584

(22) Filed: Jan. 31, 2007

(65) Prior Publication Data

US 2007/0203201 A1 Aug. 30, 2007

Related U.S. Application Data

(62) Division of application No. 10/486,312, filed as application No. PCT/US02/26960 on Aug. 13, 2002, now Pat. No. 7,199,138.

(60) Provisional application No. 60/312,680, filed on Aug. 16, 2001.

(51) Int. Cl.
A01N 43/56 (2006.01)
C07D 231/12 (2006.01)
C07D 231/34 (2006.01)

(52) U.S. Cl. .................. 514/406; 514/407; 548/369.7; 548/375.1

(58) Field of Classification Search ............ 548/369.7, 548/375.1; 514/406, 407
See application file for complete search history.

(56) References Cited

U.S. PATENT DOCUMENTS

| 4,321,371 | A | 3/1982 | Parg et al. |
|---|---|---|---|
| 4,814,001 | A | 3/1989 | Stetter et al. |
| 5,082,949 | A | 1/1992 | Sohn et al. |
| 5,523,280 | A | 6/1996 | Chene et al. |
| 5,602,126 | A | 2/1997 | Barnette et al. |
| 5,728,693 | A | 3/1998 | Stevenson |
| 5,998,424 | A | 12/1999 | Galemmo, Jr. et al. |
| 6,020,357 | A | 2/2000 | Pinto et al. |
| 6,242,475 | B1 | 6/2001 | Huang et al. |
| 6,258,751 | B1 | 7/2001 | Jacobson et al. |
| 6,403,620 | B1 | 6/2002 | Galemmo, Jr. et al. |
| 6,444,613 | B1 | 9/2002 | Feurer et al. |
| 6,548,512 | B1 | 4/2003 | Pinto et al. |
| 6,602,895 | B2 | 8/2003 | Galemmo, Jr. et al. |
| 6,747,047 | B2 | 6/2004 | Lahm et al. |
| 2004/0102324 | A1 | 5/2004 | Annis et al. |
| 2004/0110777 | A1 | 6/2004 | Annis et al. |
| 2004/0138450 | A1 | 7/2004 | Clark |
| 2004/0142984 | A1 | 7/2004 | Lahm et al. |

(Continued)

FOREIGN PATENT DOCUMENTS

| DE | 4428380 A | 8/1994 |
|---|---|---|
| DE | 19840322 A1 | 9/1998 |
| EP | 0289879 A | 11/1986 |
| EP | 0919542 A2 | 6/1999 |
| EP | 0 946 508 A1 | 10/1999 |
| EP | 1198254 A1 | 1/2001 |
| EP | 0 991 625 B1 | 6/2005 |
| JP | 2-129171 | 5/1990 |
| JP | 6-25177 | 2/1994 |
| NL | 9202078 A | 11/1992 |
| WO | WO 96/38419 | 12/1996 |
| WO | WO 97/47589 A | 12/1997 |
| WO | WO98/28269 | 7/1998 |
| WO | WO98/57937 | 12/1998 |
| WO | WO 01/02354 A1 | 1/2001 |
| WO | WO 01/22821 A1 | 4/2001 |
| WO | WO 01/32628 A1 | 5/2001 |
| WO | WO 01/70671 A | 9/2001 |
| WO | WO 03/106427 | 12/2003 |
| WO | WO 2004/011447 | 2/2004 |
| WO | WO 2004/011453 | 2/2004 |
| WO | WO 2004/033468 | 4/2004 |
| WO | WO 2004/046129 | 6/2004 |
| WO | WO 2004/067528 | 6/2004 |

OTHER PUBLICATIONS

XP002177117 Suto, Mark J. et al.: Tetrahedron Letters, vol. 36, No. 40, 1995, pp. 7213-7216, Elsevier Science Publishers, Amsterdam, NL.
Klaubert et al., J.Med.Chem., vol. 24, No. 6, pp. 748-752, 1981.

Primary Examiner—Patricia L Morris

(57) ABSTRACT

This invention provides compounds of Formula I, and N-oxides and salts thereof

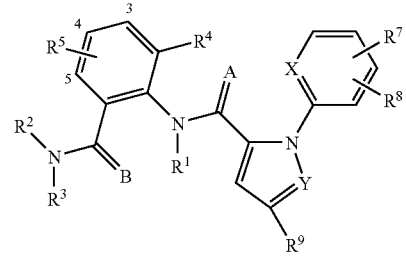

wherein A, B, $R^1$ through $R^5$, $R^7$ through $R^9$, X and Y are as defined in the disclosure.

Also disclosed are methods for controlling an invertebrate pest comprising contacting the invertebrate pest or its environment with a biologically effective amount of a compound of Formula I. Also disclosed are compositions for controlling an invertebrate pest comprising the compounds of Formula I.

17 Claims, No Drawings

U.S. PATENT DOCUMENTS

| | | |
|---|---|---|
| 2004/0171649 A1 | 9/2004 | Annis et al. |
| 2004/0192731 A1 | 9/2004 | Finkelstein et al. |
| 2004/0198984 A1 | 10/2004 | Lahm et al. |
| 2004/0198987 A1 | 10/2004 | Freudenberger et al. |
| 2004/0209923 A1 | 10/2004 | Berger et al. |
| 2004/0259913 A1 | 12/2004 | Clark |
| 2005/0075372 A1 | 4/2005 | Lahm et al. |
| 2005/0124600 A1 | 6/2005 | Clark et al. |
| 2005/0147633 A1 | 7/2005 | Stevenson |

SUBSTITUTED ANTHRANILAMIDES FOR CONTROLLING INVERTEBRATE PESTS

BACKGROUND OF THE INVENTION

This invention relates to certain substituted anthranilamides, their N-oxides, salts and compositions suitable for agronomic and nonagronomic uses, including those uses listed below, and a method of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides

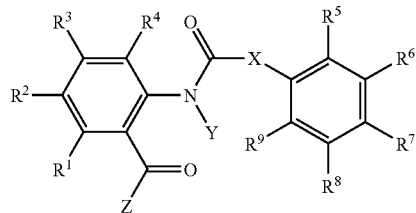

wherein, inter alia, X is a direct bond; Y is H or $C_1$-$C_6$ alkyl; Z is $NH_2$, $NH(C_1$-$C_3$ alkyl) or $N(C_1$-$C_3$ alkyl)$_2$; and $R^1$ through $R^9$ are independently H, halogen, $C_1$-$C_6$ alkyl, phenyl, hydroxy, $C_1$-$C_6$ alkoxy or $C_1$-$C_7$ acyloxy.

SUMMARY OF THE INVENTION

This invention pertains to compounds of Formula I, and N-oxides and salts thereof,

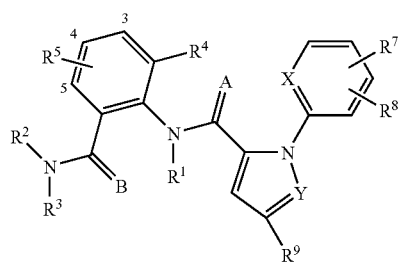

wherein

A and B are independently O or S;
X is N or $CR^{10}$;
Y is N or CH;
$R^1$ is H; $R^{11}$; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of $R^6$, halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $(C_1$-$C_4$ alkyl)$C_3$-$C_6$ cycloalkylamino and $R^{11}$;

$R^2$ is H, $C_1$-$C_6$ alkyl $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $(C_1$-$C_4$ alkyl)$C_3$-$C_6$ cycloalkylamino, $C_2$-$C_6$ alkoxycarbonyl or $C_2$-$C_6$ alkylcarbonyl;

$R^3$ is H; $R^{11}$; or $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of $R^6$, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_3$-$C_6$ trialkylsilyl, $R^{11}$, a phenyl, a phenoxy and 5- or 6-membered heteroaromatic rings, each phenyl, phenoxy and 5- or 6-membered heteroaromatic ring optionally substituted with from one to three substituents independently selected from W and optionally substituted with one $R^{12}$; or $R^2$ and $R^3$ can be taken together with the nitrogen to which they are attached to form K;

$R^4$ is $C_1$-$C_4$ alkyl, $C_1$-$C_4$ haloalkyl, CN, halogen, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl;

$R^5$ and $R^8$ are each independently H; $C_1$-$C_4$ alkyl; $C_1$-$C_4$ haloalkyl; halogen; $R^{12}$; G; J; O-J; O-G; $S(O)_p$-J; $S(O)_p$-G; $S(O)_p$-phenyl optionally substituted with one to three substituents independently selected from W and optionally substituted with one $R^{12}$; $C_1$-$C_{10}$ alkyl, $C_2$-$C_6$ alkenyl, $C_2$-$C_6$ alkynyl, $C_1$-$C_4$ alkoxy or $C_1$-$C_4$ alkythio, each substituted with one or more substituents selected from the group consisting of G, J, $R^6$, halogen, CN, $NO_2$, $NH_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ trialkylsilyl, a phenyl ring and a phenoxy ring, each phenyl and phenoxy ring optionally substituted with from one to three substituents independently selected from W and optionally substituted with one $R^{12}$;

each G is independently a 5- or 6-membered nonaromatic heterocyclic ring, optionally including one or two ling members selected from the group consisting of C(=O), SO or $S(O)_2$ and optionally substituted with from one to four substituents selected from the group consisting of $C_1$-$C_2$ alkyl, halogen, CN, $NO_2$ and $C_1$-$C_2$ alkoxy; or each G is independently $C_2$-$C_6$ alkenyl, $C_2$-$C_6$ alkynyl, $C_3$-$C_7$ cycloalkyl, (cyano)$C_3$-$C_7$ cycloalkyl, $(C_1$-$C_4$ alkyl)$C_3$-$C_6$ cycloalkyl, $(C_3$-$C_6$ cycloalkyl)$C_1$-$C_4$ alkyl, each cycloalkyl, (alkyl)cycloalkyl and (cycloalkyl)alkyl optionally substituted with one or more halogen;

each J is independently a 5- or 6-membered heteroaromatic ring optionally substituted with one to three substituents independently selected from W and optionally substituted with $R^{12}$;

each $R^6$ is independently $R^{19}C(=E)$-; $R^{19}C(=E)L$-; $R^{19}LC(=E)$-; $(R^{19})LC(=E)L$-; $-O(Q=)P(OR^{19})_2$; $-SO_2LR^{18}$; or $R^{19}SO_2L$-;

each E is independently O, S, $NR^{15}$, $NOR^{15}$, $NN(R^{15})_2$, N—S=O, N—CN or N—$NO_2$;

$R^7$ is H, $C_1$-$C_4$ alkyl, $C_1$-$C_4$ haloalkyl, halogen, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl;

$R^9$ is $CF_3$, $OCF_3$, $OCHF_2$, $OCH_2CF_3$, $S(O)_pCF_3$, $S(O)_pCHF_2$ or halogen;

$R^{10}$ is H, $C_1$-$C_4$ alkyl, $C_1$-$C_4$ haloalkyl, halogen, CN or $C_1$-$C_4$ haloalkoxy;

each $R^{11}$ is independently $C_1$-$C_6$ alkylthio; $C_1$-$C_6$ alkylsulfenyl; $C_1$-$C_6$ haloalkythio; $C_1$-$C_6$ haloalkylsulfenyl; phenylthio or phenylsulfenyl each optionally substituted with from one to three substituents independently selected from W; $(R^{16})_2NS(O)_n$—; $R^{13}C(=O)$—; $R^{14}C(=O)L$-; $R^{14}LC(=O)S$—; $R^{13}LC(=O)$—; $R^{13}C(=O)NR^{13}S(O)_2$—; $R^{14}LC(=O)NR^{13}S(O)_n$— or $R^{14}LSO_2NR^{13}S(O)_n$—;

each L is independently O, $NR^{18}$ or S;

each $R^{12}$ is independently $B(OR^{17})_2$; $NH_2$; SH; thiocyanato; $C_3$-$C_8$ trialkylsilyloxy; $C_1$-$C_4$ alkyldisulfide; $SF_5$; $R^{19}C(=E)$-; $R^{19}C(=E)L$-; $R^{19}LC(=E)$-; $(R^{19})LC(=E)L$-; —$OP(=Q)(OR^{19})_2$; —$SO_2LR^{19}$; $R^{19}SO_2L$-;

Q is O or S;

each $R^{13}$ is independently hydrogen; $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of $R^6$, halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino and $(C_1$-$C_4$ alkyl$)C_3$-$C_6$ cycloalkylamino;

each $R^{14}$ is $C_1$-$C_{20}$ alkyl, $C_2$-$C_{20}$ alkenyl, $C_2$-$C_{20}$ alkynyl or $C_3$-$C_6$ cycloalkyl each optionally substituted with one or more substituents selected from the group consisting of $R^6$, halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino and $(C_1$-$C_4$ alkyl$)C_3$-$C_6$ cycloalkylamino; or phenyl optionally substituted with from one to three substituents independently selected from W and optionally substituted with $R^{12}$;

each $R^{15}$ is independently H; $C_1$-$C_6$ haloalkyl; $C_1$-$C_6$ alkyl optionally substituted with one or more substituents selected from the group consisting of CN, $NO_2$, $R^6$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_2$-$C_6$ alkoxycarbonyl, $C_2$-$C_6$ alkylcarbonyl, $C_3$-$C_6$ trialkylsilyl, and a phenyl ring optionally substituted with one to three substituents independently selected from W and optionally substituted with one $R^{12}$; or phenyl optionally substituted with one to three substituents independently selected from W and optionally substituted with $R^{12}$; or $N(R^{15})_2$ can be taken together to form K;

$R^{16}$ is $C_1$-$C_{12}$ alkyl or $C_1$-$C_{12}$ haloalkyl; or $N(R^{16})_2$ can be taken together to form K;

each $R^{17}$ is independently H or $C_1$-$C_4$ alkyl; or $B(OR^{17})_2$ can form a ring wherein the two oxygen atoms are linked by a chain of two to three carbons optionally substituted with one or two substituents independently selected from methyl or $C_2$-$C_6$ alkoxycarbonyl;

each $R^{18}$ is independently H, $C_1$-$C_6$ alkyl or $C_1$-$C_6$ haloalkyl; or $N(R^{13})(R^{18})$ can be taken together to form K;

each $R^{19}$ is independently H; $C_1$-$C_6$ alkyl optionally substituted with one or more substituents selected from the group consisting of CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $CO_2H$, $C_2$-$C_6$ alkoxycarbonyl, $C_2$-$C_6$ alkylcarbonyl, $C_3$-$C_6$ trialkylsilyl, and a phenyl ring optionally substituted with one to three substituents independently selected from W; $C_1$-$C_6$ haloalkyl; $C_3$-$C_6$ cycloalkyl; or phenyl or pyridinyl optionally substituted with from one to three substituents independently selected from W;

each K is a ring containing, in addition to the nitrogen atom to which the substituent pair $R^{13}$ and $R^{18}$, $(R^{15})_2$ or $(R^{16})_2$ is attached, from 2 to 6 atoms of carbon and optionally one additional atom of nitrogen, sulfur or oxygen, said ring optionally substituted with from one to four substituents selected from the group consisting of $C_1$-$C_2$ alkyl, halogen, CN, $NO_2$ and $C_1$-$C_2$ alkoxy;

each W is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $(C_1$-$C_4$ alkyl$)C_3$-$C_6$ cycloalkylamino, $C_2$-$C_4$ alkylcarbonyl, $C_2$-$C_6$ alkoxycarbonyl, $CO_2H$, $C_2$-$C_6$ alkylaminocarbonyl, $C_3$-$C_8$ dialkylaminocarbonyl or $C_3$-$C_6$ trialkylsilyl;

each n is independently 0 or 1; and each p is independently 0, 1 or 2;

provided that when both (a) $R^5$ is H, $C_1$-$C_6$ alkyl, $C_1$-$C_6$ haloalkyl, $C_2$-$C_6$ haloalkenyl, $C_2$-$C_6$ haloalkynyl, $C_1$-$C_4$ haloalkoxy, $C_1$-$C_4$ haloalkylthio or halogen; and (b) $R^8$ is H, $C_1$-$C_6$ alkyl, $C_1$-$C_6$ haloalkyl, $C_2$-$C_6$ haloalkenyl, $C_2$-$C_6$ haloalkynyl, $C_1$-$C_4$ haloalkoxy, $C_1$-$C_4$ haloalkylthio, halogen, $C_2$-$C_4$ alkylcarbonyl, $C_2$-$C_6$ alkoxycarbonyl, $C_2$-$C_6$ alkylaminocarbonyl or $C_3$-$C_8$ dialkylaminocarbonyl; then both (c) at least one substituent selected from the group consisting of $R^6$, $R^{11}$ and $R^{12}$ is present; and (d) when $R^{12}$ is not present, at least one $R^6$ or $R^{11}$ is other than $C_2$-$C_6$ alkylcarbonyl, $C_2$-$C_6$ alkoxycarbonyl, $C_2$-$C_6$ alkylaminocarbonyl and $C_3$-$C_8$ dialkylaminocarbonyl.

This invention also pertains to a method for controlling an invertebrate pest comprising contacting the invertebrate pest or its environment with a biologically effective amount of a compound of Formula I, an N-oxide thereof or a salt thereof (e.g., as a composition described herein). This invention also relates to such a method wherein the invertebrate pest or its environment is contacted with a biologically effective amount of a compound of Formula I, an N-oxide thereof or a salt thereof, or a composition comprising the compound, N-oxide thereof or a salt thereof, and a biologically effective amount of at least one additional compound or agent for controlling an invertebrate pest.

This invention also pertains to a composition for controlling an invertebrate pest comprising a biologically effective amount of a compound of Formula I, an N-oxide thereof or a salt thereof and at least one additional component selected from the group consisting of surfactants, solid diluents and liquid diluents. This invention also pertains to a composition comprising a biologically effective amount of a compound of Formula I, an N-oxide thereof or a salt thereof and an effective amount of at least one additional biologically active compound or agent.

DETAILS OF THE INVENTION

In the above recitations, "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers.

"Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Cycloalkyl" includes, for example, cyclopropyl, cyclobutyl, cyclopentyl and cyclohexyl. Examples of "cycloalkylalkyl" include cyclopropylmethyl, cyclopentylethyl, and other cycloalkyl moieties bonded to straight-chain or branched alkyl groups. Examples of "alkylcycloalkyl" include methylcyclopropyl, dimethylcyclopropyl, ethylcyclopentyl, and other cycloalkyl moieties with straight-chain or branched alkyl groups as substituents. "Trialkylsilyl" includes $(CH_3)_3Si$, $(CH_3CH_2)_3Si$ and $[(CH_3)_3C](CH_3)_2Si$. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)cycloalkylamino" means a cycloalkylamino group where the hydrogen atom is replaced by an alkyl radical; examples include groups such as (methyl)cyclopropylamino, (ethyl)cyclobutylamino, (iso-propyl)cyclopentylamino and (methyl)cyclohexylamino. As indicated in the Summary of the Invention, the cycloalkyl in cycloalkylamino and (alkyl)cycloalkylamino is $C_3$-$C_6$ cycloalkyl. while the alkyl in (alkyl)cycloalkylamino is $C_1$-$C_4$ alkyl.

The term "aromatic" indicates that each of the ring atoms is essentially in the same plane and has a p-orbital perpendicular to the ring plane, and in which (4n+2) π electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. Aromatic carbocyclic ring or fused carbobicyclic ring systems includes fully aromatic carbocycles and carbocycles in which at least one ring of a polycyclic ring system is aromatic (e.g. phenyl, naphthyl and 1,2,3,4-tetrahydronaphthyl). The term "nonaromatic carbocyclic ring" denotes fully saturated carbocycles as well as partially or fully unsaturated carbocycles where the Hückel rule is not satisfied by the ring. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ling system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "halocycloalkyl" and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CHF_2O$, $CF_3O$, $CCl_3CH_2O$, $HCF_2CH_2CH_2O$ and $CF_3CH_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH3)C(=O)$.

The total number of carbon atoms in a substituent group is indicated by the "$C_i$-$C_j$" prefix where i and j are integers from 1 to 20. For example, $C_1$-$C_3$ alkylsulfonyl designates methylsulfonyl through propylsulfonyl.

In the above recitations, when a compound of Formula I contains a heterocyclic ring, all substituents are attached to this ring through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted" indicates that a moiety may be substituted or unsubstituted. The term "optionally substituted with from one to three substituents" and the like indicates that the moiety may be unsubstituted or from one to three of the available positions on the moiety may be substituted. When a moiety contains a substituent which can be hydrogen, for example $R^1$ or $R^5$, then, when this substituent is taken as hydrogen, it is recognized that this is equivalent to said moiety being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form. Some compounds of this invention can exist as one or more tautomers, and all tautomeric forms of such compounds are part of the present invention. Accordingly, the compounds of the invention may be present as a mixture of tautomers or the individual tautomers.

The present invention comprises compounds selected from Formula I, N-oxides and salts thereof. One skilled in the art will appreciate that not all nitrogen containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, Vol. 3, pp 18-19, A. J. Boulton and A. McKillop, Eds., Pergamon Press; M. R. Grimmett and B. R. T. Keene in *Advances in Heterocyclic Chemistry*, Vol. 43, pp 139-151, A. R. Katritzky, Ed., Academic Press; M. Tisler and B. Stanovnik in *Advances in Heterocyclic Chemistry*, Vol. 9, pp 285-291, A. R. Katritzky and A. J. Boulton, Eds., Academic Press; and G. W. H. Cheeseman and E. S. G. Werstiuk in *Advances in Heterocyclic Chemistry*, Vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic moiety such as a carboxylic acid or phenol.

Preferred for reasons of better activity and/or ease of synthesis are:

Preferred 1. Compounds of Formula I wherein
A and B are both O;
J is a 5- or 6-membered heteroaromatic ring selected from the group consisting of J-1, J-2, J-3 and J-4, each J ring optionally substituted with from one to three substituents independently selected from W and optionally substituted with $R^{12}$;

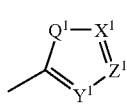

J-1

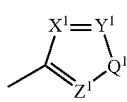

J-2

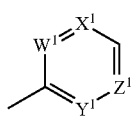

J-3

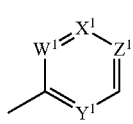

J-4

$Q^1$ is O, S or N—W; and
$W^1$, $X^1$, $Y^1$ and $Z^1$ are independently N or C—W, provided that in J-3 and J-4 at least one of $W^1$, $X^1$, $Y^1$ or $Z^1$ is N.

Preferred 2. Compounds of Preferred 1 wherein one substituent selected from the group consisting of $R^6$, $R^{11}$ and $R^{12}$ is present.

Preferred 3. Compounds of Preferred 2 with the Formula Is

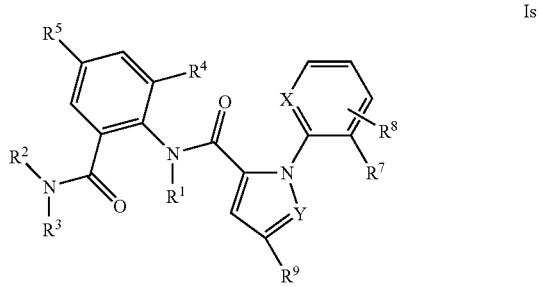

Is wherein
X is N or $CR^{10}$;
Y is N or CH;
$R^1$ is H; or $R^{11}$;
$R^2$ is $C_1$-$C_6$ alkyl;
$R^3$ is H; or $R^{11}$;
$R^4$ is $C_1$-$C_4$ alkyl or halogen;
$R^5$ is H, $C_1$-$C_4$ alkyl, $C_1$-$C_4$ haloalkyl or halogen;
$R^7$ is $C_1$-$C_4$ haloalkyl or halogen;
$R^8$ is H;
$R^9$ is $CF_3$, $OCF_3$, $OCHF_2$, $OCH_2CF_3$, $S(O)_pCF_3$, $S(O)_pCHF_2$ or halogen;
each $R^{11}$ is independently $C_1$-$C_6$ alkylthio; $C_1$-$C_6$ haloalkythio; phenylthio optionally substituted with from one to three substituents independently selected from W; $SN(R^{16})_2$; $R^{14}C(\!=\!O)L^1\!-$; $R^{14}L^2C(\!=\!O)S\!-$; $R^{14}L^2C(\!=\!O)NR^{13}S\!-$ or $R^{14}SO_2NR^{13}S\!-$;
$L^1$ is $NR^{13}$ or S;
each $L^2$ is independently O, $NR^{13}$ or S;
each $R^{13}$ is independently hydrogen; $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino and $C_3$-$C_6$ cycloalkylamino;
each $R^{14}$ is $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino and $C_3$-$C_6$ cycloalkylamino; or phenyl optionally substituted with one to three substituents independently selected from W; and
$R^{16}$ is $C_1$-$C_4$ alkyl or $C_1$-$C_4$ haloalkyl; or
$N(R^{16})_2$ can be taken together to form a ring containing a nitrogen atom and 2 to 6 atoms of carbon and optionally one additional atom of nitrogen, sulfur or oxygen, said ring optionally substituted with from one to four substituents selected from the group consisting of $C_1$-$C_2$ alkyl, halogen, CN, $NO_2$ and $C_1$-$C_2$ alkoxy;
provided that one $R^{11}$ is present.

Preferred 4. Compounds of Preferred 3 wherein

X is N;
Y is N;
$R^4$ is $CH_3$, F, Cl or Br;
$R^5$ is H, $CF_3$, F, Cl, Br or I;
$R^7$ is Cl or Br; and
$R^9$ is $CF_3$, $OCHF_2$, $OCH_2CF_3$, Cl or Br.

Of note are compounds of Preferred 3 and Preferred 4 wherein each $L^2$ is O; and each $R^{13}$ and each $R^{14}$ is independently $C_1$-$C_6$ alkyl. Of particular note are compounds of Preferred 3 and Preferred 4 wherein $R^{11}$ is $R^{14}L^2C(=O)NR^{13}S—$.

Preferred 5. Compounds of Preferred 2 wherein
$R^1$ is H;
$R^2$ is H or $C_1$-$C_6$ alkyl;
$R^3$ is $C_1$-$C_6$ alkyl;
$R^5$ is $C_1$-$C_{10}$ alkyl substituted with one substituent selected from the group consisting of CN, $NO_2$, $NH_2$, hydroxy and $R^6$; or $R^{12}$;
$R^6$ is $R^{19}C(=E)-$; $R^{19}C(=E)L-$; $R^{19}LC(=E)-$; or $(R^{19})LC(=E)L-$;
$R^{12}$ is $NH_2$; $R^{19}C(=E)-$; $R^{19}C(=E)L-$; $R^{19}LC(=E)-$; or $(R^{19})LC(=E)L-$;
each E is independently O or $NOR^{15}$;
each L is independently O or $NR^{18}$;
each $R^{15}$ is independently H or $C_1$-$C_4$ alkyl; and
each $R^{18}$ is independently H, $C_1$-$C_6$ alkyl or $C_1$-$C_6$ haloalkyl.

Of note are compounds of Preferred 5 wherein
$R^5$ is $R^{12}$;
$R^{12}$ is $NH_2$, $R^{19}C(=O)L-$ or $(R^{19})LC(=O)L-$;
each L is independently $NR^{18}$; and
each $R^{18}$ is independently H, $C_1$-$C_6$ alkyl or $C_1$-$C_6$ haloalkyl.

Also of note are compounds of Preferred 5 wherein
$R^5$ is $C_1$-$C_{10}$ alkyl substituted a with hydroxy; or $R^{12}$;
$R^{12}$ is $R^{19}C(=E)-$ or $R^{19}LC(=O)—$;
E is O or $NOR^{15}$;
L is O or $NR^{18}$;
$R^{15}$ is H or $C_1$-$C_4$ alkyl; and
$R^{18}$ is H, $C_1$-$C_6$ alkyl or $C_1$-$C_6$ haloalkyl.

Noteworthy compounds of Preferred 5 include the compounds:
Methyl 4-[[[1-(3-chloro-2-pyridinyl)-3-(trifluoromethyl)-1H-pyrazol-5-yl]carbonyl]amino]-3-methyl-5-[[(1-methylethyl)amino]carbonyl]benzoate,
N-[4-acetyl-2-methyl-6-[[(1-methylethyl)amino]carbonyl]phenyl]-1-(3-chloro-2-pyridinyl)-3-(trifluoromethyl)-1H-pyrazole-5-carboxamide, and
N-[4-benzoylamino-2-methyl-6-[[(1-methylethyl)amino]carbonyl]phenyl]-1-(3-chloro-2-pyridinyl)-3-(trifluoromethyl)-1H-pyrazole-5-carboxamide.

Preferred 6. Compounds of Preferred 2 wherein
$R^1$ is H;
$R^2$ is H or $C_1$-$C_6$ alkyl;
$R^3$ is $C_1$-$C_6$ alkyl;
$R^5$ is H, $C_1$-$C_4$ alkyl, $C_1$-$C_4$ haloalkyl or halogen;
$R^8$ is $C_1$-$C_{10}$ alkyl substituted with one substituent selected from the group consisting of CN, $NO_2$, $NH_2$, hydroxy and $R^6$; or $R^{12}$;
$R^6$ is $R^{19}C(=E)-$; $R^{19}C(=E)L-$; $R^{19}LC(=E)-$ or $(R^{19})LC(=E)L-$;
$R^{12}$ is $R^{19}C(=E^1)-$; $R^{19}C(=E^2)L-$; $R^{19}LC(=E^1)-$ or $(R^{19})LC(=E^2)L-$;
each E is independently O or $NOR^{15}$;
each $E^1$ is NOR$^{15}$;
each $E^2$ is independently O or $NOR^{15}$;
each L is independently O or $NR^{18}$;
each $R^{15}$ is independently H or $C_1$-$C_4$ alkyl; and
each $R^{18}$ is independently H, $C_1$-$C_6$ alkyl or $C_1$-$C_6$ haloalkyl and
each $R^{19}$ is independently H, $C_1$-$C_6$ alkyl, $C_1$-$C_6$ haloalkyl, $C_3$-$C_6$ cycloalkyl, or phenyl optionally substituted with from one to three substituents independently selected from W.

Of note are compounds of Preferred 6 wherein
$R^8$ is $C_1$-$C_{10}$ alkyl substituted with one substituent selected from the group consisting of $NH_2$, hydroxy and $R^6$; or $R^{12}$;
$R^6$ is $R^{19}C(=O)L-$;
$R^{12}$ is $R^{19}LC(=O)—$; and
each L is independently $NR^{18}$.

Noteworthy compounds include 1-[2-(hydroxymethyl)phenyl]-N-(2-methyl-6-[[(1-methylethyl)amino]carbonyl]phenyl]-3-(trifluoromethyl)-1H-pyrazole-5-carboxamide.

Preferred 7. Compounds of Preferred 2 wherein
$R^1$ is H;
$R^2$ is H or $C_1$-$C_6$ alkyl;
$R^3$ is $C_1$-$C_6$ alkyl substituted with one $R^6$;
$R^4$ is $C_1$-$C_4$ alkyl or halogen;
$R^5$ is H, $C_1$-$C_4$ alkyl, $C_1$-$C_4$ haloalkyl or halogen;
$R^6$ is $R^{19}C(=E^1)-$; $R^{19}C(=E^2)L-$; $R^{19}LC(=E^1)-$ or $(R^{19})LC(=E^2)L-$;
each $E^1$ is independently S, $NR^{15}$, $NOR^{15}$, $NN(R^{15}))_2$;
each $E^2$ is independently O, S, $NR^{15}$, $NOR^{15}$, $NN(R^{15})_2$;
each L is independently O or $NR^{18}$;
$R^7$ is $C_1$-$C_4$ haloalkyl or halogen;
$R^8$ is H;
$R^9$ is $CF_3$, $OCF_3$, $OCHF_2$, $OCH_2CF_3$, $S(O)_pCF_3$, $S(O)_pCHF_2$ or halogen;
each $R^{15}$ is independently H; $C_1$-$C_6$ haloalkyl; $C_1$-$C_6$ alkyl optionally substituted with one substituent selected from the group consisting of CN, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl and $C_1$-$C_4$ haloalkylsulfonyl;
each $R^{19}$ is independently H or $C_1$-$C_6$ alkyl; and
each p is independently 0, 1 or 2.

Preferred 8. Compounds of Preferred 7 wherein
$R^3$ is $C_1$-$C_6$ alkyl substituted with one $R^6$;
$R^6$ is $R^{19}C(=E^1)-$; and
$E^1$ is $NOR^{15}$.

Of note are compounds of Formula I (including, but not limited to Preferred 1, Preferred 2 and Preferred 5) wherein $R^5$ is $NH_2$.

Noteworthy compounds include N-[4-amino-2-methyl-6-[[(1-methylethyl)amino]carbonyl]phenyl]-1-(3-chloro-2-pyridinyl)-3-(trifluoromethyl)-1H-pyrazole-5-carboxamide.

This invention also pertains to methods for controlling an invertebrate pest comprising contacting the invertebrate pest or its environment with a biologically effective amount of a compound of Formula I, an N-oxide thereof or a salt thereof. Preferred methods are those comprising compounds of Formula I as preferred in Preferred 1 through 8, and the specifically preferred compounds above.

This invention also pertains to compositions for controlling an invertebrate pest comprising a biologically effective amount of a compound of Formula I, an N-oxide thereof or a salt thereof and at least one additional component selected from the group consisting of surfactants, solid diluents, liquid diluents and/or an effective amount of at least one additional biologically active compound or agent. Preferred compositions are those comprising compounds of Formula I as preferred in Preferred 1 through 8, and the specifically preferred compounds above.

Of note are compounds of Formula Ip, and N-oxides and agriculturally suitable salts thereof,

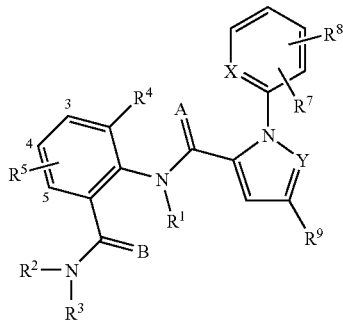

Ip wherein
A and B are independently O or S;
X is N or $CR^{10}$;
Y is N or CH;
$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of $R^6$, halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino and $C_3$-$C_6$ cycloalkylamino or $R^{11}$; or $R^{11}$;
$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;
$R^3$ is H; $R^{11}$; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl; $C_2$-$C_6$ alkylcarbonyl; $C_1$-$C_6$ alkyl $C_2$-$C_6$ alkenyl, $C_2$-$C_6$ alkynyl, $C_3$-$C_6$ cycloalkyl, each optionally substituted with one or more substituents selected from the group consisting of $R^6$, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_3$-$C_6$ trialkylsilyl, $R^{11}$, or a phenyl, phenoxy or 5- or 6-membered heteroaromatic ring, each ring optionally substituted with one to three substituents independently selected from W and optionally substituted with one $R^{12}$; or
$R^2$ and $R^3$ can be taken together with the nitrogen to which they are attached to form K;
$R^4$ is $C_1$-$C_4$ alkyl, $C_1$-$C_4$ haloalkyl, CN, halogen, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl;
$R^5$ and $R^8$ are each independently H; $R^{12}$; G; J; O-J; O-G; $S(O)_p$-J; $S(O)_p$-G; $S(O)_p$-phenyl optionally substituted with one to three substituents independently selected from W and optionally substituted with one $R^{12}$; $C_1$-$C_{10}$ alkyl, $C_2$-$C_6$ alkenyl, $C_2$-$C_6$ alkynyl, $C_1$-$C_4$ alkoxy or $C_1$-$C_4$ alkythio, each substituted with one or more substituents selected from the group consisting of G, J, $R^6$, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_2$-$C_6$ alkoxycarbonyl, $C_2$-$C_6$ alkylcarbonyl, $C_3$-$C_6$ trialkylsilyl, or a phenyl ring or a phenoxy ring, each ring optionally substituted with one to three substituents independently selected from W and optionally substituted with one $R^{12}$;
each $R^6$ is independently $R^{13}C(=E)$-; $R^{14}C(=E)L$-; $R^{13}LC(=E)$-; $(R^{14})LC(=E)L$-; $-O(Q=)P(OR^{14})_2$; $-SO_2LR^{13}$; or $R^{14}SO_2L$-;
$R^7$ is H, $C_1$-$C_4$ alkyl, $C_1$-$C_4$ haloalkyl, halogen, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl;
$R^9$ is $CF_3$, $OCF_3$, $OCHF_2$, $S(O)_pCF_3$, $S(O)_pCHF_2$ or halogen;
$R^{10}$ is H, $C_1$-$C_4$ alkyl, $C_1$-$C_4$ haloalkyl, halogen, CN or $C_1$-$C_4$ haloalkoxy;
each $R^{11}$ is independently $C_1$-$C_6$ alkylthio; $C_1$-$C_6$ haloalkylthio; phenylthio; $SN(R^{16})_2$; $R^{13}C(=O)$—; $R^{14}C(=O)L$-; $R^{13}LC(=O)$— or $R^{13}LC(=O)NR^{13}S$—;
each $R^{12}$ is independently $B(OR^{17})_2$; SH; thiocyanato, $C_3$-$C_8$ trialkylsilyloxy; $C_1$-$C_4$ alkyldisulfide; $SF_5$; $R^{13}C(=E)$-; $R^{14}C(=E)L$-; $R^{13}LC(=E)$-; $(R^{13})LC(=E)L$-; $-OP(=Q)(OR^{14})_2$; $-SO_2LR^3$; $R^{14}SO_2L$-;
each E is O, S, $NR^{15}$, $NOR^{15}$, $NN(R^{15})_2$, N—S=O, N—CN or N—$NO_2$;
each G is independently a 5- or 6-membered nonaromatic heterocyclic ring, optionally including one or two ring members selected from the group consisting of C(=O), SO or $S(O)_2$ and optionally substituted with 1 to 4 substituents selected from the group consisting of $C_1$-$C_2$ alkyl, halogen, CN, $NO_2$ and $C_1$-$C_2$ alkoxy; or
each G is independently $C_3$-$C_7$ cycloalkyl, $C_3$-$C_7$ halocycloalkyl, $C_3$-$C_7$ cyanocycloalkyl, $C_3$-$C_7$ alkylcycloalkyl, $C_4$-$C_8$ cycloalkylalkyl, $C_4$-$C_8$ halocycloalkylalkyl,
each J is independently a 5- or 6-membered heteroaromatic ring optionally substituted with one to three substituents independently selected from W and optionally substituted with $R^{12}$;
each K is a ring containing, in addition to the nitrogen atom to which the substituent pair $(R^{13})_2$, $(R^{15})_2$ or $(R^{16})_2$ is attached, from 2 to 6 atoms of carbon and optionally one additional atom of nitrogen, su or oxygen, said ring optionally substituted with from one to four substituents selected from the group consisting of $C_1$-$C_2$ alkyl, halogen, CN, $NO_2$ and $C_1$-$C_2$ alkoxy;
each L is independently O, $NR^{13}$ or S;
Q is O or S;
W is $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
each $R^{13}$ is independently hydrogen, $C_1$-$C_6$ alkyl or $C_1$-$C_6$ haloalkyl; or
$N(R^{13})_2$ can be taken together to form K;
each $R^{14}$ is $C_1$-$C_6$ alkyl, $C_1$-$C_6$ haloalkyl or phenyl optionally substituted with one to three substituents independently selected from W and optionally substituted with $R^{12}$;
each $R^{15}$ is independently hydrogen; $C_1$-$C_6$ haloalkyl; $C_1$-$C_4$ alkyl optionally substituted with one or more substituents selected from the group consisting of CN, $NO_2$, $R^6$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_2$-$C_6$ alkoxycarbonyl, $C_2$-$C_6$ alkylcarbonyl, $C_3$-$C_6$ trialkylsilyl or a phenyl ring optionally substituted with one to three substituents independently selected from W and optionally substituted with one $R^{12}$; or phenyl optionally substituted with one to three substituents independently selected from W and optionally substituted with $R^{12}$; or $N(R^{15})_2$ can be taken together to form K;

$R^{16}$ is $C_1$-$C_4$ alkyl or $C_1$-$C_4$ haloalkyl; or $N(R^{16})_2$ can be taken together to form K;

each $R^{17}$ is independently H or $C_1$-$C_4$ alkyl; or $B(OR^{17})_2$ can form a ring wherein the two oxygen atoms are linked by a chain of two to three carbons, optionally substituted with one or two substituents independently selected from methyl or $C_2$-$C_6$ alkoxycarbonyl; and p is 0, 1 or 2;

provided that when both (a) $R^5$ is H, $C_1$-$C_6$ alkyl, $C_1$-$C_6$ haloalkyl, $C_2$-$C_6$ haloalkenyl, $C_2$-$C_6$ haloalkynyl, $C_1$-$C_4$ haloalkoxy, $C_1$-$C_4$ haloalkylthio or halogen; and (b) $R^8$ is H, $C_1$-$C_6$ alkyl, $C_1$-$C_6$ haloalkyl, $C_2$-$C_6$ haloalkenyl, $C_2$-$C_6$ haloalkynyl, $C_1$-$C_4$ haloalkoxy, $C_1$-$C_4$ haloalkylthio, halogen, $C_2$-$C_4$ alkylcarbonyl, $C_2$-$C_6$ alkoxycarbonyl, $C_2$-$C_6$ alkylaminocarbonyl or $C_3$-$C_8$ dialkylaminocarbonyl; then both (c) at least one substituent selected from the group consisting of $R^6$, $R^{11}$ and $R^{12}$ is present; and (d) when $R^{12}$ is not present, at least one $R^6$ or $R^{11}$ is other than $C_2$-$C_6$ alkylcarbonyl, $C_2$-$C_6$ alkoxycarbonyl, $C_2$-$C_6$ alkylaminocarbonyl and $C_3$-$C_8$ dialkylaminocarbonyl.

Of particular note are compounds of Formula Ip wherein at least one group selected from $R^6$ and $R^{12}$ is present. Also of particular note are compounds of Formula Ip wherein at least one $R^{11}$ is present.

As noted above, certain $R^1$, $R^3$, $R^5$, $R^8$, $R^{13}$, $R^{14}$, $R^{15}$ and $R^{19}$ groups can be optionally substituted with one or more substituents. The term "optionally substituted" in connection with these $R^v$ groups (wherein v is 1, 3, 5, 8, 13, 14, 15 or 19) refers to $R^v$ groups that are unsubstituted or have at least one non-hydrogen substituent. Examples of optionally substituted $R^v$ groups are those that are optionally substituted by replacement of a hydrogen on a carbon atom of the $R^v$ group with one or more (up to the total number of hydrogens available for replacement in any specific $R^v$ group) substituents independently selected from the substituents listed in the Summary of the Invention above. Although these substituents are listed, it is noted that they do not need to be present since they are optional substituents. Of note are $R^v$ groups that are unsubstituted. Of note are $R^v$ groups substituted with from one to five substituents. Also of note are $R^v$ groups substituted with one substituent.

As noted above, each J is independently a 5- or 6-membered heteroaromatic ring optionally substituted with from one to three substituents independently selected from W and optionally substituted with $R^{12}$. The term "optionally substituted" in connection with these J groups refers to groups that are unsubstituted or have at least one non-hydrogen substituent. Examples of 5- or 6-membered heteroaromatic rings include the rings U-1 through U-48 illustrated in Exhibit 1. Note that each of the U-rings can be optionally substituted with from one to three substituents independently selected from W and optionally substituted with $R^{12}$ (said W and $R^{12}$ groups are not illustrated in Exhibit 1 since they are optional substituents). Note that J-1 through J-4 above also denote 5- or 6-membered heteroaromatic rings. Note that U-1 through U-19 are examples of J-1, U-20 through U-35 are examples of J-2, U-36 through U-43 are examples of J-3 and U-44 through U-48 are examples of J-4. The nitrogen atoms that require substitution to fill their valence are substituted with H or W. Note that some U groups can only be substituted with less than 3 W and/or one $R^{12}$ groups (e.g. U-13, U-14, U-17 through U-20 and U-31 through U-33 and U-35 can only be substituted with one group).

Exhibit 1

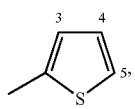
U-1

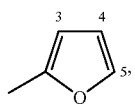
U-2

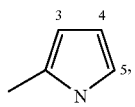
U-3

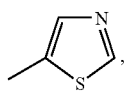
U-4

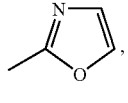
U-5

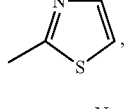
U-6

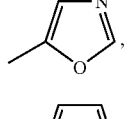
U-7

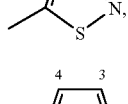
U-8

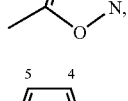
U-9

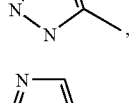
U-10

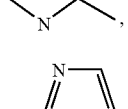
U-11

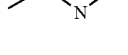
U-12

-continued
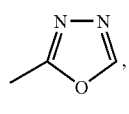 U-13
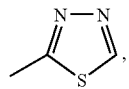 U-14
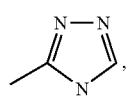 U-15
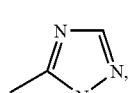 U-16
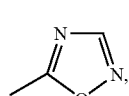 U-17
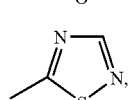 U-18
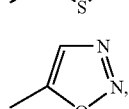 U-19
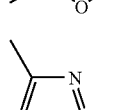 U-20
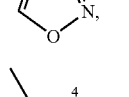 U-21
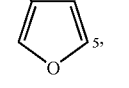 U-22
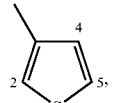 U-23
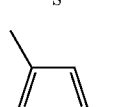 U-24
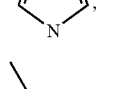 U-25
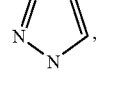 U-26
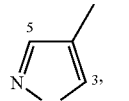
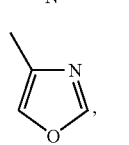
-continued
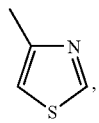 U-27
 U-28
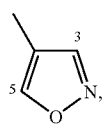 U-29
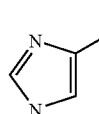 U-30
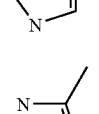 U-31
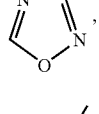 U-32
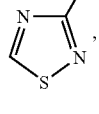 U-33
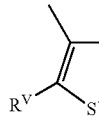 U-34
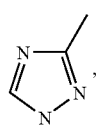 U-35
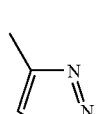 U-36
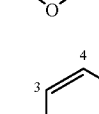 U-37
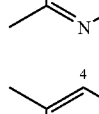 U-38
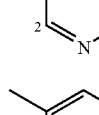
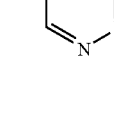

-continued

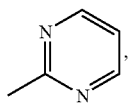
U-39

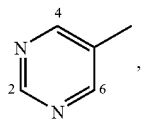
U-40

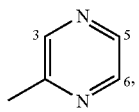
U-41

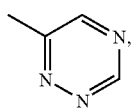
U-42

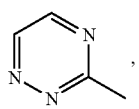
U-43

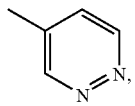
U-44

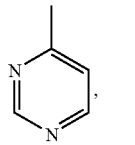
U-45

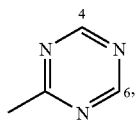
U-46

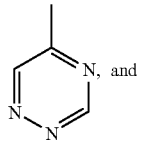
U-47

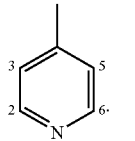
U-48

As noted above, each G is independently (among others) a 5- or 6-membered nonaromatic heterocyclic ring optionally including one or two ring members selected from the group consisting of C(=O), SO or S(O)$_2$, optionally substituted with from one to four substituents selected from the group consisting of $C_1$-$C_2$ alkyl, halogen, CN, NO$_2$ and $C_1$-$C_2$ alkoxy. The term "optionally substituted" in connection with these G groups refers to groups that are unsubstituted or have from one to four non-hydrogen substituents. Examples of such G groups include those illustrated as G-1 through G-35 in Exhibit 2. Note that when the attachment point on these G groups is illustrated as floating, the G group can be attached to the remainder of Formula I through any available carbon or nitrogen of the G group by replacement of a hydrogen atom. The optional substituents can be attached to any available carbon or nitrogen by replacing a hydrogen atom (said substituents are not illustrated in Exhibit 2 since they are optional substituents). Note that when G comprises a ring selected from G-24 through G-31, G-34 and G-35, $Q^2$ is selected from O, S, NH or N($C_1$-$C_2$ alkyl).

Exhibit 2

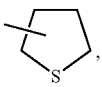
G-1

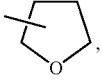
G-2

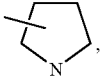
G-3

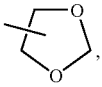
G-4

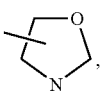
G-5

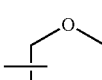
G-6

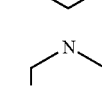
G-7

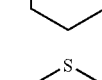
G-8

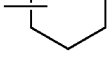
G-9

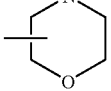
G-10

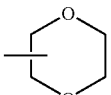
G-11

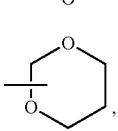
G-12

-continued

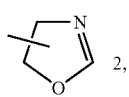 G-13

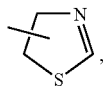 G-14

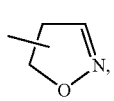 G-15

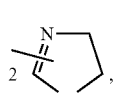 G-16

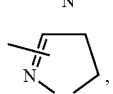 G-17

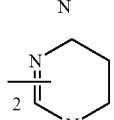 G-18

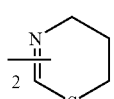 G-19

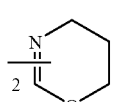 G-20

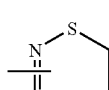 G-21

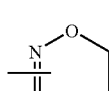 G-22

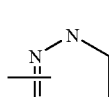 G-23

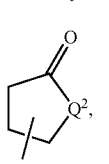 G-24

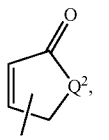 G-25

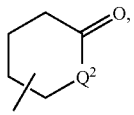 G-26

-continued

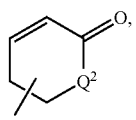 G-27

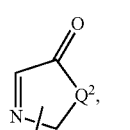 G-28

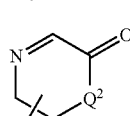 G-29

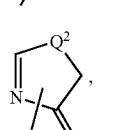 G-30

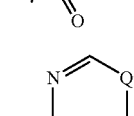 G-31

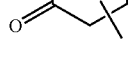 G-32

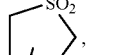 G-33

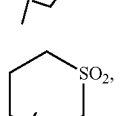 G-34

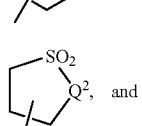 G-35

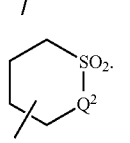

One or more of the following methods and variations as described in Schemes 1-29 can be used to prepare the compounds of Formula I. The definitions of A, B, G, J, $R^1$ through $R^7$, m, n and p in the compounds of Formulae 2-67 below are as defined above. Compounds of Formulae Ia-f, 2a-b, 4a-k, 5a-b are various subsets of the compounds of Formula I, 2, 4 and 5. In the schemes, Het is the moiety shown below:

Het is
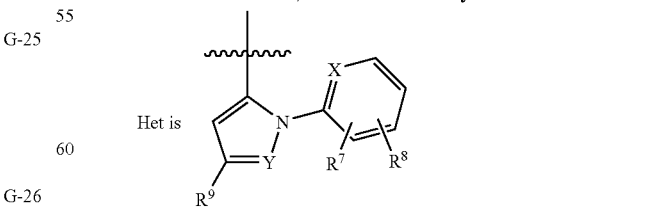

wherein the wavy line indicates the bond that connects said moiety to the rest of the formula for a given compound.

A typical procedure for the preparation of Formula I is detailed in Scheme 1 and involves coupling of an amine of Formula 2 with an acid chloride of Formula 3 in the presence of an acid scavenger to provide the compound of Formula Ia. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances, polymer-supported acid scavengers such as polymer-bound diisopropylethylamine and polymer-bound dimethylaminopyridine may be used. The coupling can be run in a suitable inert solvent such as tetrahydrofuran, dioxane, diethylether or dichloromethane to afford the anilide of Formula Ia. In a subsequent step, amides of Formula Ia can be converted to thioamides of Formula Ib using a variety of standard thio transfer reagents including phosphorus pentasulfide and Lawesson's reagent.

Scheme 1

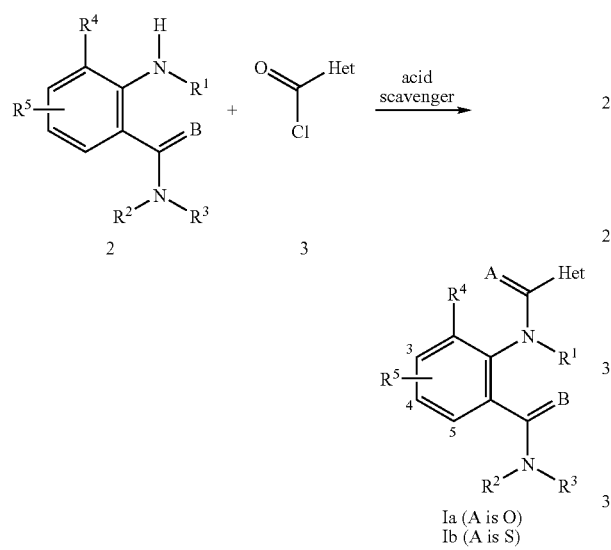

An alternate procedure for the preparation of compounds of Formula Ia involves coupling of an amine of Formula 2 with an acid of Formula 4 in the presence of a dehydrating agent such as dicyclohexylcarbodiimide (DCC), 1,1'-carbonyldiimidazole, bis(2-oxo-3-oxazolidinyl)phosphinic chloride or benzotriazol-1-yloxytris(dimethylamino)phosphonium hexafluorophosphate. Polymer supported reagents are also useful here, such as polymer-bound cyclohexylcarbodiimide. The coupling can be run in a suitable inert solvent such as dichloromethane or N,N-dimethylformamide. Synthetic procedures of Schemes 1 and 2 are only representative examples of useful methods for the preparation of Formula I compounds as the synthetic literature is extensive for this type of reaction.

Scheme 2

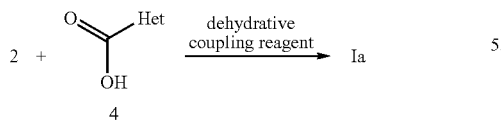

One skilled in the art will also realize that acid chlorides of Formula 3 may be prepared from acids of Formula 4 by numerous well-known methods. For example, acid chlorides of Formula 3 are readily made from carboxylic acids of Formula 4 by reacting the carboxylic acid 4 with thionyl chloride or oxalkyl chloride in an inert solvent such as toluene or dichloromethane in the presence of a catalytic amount of N,N-dimethylformamide.

Amines of Formula 2a are typically available from the corresponding 2-nitrobenzamides of Formula 5 via catalytic hydrogenation of the nitro group (Scheme 3). Typical procedures involve reduction with hydrogen in the presence of a metal catalyst such as palladium on carbon or platinum oxide and in hydroxylic solvents such as ethanol and isopropanol. They can also be prepared by reduction with zinc in acetic acid. These methods for reducing nitro groups are well documented in the chemical literature. $R^1$ substituents such as alkyl, substituted alkyl and the like can generally be introduced at this stage through known procedures including either direct alkylation or through the generally preferred method of reductive alkylation of the amine. A commonly employed procedure is to combine the amine 2a with an aldehyde in the presence of a reducing agent such as sodium cyanoborohydride to produce the Formula 2b compounds where $R^1$ is alkyl, alkenyl, alkynyl or substituted derivatives thereof.

Scheme 3

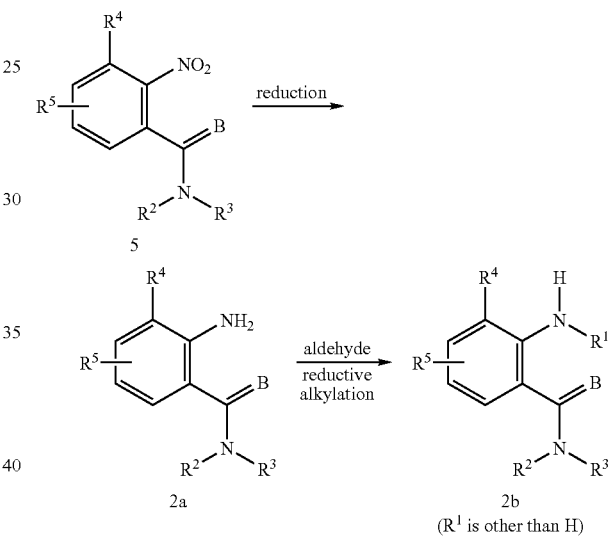

Scheme 4 shows that compounds of Formula Ic can be alkylated with a suitable alkylating agent such as an alkyl halide in the presence of a base such as sodium hydride or n-butyl lithium in an inert solvent such as tetrahydrofuran or N,N-dimethylformamide to afford anilides of Formula Id wherein $R^1$ is other than hydrogen. This procedure is especially useful for preparing compounds of Formula Id in which $R^1$ is alkyl, alkenyl or alkynyl.

Scheme 4

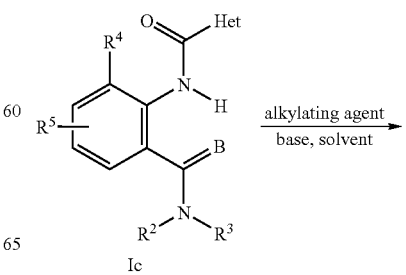

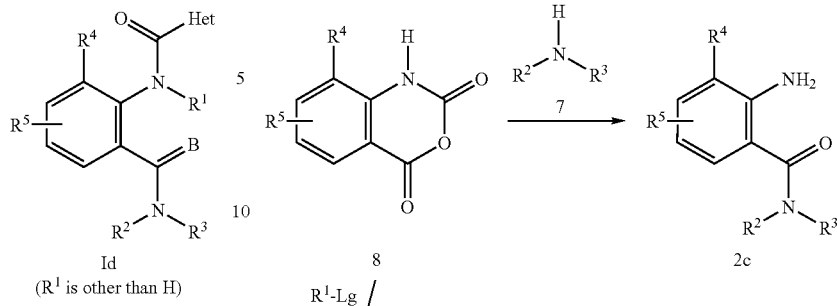

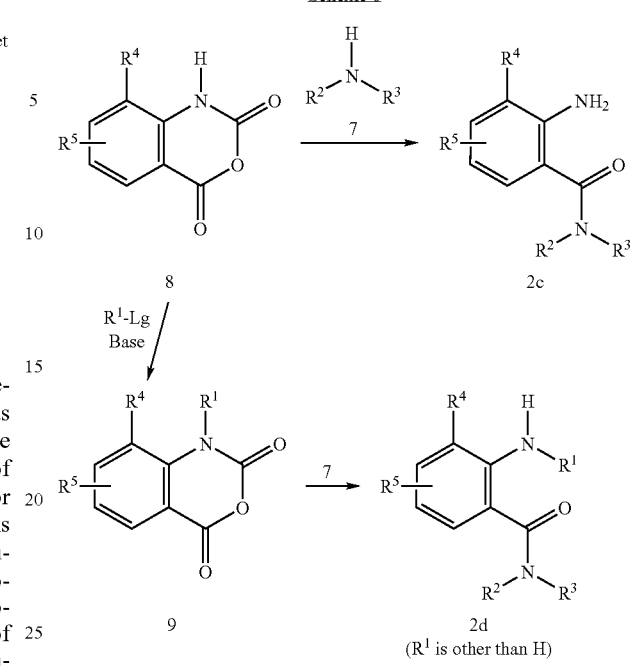

The intermediate amides of Formula 5a are readily prepared from commercially available 2-nitrobenzoic acids (Scheme 5). Typical methods for amide formation can be applied here. These include direct dehydrative coupling of acids of Formula 6 with amines of Formula 7 using for example DCC, and conversion of the acids to activated forms such as the acid chlorides or anhydrides and subsequent coupling with amines to form amides of Formula 5a. Alkyl chloroformates, such as ethyl chloroformate or isopropyl chloroformate, are especially useful reagents for this type of reaction involving activation of the acid. The chemical literature is extensive on amide formation of this type. Amides of Formula 5a are readily converted to thioamides of Formula 5b by using commercially available thio transfer reagents such as phosphorus pentasulfide and Lawesson's reagent.

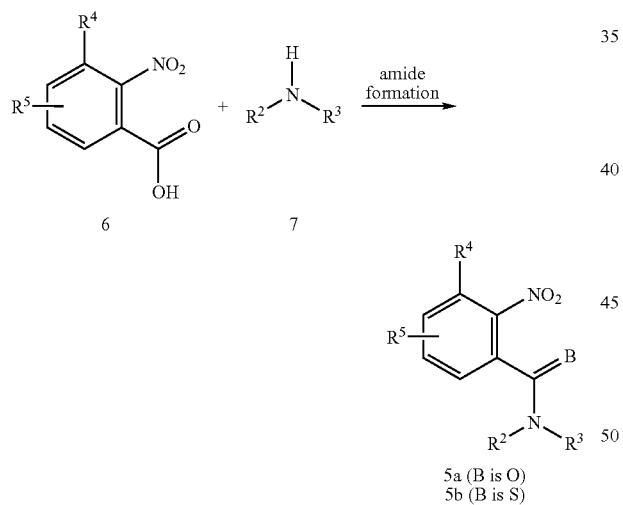

Intermediate anthranilic amides of Formula 2c and 2d may also be prepared from isatoic anhydrides of Formula 8 and 9 (Scheme 6). Typical procedures involve combination of equimolar amounts of the amine 7 with the isatoic anhydride in polar aprotic solvents such as pyridine and N,N-dimethylformamide at temperatures ranging from room temperature to 100° C. $R^1$ substituents such as alkyl and substituted alkyl may be introduced by the base catalyzed alkylation of isatoic anhydride 8 with known alkylating reagents $R^1$-Lg (wherein Lg is a leaving group such as halogen, alkyl or aryl suphonates or alkyl sulfates) to provide the alkyl substituted intermediates 9. Isatoic anhydrides of Formula 8 may be made by methods described in Coppola, *Synthesis* 1980, 505-36.

As shown in Scheme 7 an alternate procedure for the preparation of specific compounds of Formula Ic involves reaction of an amine 7 with a benzoxazinone of Formula 10. Typical procedures involve combination of the amine with the benzoxazinone in solvents such as tetrahydrofuran or pyridine at temperatures ranging from room temperature to the reflux temperature of the solvent. Benzoxazinones are well-documented in the chemical literature and are available via known methods that involve the coupling of either an anthranilic acid or an isatoic anhydride with an acid chloride. For references to the synthesis and chemistry of benzoxazinones see Jakobsen et al, *Biorganic and Medicinal Chemistry*, 2000, 8, 2095-2103 and references cited within. See also Coppola, *J. Heterocyclic Chemistry*, 1999, 36, 563-588.

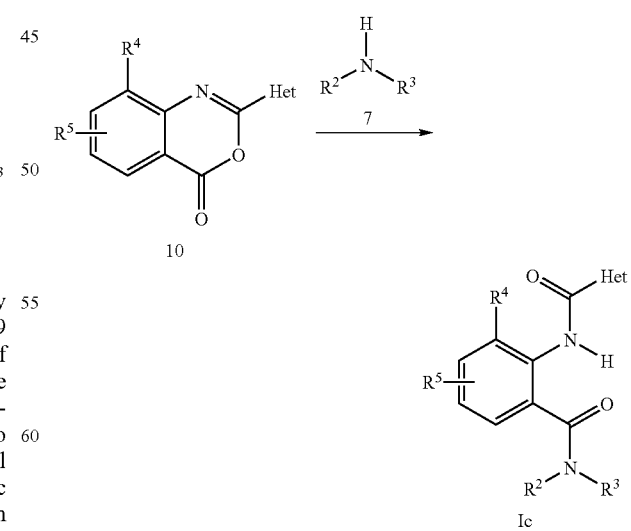

A preferred set of compounds of Formula Ic contains an oxime group in the $R^3$ substituent. Amine of Formula 7 containing an oxime side chain are known (see e.g. U.S. Pat. No. 5,211,738 and European Patent Application EP 117,477). The benzoxazinone route of Scheme 7 is the preferred method for the preparation of compounds of Formula Ic containing an oxime group in the $R^3$ substituent.

The syntheses of representative acids of Formula 4 are depicted in Schemes 8-11. Synthesis of pyrazoles of Formula 4a are described in Scheme S. The synthesis of compounds of Formula 4a in Scheme 8 involves as the key step introduction of the phenyl or pyridinyl substituent via arylation of the pyrazole with compounds of Formula 12. Oxidation of the methyl group affords the pyrazole carboxylic acid. Some of the more preferred $R^9$ groups include haloalkyl.

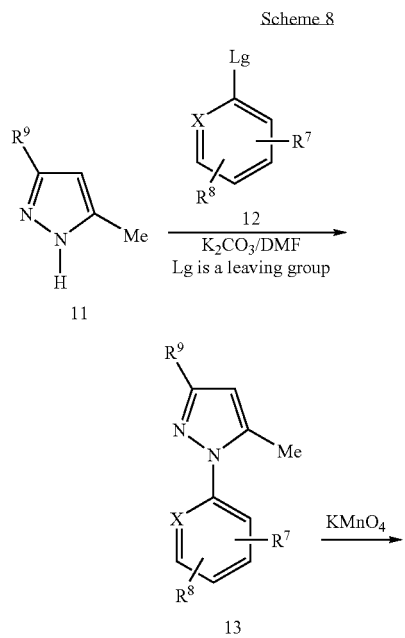

Scheme 8

Synthesis of pyrazoles and pyrroles of Formula 4b are described in Scheme 9. These acids may be prepared via metallation and carboxylation of compounds of Formula 15 as the key step. The phenyl or pyridinyl group is introduced in a manner similar to that of Scheme 7, i.e. via arylation with a compound of Formula 12. Representative $R^9$ groups include e.g. cyano, haloalkyl and halogen.

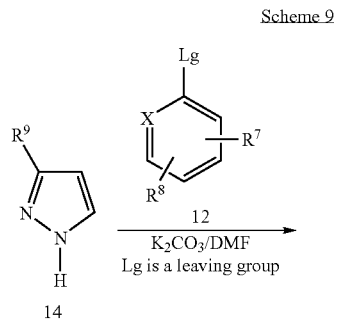

Scheme 9

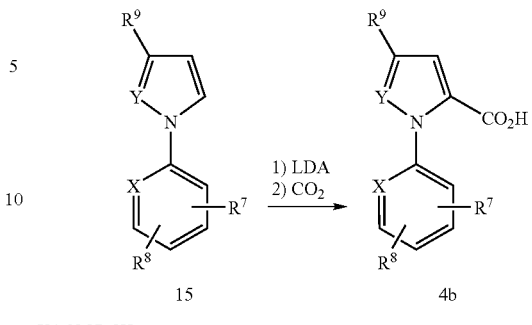

Y is N OR CH

The synthesis of pyrazoles of Formula 4c is described in Scheme 10. They can be prepared via reaction of an optionally substituted hydrazine of Formula 16 with a pyruvate of Formula 17 to yield pyrazole esters of Formula 18. Hydrolysis of the esters affords the pyrazole acids of Formula 4c. This procedure is particularly useful for the preparation of compounds in which the substituent is optionally substituted phenyl and $R^9$ is haloalkyl.

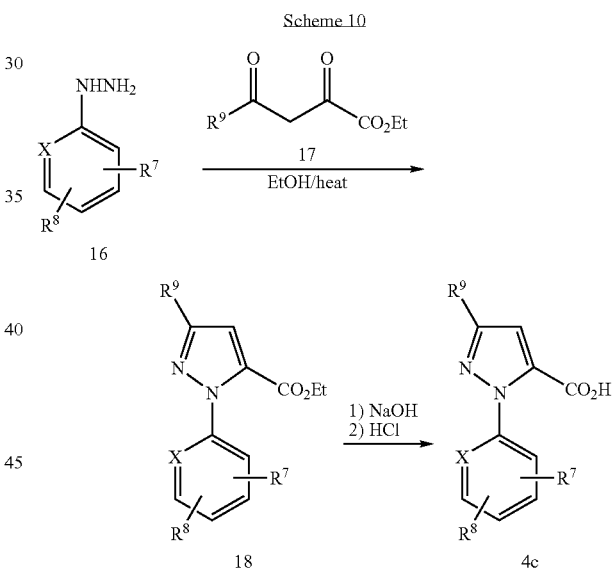

Scheme 10

The synthesis of pyrazole acids of Formula 4d is described in Scheme 11. They can be prepared via 3+2 cycloaddition of an appropriately substituted nitrilimine with either substituted propiolates of Formula 20 or acrylates of Formula 23. Cycloaddition with acrylates requires additional oxidation of the intermediate pyrazoline to the pyrazole. Hydrolysis of the esters affords the pyrazole acids of Formula 4d. Preferred iminohalides for this reaction include the trifluoromethyl iminochloride of Formula 25 and the iminodibromide of Formula 26. Compounds such as 25 are known (*J. Heterocycl. Chem.* 1985, 22(2), 565-8). Compounds such as 26 are available by known methods (*Tetrahedron Letters* 1999, 40, 2605). These procedures are particularly useful for the preparation of compounds where the substituent is optionally substituted phenyl (X is $CR^{10}$) and $R^9$ is haloalkyl or bromo.

Scheme 11

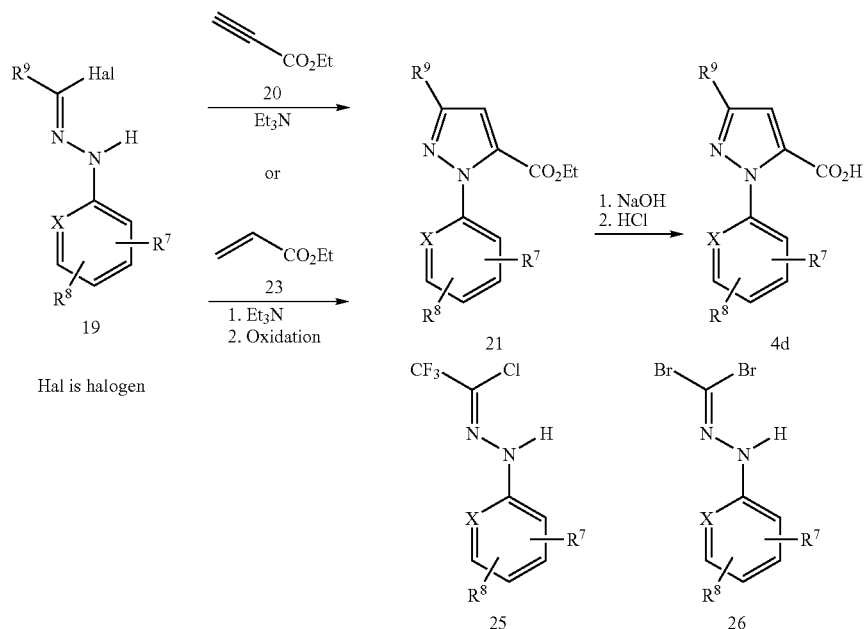

Scheme 12 shows the synthesis of pyrrole acids of structure 4e.

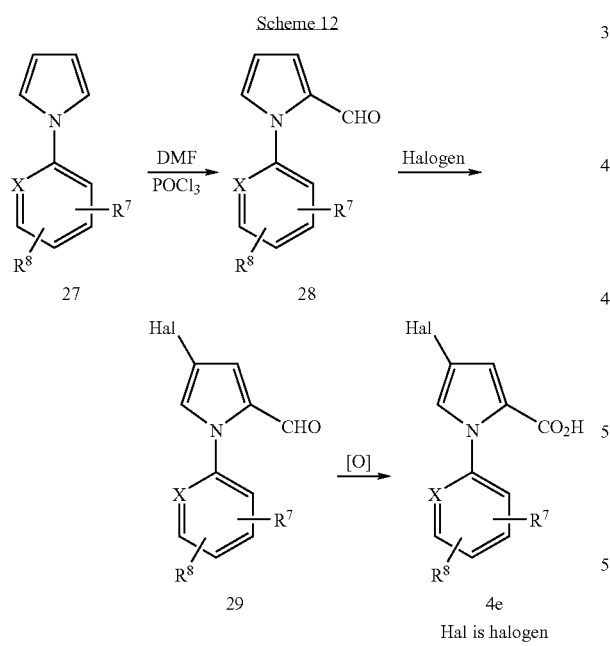

Compounds of Formula 27 may be formylated with formylating agents such as N,N-dimethylformamide combined with an activating agent such as phosphorous oxychloride, thionyl chloride, or oxalkyl chloride to give aldehydes of Formula 28. Halogenation of compounds of Formula 28 with molecular halogens or N-halosuccinimides give compounds of Formula 29. Oxidation of the aldehyde function with a variety of known reagents such as silver oxide, alkali dichromates, or alkali chlorates gives the acids of Formula 4e.

As shown in Scheme 13, compounds of Formula If wherein either $R^1$ or $R^3$ is alkylcarbonyl, alkoxycarbonyl, or sulfenyl may be made by the treatment of a compound of Formula Ie with an activated chloride of Formula 30 in the presence of an acid acceptor.

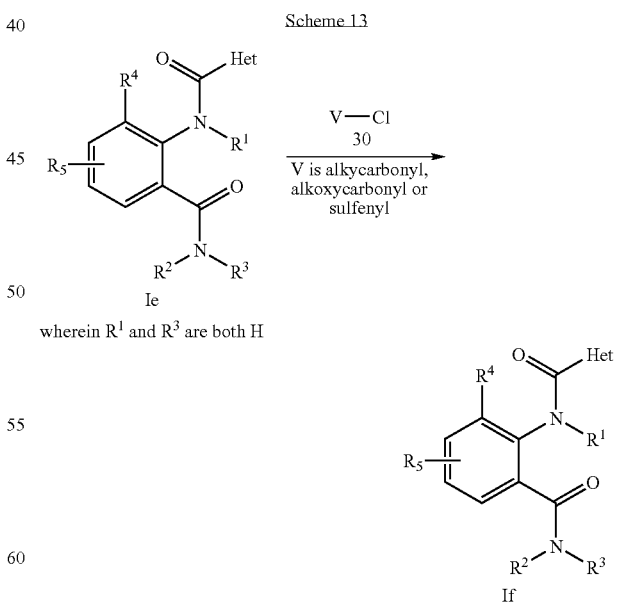

Compounds of Formula 30 wherein V is alkylcarbonyl are well-known in the art and can generally be prepared by reaction of the corresponding carboxylic acid with a chlorinating agent such as thionyl chloride or oxalkyl chloride in an inert solvent such as toluene or dichloromethane in the presence of a catalytic amount of N,N-dimethyl-formamide. Compounds of Formula 30 wherein V is alkoxycarbonyl are well known in the art and can generally be prepared by reaction of alcohols with phosgene.

Compounds of Formula 30 wherein V is sulfenyl can be prepared by methods described in Kuehle, *Synthesis*, 1970, 561. N-chlorosulfenylcarbamates, compounds of Formula 30 wherein V is $R^{13}OC(=O)NR^{13}S(O)_n$— can be prepared according to procedures in U.S. Pat. No. 3,843,689. Other sulfenyl halides have been prepared similarly (see U.S. Pat. No. 3,843,689 and European Patent Application EP395581). These references also describe N-sulfenylation of amides and other analogs by reaction with sulfenyl halides in the presence of base.

As shown in Scheme 13a, sulfenyl compounds of Formula Ig, compounds wherein $R^1$ or $R^3$ is $R^{11}$ bonded through a sulfur atom (e.g. wherein $R^{11}$ is $C_1$-$C_6$ alkylthio; $C_1$-$C_6$ haloalkythio; phenylthio optionally substituted with from one to three substituents independently selected from W; $(R^{16})_2NS(O)_n$—; $R^{14}C(=O)L$-; $R^{13}LC(=O)S$—; $R^{13}C(=O)NR^{13}S(O)_n$—; $R^{13}LC(=O)NR^{13}S(O)_n$— or $R^{13}LSO_2NR^{13}S(O)_n$; and n is 0) can be oxidized to compounds of Formula Ih (e.g. wherein $R^{11}$ is $C_1$-$C_6$ alkylsulfenyl; $C_1$-$C_6$ haloalkylsulfenyl; phenylsulfenyl optionally substituted with from one to three substituents independently selected from W; $(R^{16})_2NS(O)_n$—; $R^{14}C(=O)L$-; $R^{13}LC(=O)S$—; $R^{13}C(=O)NR^{13}S(O)_n$—; $R^{13}LC(=O)NR^{13}S(O)_n$— or $R^{13}LSO_2NR^{13}S(O)_n$; and n is 1) by treatment with hydrogen peroxide, organic peroxides including peracids such as perbenzoic acid or peracetic acid, potassium persulfate, sodium persulfate, ammonium persulfate or potassium monopersulfate (e.g., Oxone®).

Scheme 13a

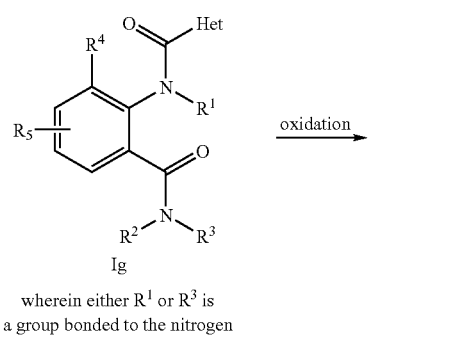

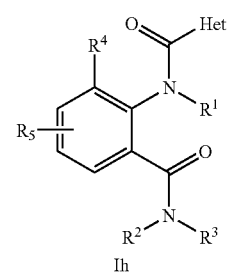

wherein either $R^1$ or $R^3$ is
a group bonded to the nitrogen
through a S(O) moeity Compounds of Formula 33 (where $R^{12}$ contains a nitrogen atom attached to the benzene ring) can be made via nitro-substituted compounds of Formula 31 as shown in Scheme 14. Reduction of nitro compounds is a well known process and can be carried out in a number of different ways such as, for example, via catalytic hydrogenation, iron-acetic acid reduction, zinc-trifluoroacetic acid reduction or tin (II) chloride reduction (See Larock, *Comprehensive Organic Transformations, pages* 411-415, 1989, VCH, New York for a variety of methods of nitro group reductions). Catalytic reduction with a palladium or platinum catalyst under an atmosphere of hydrogen is a preferred method for carrying out this transformation. Acylation or sulfonylation of intermediates of Formula 32 in the presence of acid acceptors gives the compound of Formula 33. Preferred acid acceptors are alkali carbonates, alkali hydroxides, and tertiary amines. Suitable reagents for acylation or sulfonylation in this route include acid anhydrides, acid chlorides, sulfonyl halides, isocyanates, chloroformates, and carbamyl chlorides. Preferred solvents include dichloromethane, tetrahydrofuran, N,N-dimethylformamide, acetonitrile, and ethyl acetate. Acylation and sulfonylation of amines is well known in the art.

Scheme 14

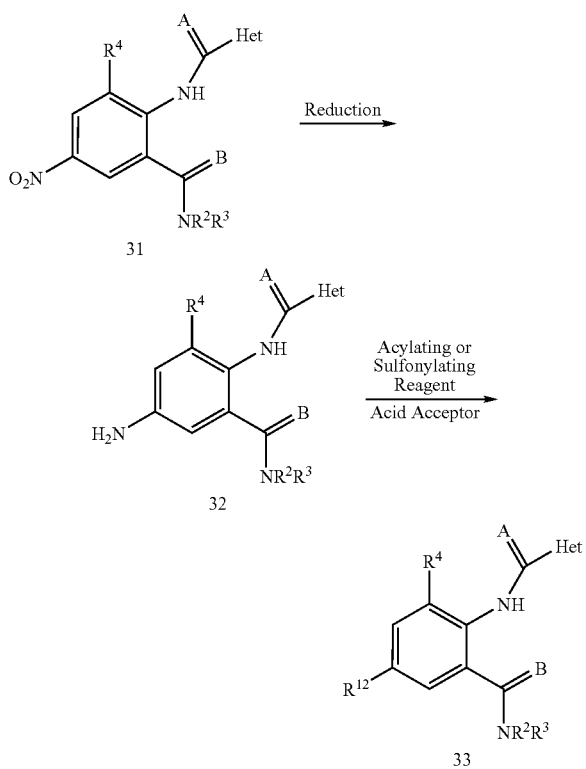

As shown in Scheme 15, compounds of Formula 35, 36, and 37 containing esters, amides and ketones respectively may be made via carbonylation of halides and sulfonates of Formula 34. Palladium-catalyzed reaction of aromatic halides and sulfonates in the presence of carbon monoxide and nucleophiles is well known in the art. Suitable nucleophiles include alcohols, amines, boronic acids, and organotins. To synthesize esters or amides 35 or 36 the compound of Formula 34 is treated with an alcohol or amine under an atmosphere of carbon monoxide in the presence of a palladium catalyst and a phosphine ligand in an aprotic solvent such as dimethyl sulfoxide, N,N-dimethylformamide or N-methylpyrollidinone. The reaction can be carried out at 25-120° C. The preferred catalyst system is generated from palladium acetate and diphenylphosphino propane. Leading references for the transformation are found in *Tetrahedron Letters*, 1992, 33, 1959-1962. Organotin or organoboron compounds may be used in the reaction to produce ketones of Formula 37 as products. See *Synthesis* 1992, 803-815, *Angewandte Chemie* Int. Ed., 1986, 25, 508-524 and *J. Org. Chem.*, 1998, 63, 4726 and references therein for procedures and conditions for the transformation of halides and sulfonates to ketones. An additional method for transformation of halides and sulfonates to methyl ketones without the need for carbon monoxide is disclosed in *Bull. Chem. Soc. Japan* 1987, 60, 767-8.

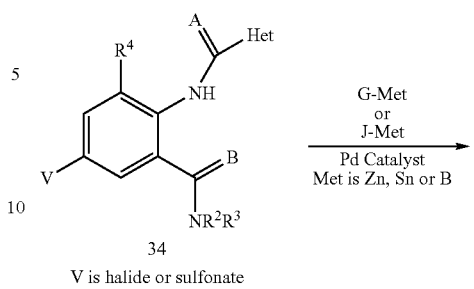

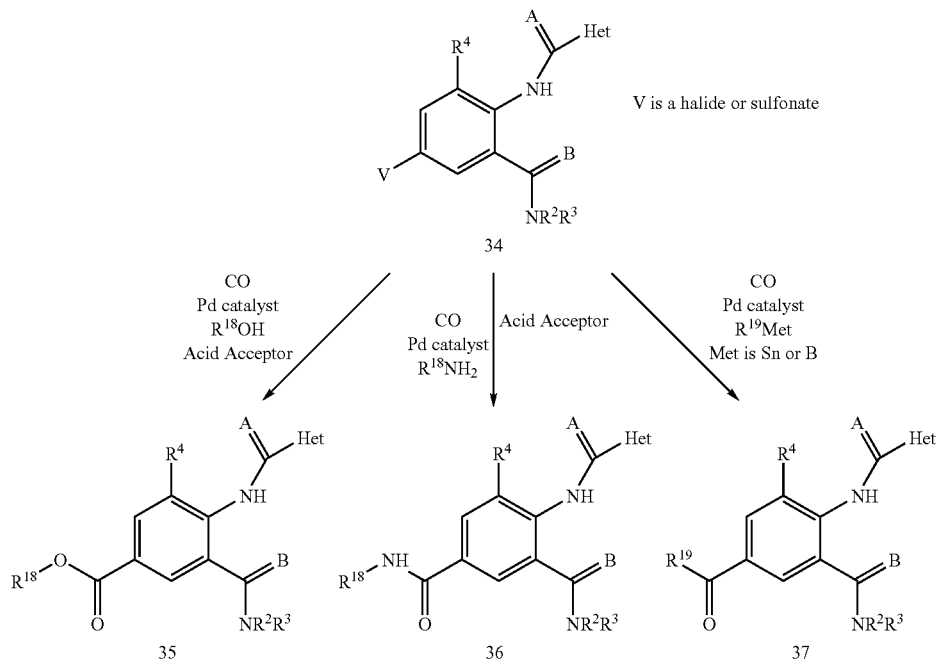

Scheme 16 shows the transformation of compounds of Formula 34 to compounds of Formula 38 (wherein the substituent is either G or J depending on the organometallic reagent used). The introduction of heteroaromatic groups by transition metal catalyzed cross coupling reactions is will known in the art. A variety of heterocyclic organometallic reagents will couple with halides and sulfonates of Formula 34 (such as zinc, boron and tin reagents). Specific conditions suitable for the transformation of halides and sulfonates into heteroaromatic groups can be found in *Synthesis* 1992, 413-432 and *Advances in Heterocyclic Chemistry*, 1995, 62, 305-418. Synthesis of many heteroaromatic reagents suitable for coupling are found in these references as well. Generally, the reaction requires the use of a palladium or nickel catalyst, a halide or sulfonate of Formula 34, and the heterocyclic organometallic reagent (G-Met or J-Met). Suitable solvents include N,N-dimethylformamide, N-methylpyrrolidinone, tetrahydrofuran, dioxane, and other solvents which do not react with the organometallic reagent. In the case of boronic acids the presence of an alkali carbonate base and mixed aqueous and organic solvents are preferred. Reaction temperatures between 0 and 120° C. are preferred. Preferred catalysts include $Pd(PPh_3)_2Cl_2$ and $Pd(PPh_3)_4$.

-continued

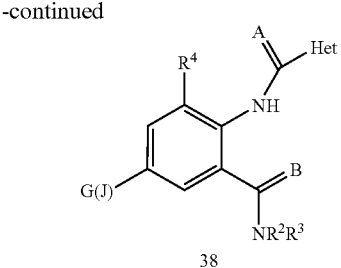

Isatins of Formula 40 can be made by demethylation of methoxy-substituted compounds of Formula 39 in Scheme 17. Further alkylation, acylation, phosphorylation and sulfonylation with appropriate halides in the presence of acid acceptors gives isatins of formula 41 (wherein $R^5$ represents those $R^5$ substituents bonded to the ring by O such as O-J; O-G; or $C_1$-$C_4$ alkoxy substituted with one or more substituents selected from the group consisting of G, J, $R^6$, halogen, CN, $NO_2$, $NH_2$, hydroxy, $C_1$-$C_4$ alkoxy, $C_1$-$C_4$ haloalkoxy). For demethylation of methyl ethers see Brooks et. al. *J. Org Chem.* 1999, 64, 9719-9721 and references therein for different reagents and conditions to carry out this transformation. Many reagents are useful for this transformation, but a preferred method is to use boron tribromide in dichloromethane. The transformation can be carried out at temperatures between −70 and 110° C. For functionalization of the phenol products of Formula 40 by alkylation, acylation, phosphorylation and sulfonylation with appropriate halides, preferred acid acceptors are alkali carbonates, alkali hydroxides, and tertiary amines. Preferred solvents include dichloromethane, tetrahydrofuran, N-methylpyrrolidinone, N,N-dimethyl-formamide, acetonitrile, and ethyl acetate. The use of the demethylation and alkylation procedures may also be carried at the anthranilic acid or final product stage of synthesis.

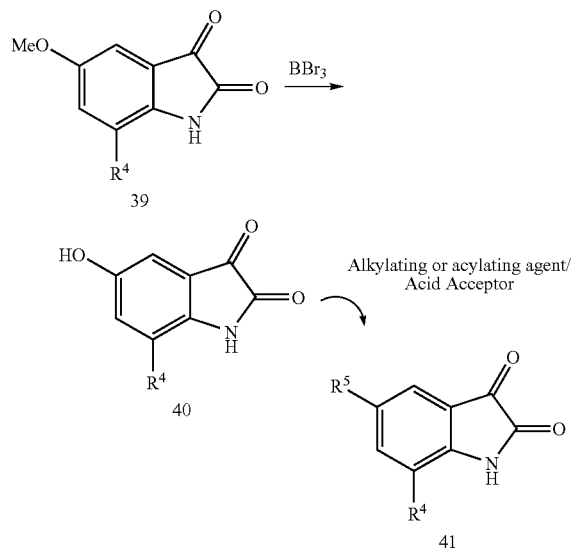

The nucleophilic substitution of halonitrocarboxamides of Formula 42 to give compounds of Formula 43 is shown in Scheme 18. Reaction of the compound of Formula 42 with nucleophiles such as alkoxides and thiolates leads to compounds of Formula 43. Suitable solvents include, but are not limited to N,N-dimethylformamide, N-methylpyrrolidinone, dimethyl sulfoxide, tetrahydrofuran, and dioxane. The displacement can be carried out at temperatures from 0 to 160° C. This method is suitable for synthesizing compounds of Formula 43 in which $R^5$ represents an $R^5$ substituents which is attached to the aromatic ring by O or S such as (but not limited to) substituents selected from OJ, OG, SJ, SG, cycloalkoxy, alkenyloxy, alkynyloxy, optionally substituted alkoxy and optionally substituted alkylthio substituents.

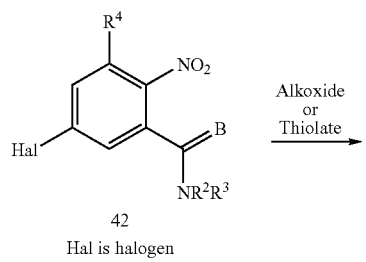

Hal is halogen

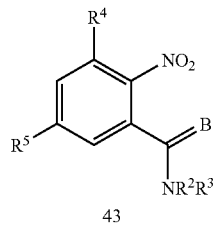

$R^5$ represents a substituent bonded through S or O

As shown in Scheme 18a, sulfenyl compounds of Formula 43a, compounds wherein the $R^5$ substituents which are attached to the aromatic ring by S such as (but not limited to) SJ, SG and optionally substituted phenylthio substituents can be oxidized to compounds of Formula 44 (e.g. wherein $R^5$ is $S(O)_p$-J; $S(O)_p$-G; $S(O)_p$-(optionally substituted phenyl) and p is 1 or 2) by treatment with hydrogen peroxide, organic peroxides including peracids such as perbenzoic acid or peracetic acid, potassium persulfate, sodium persulfate, ammonium persulfate or potassium monopersulfate (e.g., Oxone®). One (for when p is one) or two (for when p is two) equivalents of oxidizing agent are used.

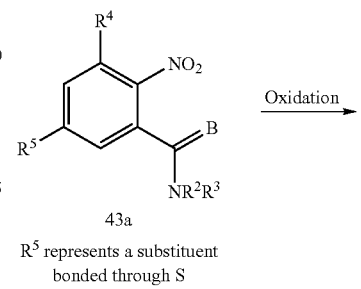

Pyrazolecarboxylic acids of Formula 4f wherein $R^9$ is $CF_3$ can be prepared by the method outlined in Scheme 19.

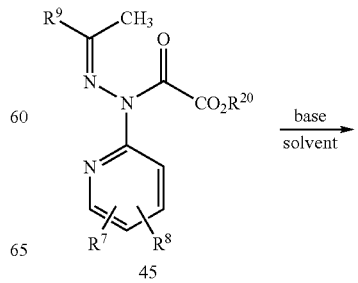

-continued

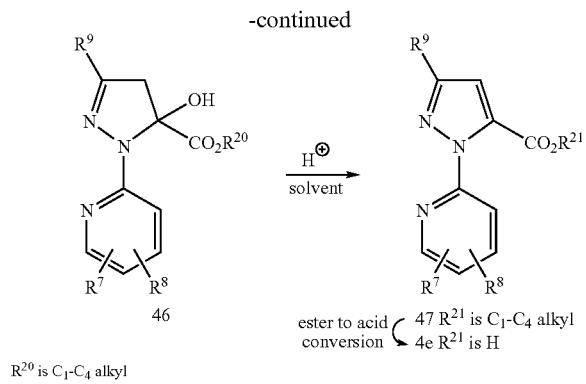

46
$R^{20}$ is $C_1$-$C_4$ alkyl ester to acid conversion  47 $R^{21}$ is $C_1$-$C_4$ alkyl
4e $R^{21}$ is H Reaction of a compound of Formula 45 wherein $R^{20}$ is $C_1$-$C_4$ alkyl with a suitable base in a suitable organic solvent affords the cyclized product of Formula 46 after neutralization with an acid such as acetic acid. The suitable base can be, for example but not limitation, sodium hydride, potassium t-butoxide, dimsyl sodium ($CH_3S(O)CH_2^-Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 46 to give the compound of Formula 47, followed by converting the carboxylic ester function to carboxylic acid, affords the compound of Formula 4f. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C.). For the dehydration in the method of Scheme 19, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For the method of Scheme 19, base-catalyzed hydrolytic methods are preferred. Suitable bases include alkali metal (such as lithium, sodium or potassium) hydroxides. For example, the ester 47 can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 4f. The carboxylic acid can be isolated by methods known to those skilled in the art, including crystallization, extraction and distillation.

Compounds of Formula 45 can be prepared by the method outlined in Scheme 20.

Scheme 20

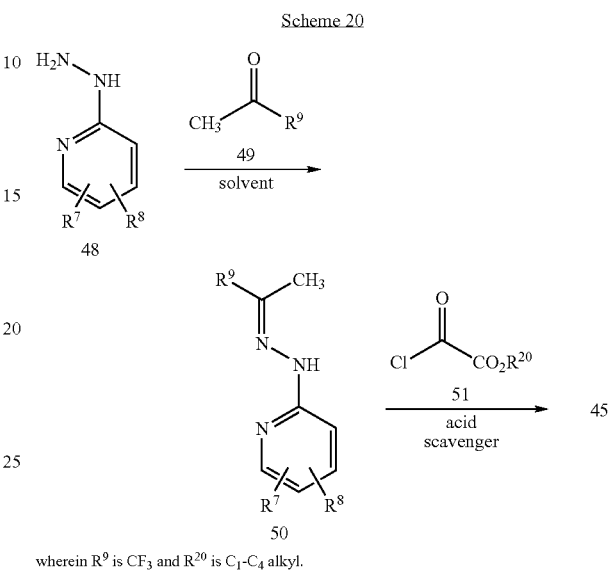

wherein $R^9$ is $CF_3$ and $R^{20}$ is $C_1$-$C_4$ alkyl.

Treatment of a hydrazine compound of Formula 48 with a ketone of Formula 49 in a solvent such as water, methanol or acetic acid gives the hydrazone of Formula 50. One skilled in the art will recognize that this reaction may require catalysis by an optional acid and may also require elevated temperatures depending on the molecular substitution pattern of the hydrazone of Formula 50. Reaction of the hydrazone of Formula 50 with the compound of Formula 51 in a suitable organic solvent such as, for example but not limitation, dichloromethane or tetrahydrofuran in the presence of an acid scavenger such as triethylamine provides the compound of Formula 45. The reaction is usually conducted at a temperature between about 0 and 100° C. Hydrazine compounds of Formula 48 can be prepared by standard methods, such as by contacting the corresponding halo compound of Formula 12 (Scheme 9) with hydrazine.

Pyrazolecarboxylic acids of Formula 4g wherein $R^9$ is Cl or Br can be prepared by the method outlined in Scheme 21.

Scheme 21

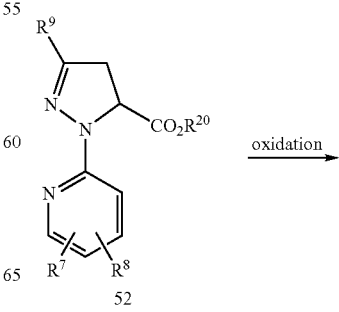

oxidation

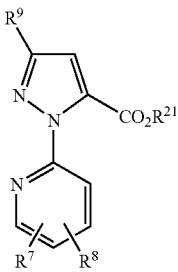

wherein $R^{20}$ is $C_1$-$C_4$ alkyl.

53 $R^{14}$ is $C_1$-$C_4$ alkyl ⎫ ester to acid
4g $R^{14}$ is H ⎭ conversion

Oxidization of the compound of Formula 52 optionally in the presence of acid to give the compound of Formula 53 followed by conversion of the carboxylic ester function to the carboxylic acid provides the compound of Formula 4g. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 52 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 52. To obtain complete conversion, one to five equivalents of acid can be used. The preferred oxidant is potassium persulfate and the oxidation is preferably carried out in the presence of sulfuric acid. The reaction can be carried out by mixing the compound of Formula 52 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 53, can be isolated by methods known to those skilled in the art, including crystallization, extraction and distillation. Methods suitable for converting the ester of Formula 53 to the carboxylic acid of Formula 4g are already described for Scheme 19.

Compounds of Formula 52 can be prepared from corresponding compounds of Formula 54 as shown in Scheme 22.

Scheme 22

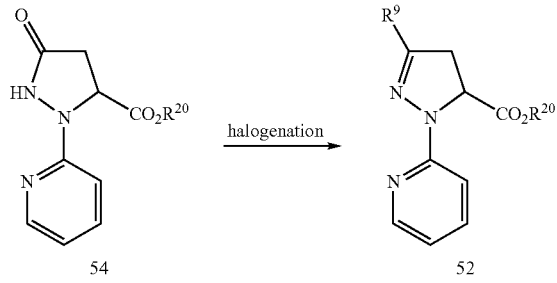

wherein $R^{20}$ is $C_1$-$C_4$ alkyl.

$R^9$ is halogen

Treatment of a compound of Formula 54 with a halogenating reagent, usually in the presence of a solvent, affords the corresponding halo compound of Formula 52. Halogenating reagents that can be used include phosphorus oxyhalides, phosphorus trihalides, phosphorus pentahalides, thionyl chloride, dihalotrialkylphophoranes, dihalodiphenylphosphoranes, oxalkyl chloride and phosgene. Preferred are phosphorus oxyhalides and phosphorus pentahalides. To obtain complete conversion, at least 0.33 equivalents of phosphorus oxyhalide versus the compound of Formula 54 should be used, preferably between about 0.33 and 1.2 equivalents. To obtain complete conversion, at least 0.20 equivalents of phosphorus pentahalide versus the compound of Formula 54 should be used, preferably between about 0.20 and 1.0 equivalents. Compounds of Formula 47 wherein $R^{20}$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 54 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 52, can be isolated by methods known to those skilled in the art, including crystallization, extraction and distillation.

Alternatively, compounds of Formula 52 wherein $R^9$ is Br or Cl can be prepared by treating the corresponding compounds of Formula 52 wherein $R^9$ is a different halogen (e.g., Cl for making Formula 52 wherein $R^9$ is Br) or a sulfonate group such as p-toluenesulfonate with hydrogen bromide or hydrogen chloride, respectively. By this method the $R^9$ halogen or sulfonate substituent on the Formula 52 starting compound is replaced with Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^9$ in the starting compound of Formula 52 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 52 wherein $R^9$ is Br) can facilitate the reaction. The product of Formula 52 is isolated by the usual methods known to those skilled in the art, including extraction, distillation and crystallization.

Starting compounds of Formula 52 wherein $R^9$ is Cl or Br can be prepared from corresponding compounds of Formula 54 as already described. Starting compounds of Formula 52 wherein $R^9$ is a sulfonate group can likewise be prepared from corresponding compounds of Formula 54 by standard methods such as treatment with a sulfonyl chloride (e.g., p-toluenesulfonyl chloride) and base such as a tertiary amine (e.g., triethylamine) in a suitable solvent such as dichloromethane.

Pyrazolecarboxylic acids of Formula 4h wherein $R^9$ is $OCH_2CF_3$ or Formula 4i wherein $R^9$ is $OCHF_2$ can be prepared by the method outlined in Scheme 23. In this method, instead of being halogenated as shown in Scheme 22, the compound of Formula 54 is oxidized to the compound of Formula 55. The reaction conditions for this oxidation are as already described for the conversion of the compound of Formula 52 to the compound of Formula 53 in Scheme 21.

The compound of Formula 55 is then alkylated to form the compound of Formula 57 ($R^9$ is $OCH_2CF_3$) by contact with an alkylating agent $CF_3CH_2Lg$ (56) in the presence of a base. In the alkylating agent 56, Lg is a nucleophilic reaction leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo-[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C.

The compound of Formula 55 can also be alkylated to form the compound of Formula 58 ($R^9$ is $OCHF_2$) by contact with difluorocarbene, prepared from $CHClF_2$ in the presence of a base. The reaction is generally conducted in a solvent, which can comprise ethers, such as tetrahydrofuran or dioxane, and polar aprotic solvents, such as acetonitrile, N,N-dimethylformamide, and the like. The base can be selected from inorganic bases such as potassium carbonate, sodium hydroxide or sodium hydride. Preferably the reaction is conducted using potassium carbonate with N,N-dimethylformamide as the solvent. The product of Formula 57 or 58 can be isolated by conventional techniques such as extraction. The esters can then be converted to the carboxylic acids of Formula 4h or 4i by the methods already described for the conversion of Formula 47 to Formula 4f in Scheme 19.

As outlined in Scheme 24, compounds of Formula 54 can be prepared from compounds of Formula 48 (see Scheme 20).

Scheme 24

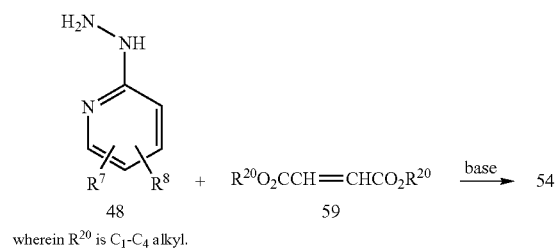

wherein $R^{20}$ is $C_1$-$C_4$ alkyl.

In this method, a hydrazine compound of Formula 48 is contacted with a compound of Formula 59 (a fumarate ester or maleate ester or am mixture thereof may be used) in the presence of a base and a solvent. The base is typically a metal alkoxide salt, such as sodium methoxide, potassium methoxide, sodium ethoxide, potassium ethoxide, potassium tert- Scheme 23

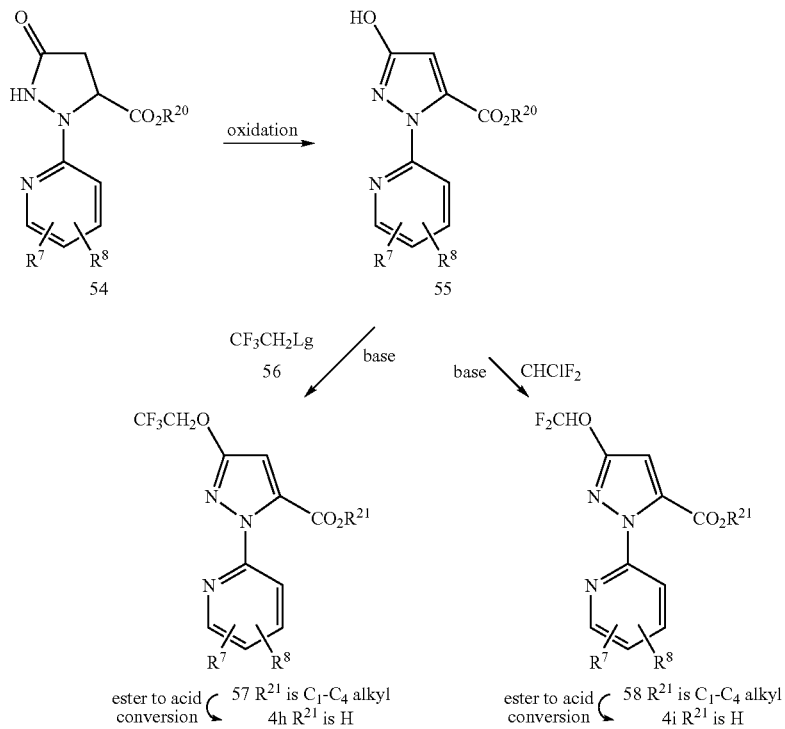

wherein $R^{20}$ is $C_1$-$C_4$ alkyl, and Lg is a leaving group.

butoxide, lithium tert-butoxide, and the like. Greater than 0.5 equivalents of base versus the compound of Formula 59 should be used, preferably between 0.9 and 1.3 equivalents. Greater than 1.0 equivalents of the compound of Formula 59 relative to 48 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 59 and the base in the solvent. The mixture can be heated or cooled to a desired temperature and the compound of Formula 48 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 48 and Formula 59. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^{20}$ function on the compound of Formula 54 may be hydrolyzed to —$CO_2H$; for example, the presence of water in the reaction mixture can promote such hydrolysis. If the carboxylic acid (—$CO_2H$) is formed, it can be converted back to —$CO_2R^{20}$ wherein $R^{20}$ is $C_1$-$C_4$ alkyl using esterification methods well-known in the art. The desired product, a compound of Formula 54, can be isolated by methods known to those skilled in the art, such as crystallization, extraction or distillation.

A general synthesis of pyrrole acids of Formula 4j is depicted in Scheme 25. Treatment of a compound of Formula 60 with 2,5-dimethoxytetrahydrofuran (61) affords a pyrrole of Formula 62. Formylation of the pyrrole 62 to provide the aldehyde of Formula 63 can be accomplished by using standard Vilsmeier-Haack formylation conditions, such as N,N-dimethylformamide (DMF) and phosphorus oxychloride. Halogenation of the compound of Formula 63 with N-halosuccinimides (NXS) such as N-chlorosuccinimide or N-bromosuccinimide occurs preferentially at the 4-position of the pyrrole ring. Oxidation of the halogenated aldehyde affords the pyrrole acid of Formula 4j. The oxidation can be accomplished by using a variety of standard oxidation conditions.

Scheme 25

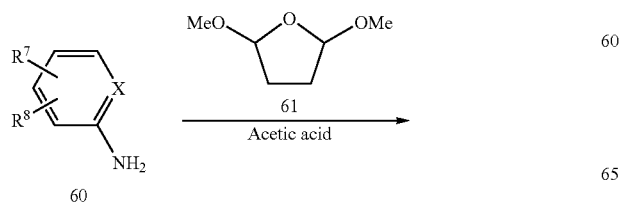

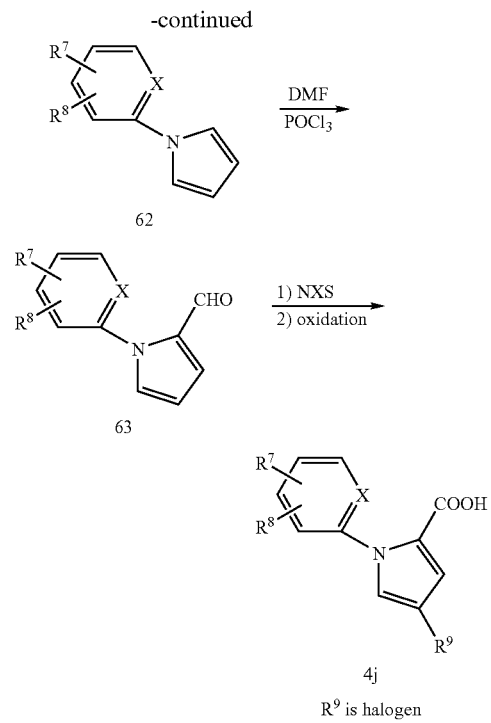

The synthesis of certain pyridinylpyrrole acids of Formula 4k is depicted in Scheme 26. The compound of Formula 65, 3-chloro-2-aminopyridine, is a known compound (see *J. Heterocycl. Chem.* 1987, 24(5), 1313-16). A convenient preparation of 65 from the 2-aminopyridine of Formula 64 involves protection, ortho-metallation, chlorination and subsequent deprotection. The remaining synthesis is conducted according to the general synthesis described in Scheme 25.

Scheme 26

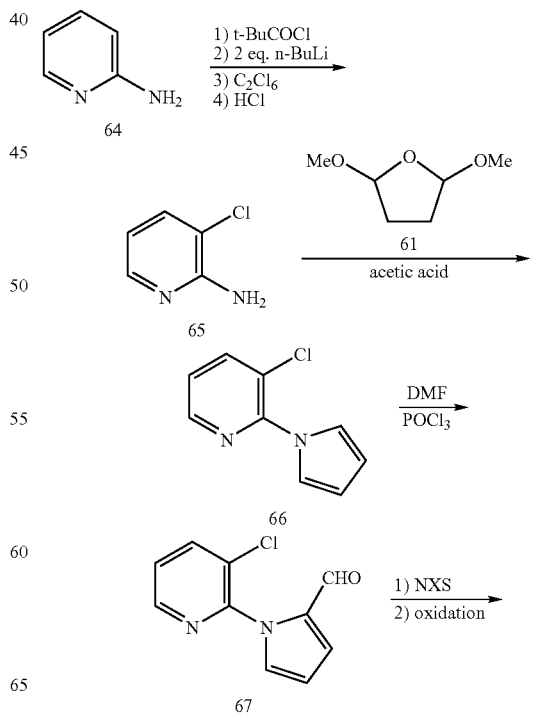

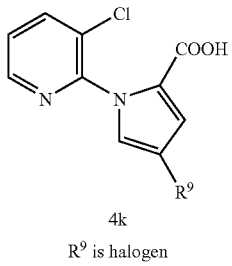

4k

R[9] is halogen

Benzoxazinones of Formula 10 can be prepared by a variety of methods. Two methods that are especially useful are detailed in Schemes 27-28. In Scheme 27, a benzoxazinone of Formula 10 is prepared directly via coupling of a carboxylic acid of Formula 4 with an anthranilic acid of Formula 68.

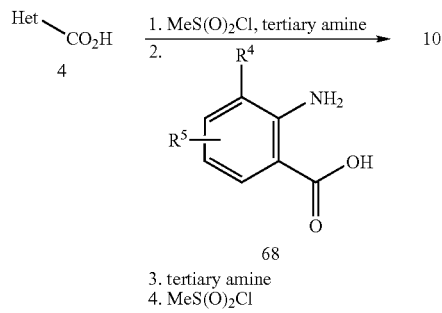

This involves sequential addition of methanesulfonyl chloride in the presence of a tertiary amine such as triethylamine or pyridine to a carboxylic acid of Formula 4, followed by the addition of an anthranilic acid of Formula 68, followed by a second addition of tertiary amine and methanesulfonyl chloride. This method generally affords good yields of the benzoxazinone.

Scheme 28 depicts an alternate preparation for benzoxazinones of Formula 10 involving coupling of an acid chloride of Formula 3 with an isatoic anhydride of Formula 8 to provide the Formula 10 benzoxazinone directly.

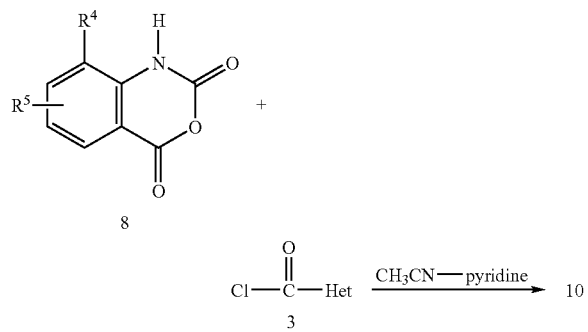

Solvents such as pyridine or pyridine/acetonitrile are suitable for this reaction. As noted above, the acid chlorides of Formula 3 are available from the corresponding acids of Formula 4 by known methods such as chlorination with thionyl chloride or oxalkyl chloride.

Preparation of the isatoic anhydrides of Formula 8 can be achieved from isatins of Formula 70 as outlined in Scheme 29.

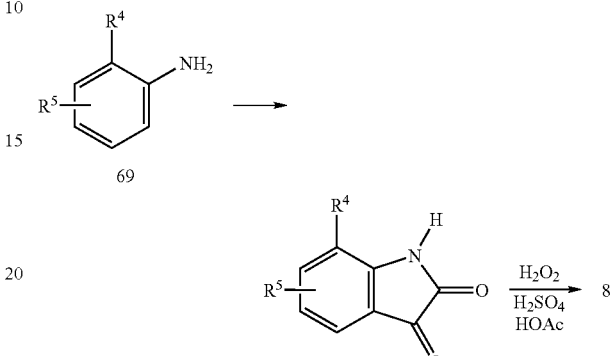

Isatins of Formula 70 are available from aniline derivatives of Formula 69 following literature procedures such as F. D. Popp, *Adv. Heterocycl. Chem.* 1975, 18, 1-58 and J. F. M. Da Silva et al., *Journal of the Brazilian Chemical Society* 2001, 12(3), 273-324. Oxidation of isatin 70 with hydrogen peroxide generally affords good yields of the corresponding isatoic anhydride 8 (G. Reissenweber and D. Mangold, *Angew. Chem. Int. Ed. Engl.* 1980, 19, 222-223). Isatoic anhydrides are also available from the anthranilic acids 68 via many known procedures involving reaction of 68 with phosgene or a phosgene equivalent.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever.

Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s means singlet, d means doublet, t means triplet, q means quartet, m means multiplet, dd means doublet of doublets, dt means doublet of triplets, br s means broad singlet.

EXAMPLE 1

Preparation of 1-[2-(Hydroxymethyl)phenyl]-N-(2-methyl-6-[[(1-methylethyl)amino]carbonyl]phenyl]-3-(trifluoromethyl)-1H-pyrazole-5-carboxamide Step A: Preparation of 1-[2-(methoxycarbonyl)phenyl]-3-(trifluoromethyl)-1H-pyrazole-5-carboxylic acid A solution of 1-[2-(methoxycarbonyl)phenyl]-3-(trifluoromethyl)-1H-pyrazole-5-carboxylic acid (8.0 g, WO 99/32545) in SOCl$_2$ (100 mL) was heated to reflux for 3 hours. The reaction mixture was cooled and concentrated to give the crude acid chloride.

At 0° C., the crude acid chloride in 70 mL of acetone was added dropwise to a solution of 2-amino-3-methylbenzoic acid (4.11 g) and triethylamine (8.24 g) in 400 mL of acetone. The reaction mixture was stirred at 0° C. for 10 minutes and then warmed up to room temperature for 1.5 hours to form the title compound of Step A. The mixture containing this compound was carried directly to Step B.

Step B: Preparation of Methyl 2-[5-[[[2-methyl-6-[[(1-methylethyl)amino]carbonyl]phenyl]amino]carbonyl]-3-(trifluoromethyl)-1H-pyrazol-1-yl]benzoate A solution of iso-butyl chloroformate (3.72 g) in 70 mL of acetone was added dropwise to the reaction mixture from Step A. After 10 minutes, the reaction mixture was concentrated to give an orange oil. Isopropylamine (4.0 g) was added to a solution of the orange oil in 500 mL of acetone at room temperature. After 20 minutes, the reaction mixture was concentrated and then triturated with n-chlorobutane. The white solid was collected via filtration and allowed to air dry to give the title compound (7.0 g).

Step C: Preparation of 1-[2-(Hydroxymethyl)phenyl]-N-(2-methyl-6-[[(1-methylethyl)amino]carbonyl]phenyl-3-(trifluoromethyl)-1H-pyrazole-5-carboxamide To a solution of the ester from Step B (240 mg) in tetrahydrofuran (3 mL) was added a solution of lithium borohydride (2 mL, 2 M in tetrahydrofuran). After being stirred at room temperature overnight, the reaction was quenched with water. The reaction mixture was diluted with 1 N aqueous HCl, extracted with ethyl acetate, washed with brine, dried and concentrated to give a white solid. The solid was washed with ethyl ether (3×2 mL) to give the title compound (96 mg), a product of the present invention.

$^1$H NMR (CDCl$_3$): δ 9.81 (s, 1H), 7.65 (m, 1H), 7.51 (m, 1H), 7.38 (m, 1H), 7.20 (m, 5H), 5.90 (d, J=7.42 Hz, 1H), 4.44 (s, 2H), 4.11 (m, 1H), 3.58 (bs, 1H), 2.15 (s, 3H), 1.22 (d, J=6.9 Hz, 6H).

EXAMPLE 2

Preparation of Methyl 4-[[[1-(3-chloro-2-pyridinyl)-3-(trifluoromethyl)-1H-pyrazol-5-yl]carbonyl]amino]-3-methyl-5-[[(1-methylethyl)amino]carbonyl]benzoate Step A: Preparation of 2-Amino-5-iodo-3-methylbenzoic acid 2-Amino-3-methylbenzoic acid (10 g, 66 mmol) was dissolved in 70 mL of N,N-dimethyl-formamide (DMF) and treated with N-iodosuccinimide (16.4 g, 73 mmol). The mixture was heated at 60° C. for 17 hours and allowed to cool to 25° C. The mixture was diluted with water (150 mL and filtered. The air-dried solid was dissolved in ethyl acetate (200 mL) and dried over magnesium sulfate. Evaporation of the solvent provided the title compound of Step A (7.95 g). $^1$H NMR (CDCl$_3$): δ 7.87 (1H), 7.44 (1H), 2.09 (3H).

Step B: Preparation of 2-[1-(3-Chloro-2-pyridinyl)-3-(trifluoromethyl)-1H-pyrazol-5-yl]-6-iodo-8-methyl-4H-3,1-benzoxazin-4-one To methanesulfonyl chloride (1.64 g, 14.4 mmol) in acetonitrile (20 mL) at −5° C. was added 4 g (14 mmol) of 1-(3-chloro-2-pyridinyl)-3-(trifluoromethyl)-1H-pyrazole-5-carboxylic acid (the title compound from Example 6) and triethylamine (1.39 g, 14 mmol). After five minutes, the title compound of step A (3.8 g, 14 mmol) was added. Ten minutes later triethylamine (1.39 g, 14 mmol) was added. After 20 minutes of continued stirring at 0° C., methanesulfonyl chloride (1.64 g, 14.4 mmol) was added. The mixture was allowed to warm to 25° C. and stirred for 2 hours. The mixture was concentrated under reduced pressure and subjected to chromatography with dichloromethane as eluent. Pooling appropriate fractions and evaporation of solvent provided the title compound of step B (3.07 g). $^1$H NMR (CDCl$_3$): δ 8.6 (1H), 8.36 (1H), 7.98 (1H), 7.86 (1H), 7.58 (1H), 7.49 (1H), 1.79 (1H).

Step C: Preparation of 1-(3-Chloro-2-pyridinyl)-N-[4-iodo-2-methyl-6-[[(1-methylethyl)amino]carbonyl]phenyl]-3-(trifluoromethyl-1H-pyrazole-5-carboxamide The title compound of step B (3.07 g, 5.7 mmol) was dissolved in tetrahydrofuran (30 mL) and treated with isopropylamine (1.69 g, 28.7 mmol). The mixture was heated at 60° C. for 2 hours and concentrated to dryness under reduced pressure. The residue was subjected to chromatography on silica gel using ethyl acetate/hexanes (40:60) as eluent. Pooling appropriate fractions and evaporation of solvent provided the title compound of Step C (2.4 g): m.p.: 199-200° C. $^1$H NMR (CDCl$_3$): δ 10.3 (NH), 8.42 (1H), 7.84 (1H), 7.61 (1H), 7.44 (2H), 7.42 (1H), 6.01 (1H), 4.21 (m, 1H), 2.13 (s, 3H), 1.2 (6H).

Step D: Preparation of Methyl 4-[[[1-(3-chloro-2-pyridinyl)-3-(trifluoromethyl)-1H-pyrazol-5-yl]carbonyl]amino]-3-methyl-5-[[(1-methylethyl)amino]carbonyl]benzoate The title compound of Step C (2.4 g, 4 mmol) was dissolved in dimethyl sulfoxide (30 mL) along with methanol (2 mL) and triethylamine (1 mL). Palladium acetate (0.05 g) and bis(diphenylphosphinopropane) (0.10 g) were added. Carbon monoxide was bubbled through the solution for 5 minutes. The mixture was heated under a balloon of carbon monoxide at 70° C. for 6 hours. The cooled reaction mixture was poured into water (50 mL). The resulting solid was collected by filtration, dissolved in ether and dried over magnesium sulfate. The residue after removal of solvent was subjected to chromatography on silica gel using ethyl acetate/hexanes (30:70) as eluent. Pooling appropriate fractions and evaporation of solvent provided the title compound of step D, a compound of the invention, (1.71 g) m.p. 204-206° C. $^1$H NMR (CDCl$_3$): δ 10.8 (NH), 8.51 (1H), 7.92 (1H), 7.90 (1H), 7.41 (1H), 7.39 (1H), 6.15 (1H), 4.21 (1H), 3.92 (1H), 2.23 (1H), 1.26 (6H).

EXAMPLE 3

Preparation of N-[4-Acetyl-2-methyl-6-[[(1-methylethyl)amino]carbonyl]phenyl]-1-(3-chloro-2-pyridinyl-3-(trifluoromethyl)-1H-pyrazole-5-carboxamide The title compound of Example 2, Step C (0.7 g, 1.3 mmol) was dissolved in DMF (10 mL) and treated with tributyl-(1-ethoxyvinyl)tin (0.47 g, 1.3 mmol) and bis(triphenyl-phosphino)palladium dichloride (50 mg). The mixture was heated at 80° C. for 4 hours. The mixture was poured into water (50 mL) and extracted with ether (3×50 mL). The combined organic layers were washed with water (50 mL) and saturated brine (50 mL). The mixture was dried over magnesium sulfate and concentrated under reduced pressure. The residue was filtered through a silica gel cartridge using dichloromethane as eluent. The appropriate fractions were pooled and evaporated. The residue (400 mg) was dissolved in acetone (20 mL) and treated with 1N hydrochloric acid (5 mL). After 1 hour at 25° C. the reaction mixture was partitioned between ethyl acetate (50 ml) and water (50 ml). The organic layer was dried over magnesium sulfate and concentrated under reduced pressure. The residue was subjected to chromatography on silica gel using ethyl acetate/hexanes (40:60) as eluent. Pooling appropriate fractions and evaporation of solvent provided the title compound, a compound of the invention, (150 mg) as a yellow solid, m.p.: 135-137° C. $^1$H NMR (CDCl$_3$): δ 10.8 (NH), 8.42 (1H), 7.89 (1H), 7.87 (2H), 7.42 (1H), 7.31 (1H), 6.15 (1H), 4.21 (1H), 2.59 (3H), 2.27 (3H), 1.28 (6H).

EXAMPLE 4

Preparation of N-[4-Amino-2-methyl]-6-[[(1-methylethyl)amino]carbonyl]phenyl]-1-(3-chloro-2-pyridinyl)-3-(trifluoromethyl)-1H-pyrazole-5-carboxamide Step A: Preparation of 3-methyl-5-nitro isatoic anhydride Potassium nitrate (1.43 g, 14.1 mmole) was added in small portions at <30° C. with external water-bath cooling to a solution of 3-methyl isatoic anhydride (2.50 g, 14.1 mmole) and concentrated sulfuric acid (8 mL). The resulting mixture was stirred at 25° C. for 1.5 hours and then was poured into approximately 200 g of ice with stirring. After the ice had melted, the solid product was isolated by filtration and washed with dilute aqueous HCl and then air-dried. The product was suspended in acetonitrile (50 mL) and concentrated in vacuo to give 2.75 of a yellow solid. $^1$H NMR (DMSO-d$_6$): δ 11.6 (br s, 1H), 8.45 (d, 1H), 8.42 (d, 1H), 2.43 (s, 3H).

Step B: Preparation of 2-[1-(3-Chloro-2-pyridinyl)-3-(trifluoromethyl)-1H-pyrazol-5-yl]-8-methyl-6-nitro-4H-3,1-benzoxazin-4-one A mixture of 505 mg (1.63 mmol) of the title material from Step A, 344 mg (1.55 mmoles) of 1-(3-chloro-2-pyridinyl)-3-(trifluoromethyl)-1H-pyrazole-5-carbonyl chloride (which can be prepared according to Example 7) and 2 mL of pyridine was heated at 100° C. for 3 hours. The resulting mixture was cooled to 25° C. and partitioned between ethyl acetate and dilute aqueous HCl. The organic layer was washed three times with dilute aqueous HCl, dried over anhydrous magnesium sulfate and concentrated to give a brown solid that was used in the next step without further purification. $^1$H NMR (CDCl$_3$): δ 8.86 (d, 1H), 8.60 (dd, 1H), 8.38 (d, 1H), 8.03 (dd, 1H), 7.59 (s, 1H), 1.95 (s, 3H).

Step C: Preparation of 1-(3-Chloro-2-pyridinyl)-N-[2-methyl-6-[[(1-methylethyl)amino]carbonyl]-4-nitrophenyl]-3-(trifluoromethyl)-1H-pyrazole-5-carboxamide Isopropyl amine (0.35 mL, 4.11 mmol) was added to a solution of 619 mg (1.37 mmol) of the product of Step B in dioxane (8 mL) at 25° C. After being stirred overnight, the resulting heterogenous mixture was concentrated and the residue was triturated with methanol (10 mL). Filtration gave 100 mg of the title product. The filtrate was concentrated and the resulting residue was triturated with diethyl ether. Filtration of the resulting solid provided an additional 320 mg of the title product, m.p. 170-172° C.

Step D: Preparation of N-[4-Amino-2-methyl-6-[[(1-methylethyl)amino]carbonyl]phenyl]-1-(3-chloro-2-pyridinyl)-3-(trifluoromethyl)-1H-pyrazole-5-carboxamide Zinc dust (90 mg, 1.4 mmol) was added to a solution of the product from Step C (70 mg, 0.14 mmole) and trifluoroacetic acid (2 mL) at 70° C. Some foaming occurred. After 10 minutes at 70° C., the mixture was cooled to 25° C., diluted with dichloromethane, and filtered. The filtrate was concentrated to remove most of the trifluoroacetic acid and the resulting residue was dissolved in acetonitrile (3 mL) and 1,2-dichloroethane (3 mL). The resulting solution was treated with strongly-basic ion exchange resin (Dowex® 550A, OH$^-$ form, 2 g), shaken for 1 hour and then filtered. Concentration of the filtrate gave the title compound, a compound of the invention, as a yellow solid.

$^1$H NMR (CDCl$_3$): δ 9.80 (br s, 1H), 8.50 (dd, 1H), 7.82 (dd, 1H), 7.42 (s, 1H), 7.39 (m, 1H), 6.50 (br d, 2H), 6.02 (m, 1H), 2.10 (s, 3H), 1.11 (d, 6H).

EXAMPLE 5

Preparation of N-[4-Benzoylamino-2-methyl-6-[[(1-methylethyl)amino]carbonyl]phenyl]-1-(3-chloro-2-pyridinyl)-3-(trifluoromethyl)-1H-pyrazole-5-carboxamide A solution of the title product of Example 4 (100 mg, 0.21 mmol), benzoic anhydride (52 mg, 0.23 mmol) and DMF (2 mL) was stirred at 25° C. overnight. The resulting mixture was concentrated in vacuo, and the resulting crude product was triturated with diethyl ether and filtered to give 92 mg of the title material a compound of the invention, as a solid.

¹H NMR (DMSO-d₆): δ 10.36 (s, 1H), 10.22 (s, <1H), 8.56 (d, 1H), 8.21 (d, 1H), 7.98-7.92 (m, 3H), 7.82 (distorted s, 1H), 7.78 (s, 1H), 7.70-7.50 (m, 5H), 3.93 (septet, 1H), 2.18 (s, 1H), 1.03 (d, 6H).

EXAMPLE 6

Step A: Preparation of 3-Chloro-2(1H)-pyridinone (2,2,2-trifluoro-1-methylethylidene)hydrazone 1,1,1-Trifluoroacetone (7.80 g, 69.6 mmol) was added to (3-chloro-pyridin-2-yl)-hydrazine (10 g, 69.7 mmol) at 20-25° C. After the addition was complete, the mixture was stirred for about 10 minutes. The solvent was removed under reduced pressure, and the mixture was partitioned between ethyl acetate (100 mL) and saturated sodium carbonate solution (100 mL). The organic layer was dried and evaporated. Chromatography on silica gel (eluted with ethyl acetate) gave the product as an off-white solid (11 g, 66% yield), m.p. 64-64.5° C. (after crystallization from ethyl acetate/hexanes).

IR (nujol) ν 1629, 1590, 1518, 1403, 1365, 1309, 1240, 1196, 1158, 1100, 1032, 992, 800 cm⁻¹. ¹H NMR (CDCl₃) δ 2.12 (s, 3H), 6.91-6.96 (m, 1H), 7.64-7.61 (m, 1H), 8.33-8.32 (m, 2H). MS m/z 237 (M⁺).

Step B: Preparation of Ethyl hydrogen ethanedioate (3-chloro-2-pyridinyl) (2,2,2-trifluoro-1-methylethylidene)hydrazide Triethylamine (20.81 g, 0.206 mol) was added to 3-chloro-2(1H)-pyridinone (2,2,2-trifluoro-1-methylethylidene)hydrazone (i.e. the product of Step A) (32.63 g, 0.137 mol) in dichloromethane (68 mL) at 0° C. Ethyl chlorooxoacetate (18.75 g, 0.137 mol) in dichloromethane (69 mL) was added dropwise to the mixture at 0° C. The mixture was allowed to warm to 25° C. over about 2 hours. The mixture was cooled to 0° C. and a further portion of ethyl chlorooxoacetate (3.75 g, 27.47 mmol) in dichloromethane (14 mL) was added dropwise. After about an additional 1 hour, the mixture was diluted with dichloromethane (about 450 mL), and the mixture was washed with water (2×150 mL). The organic layer was dried and evaporated. Chromatography on silica gel (eluted with 1:1 ethyl acetate-hexanes) gave the product as a solid (42.06 g, 90% yield), m.p. 73.0-73.5° C. (after crystallization from ethyl acetate/hexanes).

IR (nujol) ν 1751, 1720, 1664, 1572, 1417, 1361, 1330, 1202, 1214, 1184, 1137, 1110, 1004, 1043, 1013, 942, 807, 836 cm⁻¹. ¹H NMR (DMSO-d₆, 115° C.) δ 1.19 (t, 3H), 1.72 (br s, 3H), 4.25 (q, 2H), 7.65 (dd, J=8.3, 4.7 Hz, 1H), 8.20 (dd, J=7.6, 1.5 Hz, 1H), 8.55 (d, J=3.6 Hz, 1H). MS m/z 337 (M⁺).

Step C: Preparation of Ethyl 1-(3-chloro-2-pyridinyl)-4,5-dihydro-5-hydroxy-3-(trifluoromethyl)-1H-pyrazole-5-carboxylate Ethyl hydrogen ethanedioate (3-chloro-2-pyridinyl) (2,2,2-trifluoro-1-methyl-ethylidene)hydrazide (i.e. the product of Step B) (5 g, 14.8 mmol) in dimethyl sulfoxide (25 mL) was added to tetrabutylammonium fluoride hydrate (10 g) in dimethyl sulfoxide (25 mL) over 8 hours. When the addition was complete, the mixture was poured into a mixture of acetic acid (3.25 g) and water (25 mL). After stirring at 25° C. overnight, the mixture was then extracted with toluene (4×25 mL), and the combined toluene extracts were washed with water (50 mL), dried and evaporated to give a solid. Chromatography on silica gel (eluted with 1:2 ethyl acetate-hexanes) gave the product as a solid (2.91 g, 50% yield, containing about 5% of 3-chloro-2(1H)-pyridinone (2,2,2-trifluoro-1-methylethylidene)hydrazone), m.p. 78-78.5° C. (after recrystallization from ethyl acetate/hexanes).

IR (nujol) ν 3403, 1726, 1618, 1582, 1407, 1320, 1293, 1260, 1217, 1187, 1150, 1122, 1100, 1067, 1013, 873, 829 cm⁻¹. ¹H NMR (CDCl₃) δ 1.19 (s, 3H), 3.20 (½ of ABZ pattern, J=18 Hz, 1H), 3.42 (½ of ABZ pattern, J=18 Hz, 1H), 4.24 (q, 2H), 6.94 (dd, J=7.9, 4.9 Hz, 1H), 7.74 (dd, J=7.7, 1.5 Hz, 1H, 8.03 (dd, J=4.7, 1.5 Hz, 1H). MS m/z 319 (M⁺).

Step D: Preparation of Ethyl 1-(3-chloro-2-pyridinyl)-3-(trifluoromethyl)-1H-pyrazole-5-carboxylate Sulfuric acid (concentrated, 2 drops) was added to ethyl 1-(3-chloro-2-pyridinyl)-4,5-dihydro-5-hydroxy-3-(trifluoromethyl)-1H-pyrazole-5-carboxylate (i.e. the product of Step C) (1 g, 2.96 mmol) in acetic acid (10 mL) and the mixture was warmed to 65° C. for about 1 hour. The mixture was allowed to cool to 25° C. and most of the acetic acid was removed under reduced pressure. The mixture was partitioned between saturated aqueous sodium carbonate solution (100 mL) and ethyl acetate (100 mL). The aqueous layer was further extracted with ethyl acetate (100 mL). The combined organic extracts were dried and evaporated to give the product as an oil (0.66 g, 77% yield).

IR (neat) ν 3147, 2986, 1734, 1577, 1547, 1466, 1420, 1367, 1277, 1236, 1135, 1082, 1031, 973, 842, 802 cm⁻¹. ¹H NMR (CDCl₃) δ 1.23 (t, 3H), 4.25 (q, 2H), 7.21 (s, 1H), 7.48 (dd, J=8.1, 4.7 Hz, 1H), 7.94 (dd, J=6.6, 2 Hz, 1H), 8.53 (dd, J=4.7, 1.5 Hz, 1H). MS m/z 319 (M⁺).

Step E: Preparation of 1-(3-chloro-2-pyridinyl)-3-(trifluoromethyl)-1H-pyrazole-5-carboxylic acid Potassium hydroxide (0.5 g, 85%, 2.28 mmol) in water (1 mL) was added to ethyl 1-(3-chloro-2-pyridinyl)-3-(trifluoromethyl)-1H-pyrazole-5-carboxylate (i.e. the product of Step D) (0.66 g, 2.07 mmol) in ethanol (3 mL). After about 30 minutes, the solvent was removed under reduced pressure, and the mixture was dissolved in water (40 mL). The solution was washed with ethyl acetate (20 mL). The aqueous layer was acidified with concentrated hydrochloric acid and was extracted with ethyl acetate (3×20 mL). The combined extracts were dried and evaporated to give the product as a solid (0.53 g, 93% yield), m.p. 178-179° C. (after crystallization from hexanes-ethyl acetate).

IR (nujol) ν 1711, 1586, 1565, 1550, 1440, 1425, 1292, 1247, 1219, 1170, 1135, 1087, 1059, 1031, 972, 843, 816 cm⁻¹. ¹H NMR (DMSO-d₆) δ 7.61 (s, 1H), 7.77 (m, 1H), 8.30 (d, 1H), 8.60 (s, 1H).

EXAMPLE 7

Preparation of 1-(3-chloro-2-pyridinyl)-3-(trifluoromethyl-1H-pyrazole-5-carbonyl chloride To a solution of 268 mg (0.92 mmol) of 1-(3-chloro-2-pyridinyl)-3-(trifluoromethyl)-1H-pyrazole-5-carboxylic acid (which can be prepared according to Example 6) in 5 mL of dichloromethane was added 160 μL (1.84 mmol) of oxalkyl chloride and two drops of DMF in sequence at room temperature. The mixture was then stirred at the same temperature for about 1 hour. The crude mixture was then concentrated in vacuo. The title material is typically used without additional purification or characterization.

By the procedures described herein together with methods known in the art, the following compounds of Tables 1 to 5 can be prepared. The following abbreviations are used in the Tables: t means tertiary, s means secondary, n means normal, i means iso, c means cyclo, Me means methyl, Et means ethyl, Pr means propyl, Bu means butyl, i-Pr means isopropyl, t-Bu means tert butyl, Ph means phenyl, OMe means methoxy, EtO or OEt means ethoxy, SMe means methylthio, SEt means ethylthio, CN means cyano, NO₂ means nitro, MeSOMe means methylsulfinyl, and MeSO₂Me means methylsulfonyl.

TABLE 1

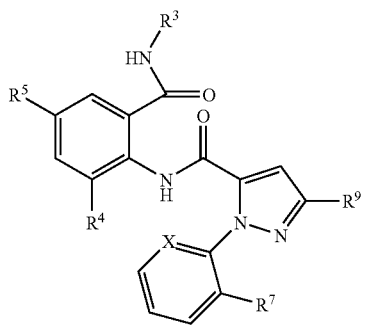

R³ is i-Pr, R⁴ is Me, X is N, R⁷ is Cl, R⁹ is CF₃ and R⁵ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCO | CSNH₂ | S-2-Oxazolyl | O-Propargyl |
| MeCONH | CSNHMe | S-6-Cl-3-Pyridazinyl | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

R³ is Me, R⁴ is M; X is N, R⁷ is Cl, R⁹ is CF₃ and R⁵ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | 5-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCO | CSNH₂ | S-2-Oxazolyl | O-Propargyl |
| MeCONH | CSNHMe | S-6-Cl-3-Pyridazinyl | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

R³ is i-Pr, R⁴ is Cl, X is N, R⁷ is Cl, R⁹ is CF₃ and R⁵ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |

TABLE 1-continued

[Structure: benzamide with R5, R4 substituents, HN-R3 carboxamide, connected via NH to pyrazole-5-carboxamide with R9, N-substituted with phenyl bearing X and R7]

| | | | |
|---|---|---|---|
| MeCO | CSNH₂ | S-2-Oxazolyl | O-Propargyl |
| MeCONH | CSNHMe | S-6-Cl-3-Pyridazinyl) | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

$R^3$ is Me, $R^4$ is Me, X is CH, $R^7$ is Cl, $R^9$ is CF₃ and $R^5$ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCO | CSNH₂ | S-2-Oxazolyl | O-Propargyl |
| MeCONH | CSNHMe | S-6-Cl-3-Pyridazinyl) | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

$R^3$ is i-Pr, $R^4$ is Me, X is N, $R^7$ is Cl, $R^9$ is Cl and $R^5$ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyzidinyl | S-4-Pyridinyl | OCH(Me)CN |
| SF₅ | O-2-Thiazolyl | S-2-Thiazolyl | OCH₂CH=CH₂ |
| MeCO | CSNH₂ | S-2-Oxazolyl | O-Propargyl |
| MeCONH | CSNHMe | S-6-Cl-3-Pyridazinyl) | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |

TABLE 1-continued

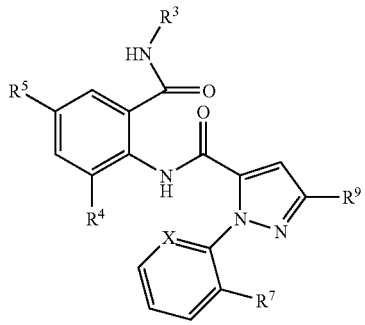

| | | | |
|---|---|---|---|
| 4-Pyrimidinyl | CH$_2$CN | CH$_2$SiMe$_3$ | OCH$_2$OCH$_2$CF$_3$ |
| 2-Pyridinyl | CH$_2$OCH$_2$OCH$_3$ | S-(4-ClPh) | OCH$_2$SiMe$_3$ |
| 3-Pyridinyl | CH$_2$OCH$_2$CF$_3$ | SCH$_2$CH=CH$_2$ | OCONHMe |
| 4-Pyridinyl | CH$_2$SMe | S-Propargyl | OCONMe$_2$ |
| 2-Thiazolyl | CH$_2$SCF$_3$ | S-c-Pr | OSO$_2$NMe$_2$ |
| 2-Oxazolyl | CH$_2$SEt | SCH$_2$CN | O-2-Oxazolyl |
| 1-Morpholinyl | O-2-Pyrazinyl | SCONMe$_2$ | O-6-Cl-3-Pyridazinyl |
| CO$_2$Me | CONHMe | PhSO$_2$ | Me$_2$NCONH |
| CO$_2$Et | CONH-i-Pr | COPh | PhCONH |
| CO$_2$CH$_2$CF$_3$ | CONHPh | COCF$_3$ | F$_3$CCONH |
| COSMe | CONMe$_2$ | C(=NOH)Me | C(=NOMe)Me |

R$^3$ is Me, R$^4$ is Me, X is N, R$^7$ is Cl, R$^9$ is Cl and R$^5$ is selected from

| | | | |
|---|---|---|---|
| B(OH)$_2$ | O-2-Pyrimidinyl | S-2-Pyrimidinyl | OSO$_2$Me |
| SH | O-4-Pyrimidinyl | S-4-Pyrimidinyl | OSO$_2$CF$_3$ |
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$OH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$OH=CH$_2$ |
| MeCO | CSNH$_2$ | S-2-Oxazolyl | O-Propargyl |
| MeCONH | CSNHMe | S-6-Cl-3-Pyridazinyl) | OCH$_2$C(Cl)=CH$_2$ |
| MeOCONH | CH$_2$OH | S-2-Pyrazinyl | OCH$_2$CH=O(Cl)$_2$ |
| MeNHCONH | CH$_2$NHCOMe | SPh | O-c-Pr |
| (EtO)$_2$PO | CH$_2$NHCO$_2$Me | CH$_2$OMe | O-c-Pentyl |
| MeSO$_2$ | CH$_2$NHCOCF$_3$ | CH$_2$OEt | OCH$_2$-c-Pr |
| MeSO$_2$NH | CH$_2$NHSO$_2$Me | CH$_2$O-i-Pr | OCH$_2$CO$_2$Me |
| 2-Pyrimidinyl | CH$_2$NHSO$_2$NMe$_2$ | CH$_2$NMe$_2$ | OCH$_2$OMe |
| 4-Pyrimidinyl | CH$_2$CN | CH$_2$SiMe$_3$ | OCH$_2$OCH$_2$CF$_3$ |
| 2-Pyridinyl | CH$_2$OCH$_2$OCH$_3$ | S-(4-ClPh) | OCH$_2$SiMe$_3$ |
| 3-Pyridinyl | CH$_2$OCH$_2$CF$_3$ | SCH$_2$CH=CH$_2$ | OCONHMe |
| 4-Pyridinyl | CH$_2$SMe | S-Propargyl | OCONMe$_2$ |
| 2-Thiazolyl | CH$_2$SCF$_3$ | S-c-Pr | OSO$_2$NMe$_2$ |
| 2-Oxazolyl | CH$_2$SEt | SCH$_2$CN | O-2-Oxazolyl |
| 1-Morpholinyl | O-2-Pyrazinyl | SCONMe$_2$ | O-6-Cl-3-Pyridazinyl |
| CO$_2$Me | CONHMe | PhSO$_2$ | Me$_2$NCONH |
| CO$_2$Et | CONH-i-Pr | COPh | PhCONH |
| CO$_2$CH$_2$CF$_3$ | CONHPh | COCF$_3$ | F$_3$CCONH |
| COSMe | CONMe$_2$ | C(=NOH)Me | C(=NOMe)Me |

R$^3$ is Me, R$^4$ is Cl, X is N, R$^7$ is Cl, R$^9$ is Cl and R$^5$ is selected from

| | | | |
|---|---|---|---|
| B(OH)$_2$ | O-2-Pyrimidinyl | S-2-Pyrimidinyl | OSO$_2$Me |
| SH | O-4-Pyrimidinyl | S-4-Pyrimidinyl | OSO$_2$CF$_3$ |
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$OH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$CH=CH$_2$ |
| MeCO | CSNH$_2$ | S-2-Oxazolyl | O-Propargyl |
| MeCONH | CSNHMe | S-6-Cl-3-Pyridazinyl) | OCH$_2$C(Cl)=CH$_2$ |
| MeOCONH | CH$_2$OH | S-2-Pyrazinyl | OCH$_2$CH=C(Cl)$_2$ |
| MeNHCONH | CH$_2$NHCOMe | SPh | O-c-Pr |
| (EtO)$_2$PO | CH$_2$NHCO$_2$Me | CH$_2$OMe | O-c-Pentyl |
| MeSO$_2$ | CH$_2$NHCOCF$_3$ | CH$_2$OEt | OCH$_2$-c-Pr |
| MeSO$_2$NH | CH$_2$NHSO$_2$Me | CH$_2$O-i-Pr | OCH$_2$CO$_2$Me |
| 2-Pyrimidinyl | CH$_2$NHSO$_2$NMe$_2$ | CH$_2$NMe$_2$ | OCH$_2$OMe |
| 4-Pyrimidinyl | CH$_2$CN | CH$_2$SiMe$_3$ | OCH$_2$OCH$_2$CF$_3$ |
| 2-Pyridinyl | CH$_2$OCH$_2$OCH$_3$ | S-(4-ClPh) | OCH$_2$SiMe$_3$ |
| 3-Pyridinyl | CH$_2$OCH$_2$CF$_3$ | SCH$_2$CH=CH$_2$ | OCONHMe |
| 4-Pyridinyl | CH$_2$SMe | S-Propargyl | OCONMe$_2$ |
| 2-Thiazolyl | CH$_2$SCF$_3$ | S-c-Pr | OSO$_2$NMe$_2$ |
| 2-Oxazolyl | CH$_2$SEt | SCH$_2$CN | O-2-Oxazolyl |
| 1-Morpholinyl | O-2-Pyrazinyl | SCONMe$_2$ | O-6-Cl-3-Pyridazinyl |
| CO$_2$Me | CONHMe | PhSO$_2$ | Me$_2$NCONH |

TABLE 1-continued

[Structure diagram: benzamide core with R³HN-C(=O)- and -C(=O)-NH- linked to pyrazole bearing R⁹, with N-aryl group having X and R⁷ substituents; R⁴ and R⁵ on the benzene ring]

| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

R³ is i-Pr, R⁴ is Me, X is N, R⁷ is Cl, R⁹ is Br and R⁵ is selected from

| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCO | CSNH₂ | S-2-Oxazolyl | O-Propargyl |
| MeCONH | CSNHMe | S-6-Cl-3-Pyridazinyl) | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CHNMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

R³ is Me, R⁴ is Me, X is N, R⁷ is Cl, R⁹ is Br and R⁵ is selected from

| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CHCH₂ |
| MeCO | CSNH₂ | S-2-Oxazolyl | O-Propargyl |
| MeCONH | CSNHMe | S-6-Cl-3-Pyridazinyl) | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

R³ is Me, R⁴ is Cl, X is N, R⁷ is Cl, R⁹ is Br and R⁵ is selected from

| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |

TABLE 1-continued

| | | | |
|---|---|---|---|
| OSiMe₃ | O-(5-Cl-2-Pyridmyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CHCH₂ |
| MeCO | CSNH₂ | S-2-Oxazolyl | O-Propargyl |
| MeCONH | CSNHMe | S-6-Cl-3-Pyridazinyl | OCH₂C(Cl)=CH₂ |
| MeOCONH | CH₂OH | S-2-Pyrazinyl | OCH₂CH=C(Cl)₂ |
| MeNHCONH | CH₂NHCOMe | SPh | O-c-Pr |
| (EtO)₂PO | CH₂NHCO₂Me | CH₂OMe | O-c-Pentyl |
| MeSO₂ | CH₂NHCOCF₃ | CH₂OEt | OCH₂-c-Pr |
| MeSO₂NH | CH₂NHSO₂Me | CH₂O-i-Pr | OCH₂CO₂Me |
| 2-Pyrimidinyl | CH₂NHSO₂NMe₂ | CH₂NMe₂ | OCH₂OMe |
| 4-Pyrimidinyl | CH₂CN | CH₂SiMe₃ | OCH₂OCH₂CF₃ |
| 2-Pyridinyl | CH₂OCH₂OCH₃ | S-(4-ClPh) | OCH₂SiMe₃ |
| 3-Pyridinyl | CH₂OCH₂CF₃ | SCH₂CH=CH₂ | OCONHMe |
| 4-Pyridinyl | CH₂SMe | S-Propargyl | OCONMe₂ |
| 2-Thiazolyl | CH₂SCF₃ | S-c-Pr | OSO₂NMe₂ |
| 2-Oxazolyl | CH₂SEt | SCH₂CN | O-2-Oxazolyl |
| 1-Morpholinyl | O-2-Pyrazinyl | SCONMe₂ | O-6-Cl-3-Pyridazinyl |
| CO₂Me | CONHMe | PhSO₂ | Me₂NCONH |
| CO₂Et | CONH-i-Pr | COPh | PhCONH |
| CO₂CH₂CF₃ | CONHPh | COCF₃ | F₃CCONH |
| COSMe | CONMe₂ | C(=NOH)Me | C(=NOMe)Me |

TABLE 2

R³ is i-Pr, R⁴ is Me, X is N, R⁵ is Cl, R⁹ is CF₃ and R⁸ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCONH | CSNH₂ | S-2-Oxazolyl | O-Propargyl |
| MeOCONH | CSNHMe | S-6-Cl-3-Pyridazinyl | OCH₂C(Cl)=CH₂ |
| MeNHCONH | CH₂OH | S-2-Pyrazinyl | OCH₂CH=C(Cl)₂ |
| (EtO)₂PO | CH₂NHCOMe | SPh | O-c-Pr |
| MeSO₂ | CH₂NHCO₂Me | CH₂OMe | O-c-Pentyl |
| MeSO₂NH | CH₂NHCOCF₃ | CH₂OEt | OCH₂-c-Pr |
| 2-Pyrimidinyl | CH₂NHSO₂Me | CH₂O-i-Pr | OCH₂CO₂Me |
| 4-Pyrimidinyl | CH₂NHSO₂NMe₂ | CH₂NMe₂ | OCH₂OMe |
| 2-Pyridinyl | CH₂CN | CH₂SiMe₃ | OCH₂OCH₂CF₃ |
| 3-Pyridinyl | CH₂OCH₂OCH₃ | S-(4-ClPh) | OCH₂SiMe₃ |
| 4-Pyridinyl | CH₂OCH₂CF₃ | SCH₂CH=CH₂ | OCONHMe |

TABLE 2-continued

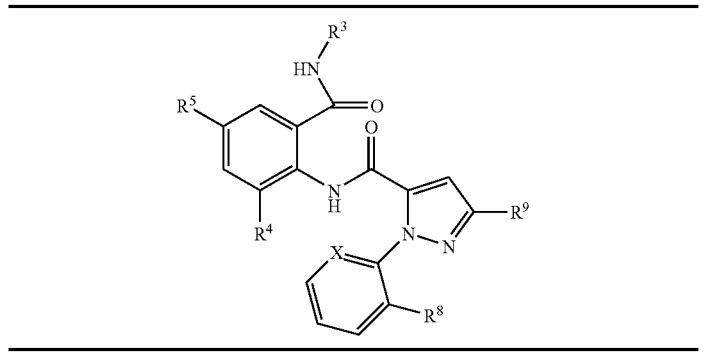

| | | | |
|---|---|---|---|
| 2-Thiazolyl | $CH_2SMe$ | S-Propargyl | $OCONMe_2$ |
| 2-Oxazolyl | $CH_2SCF_3$ | S-c-Pr | $OSO_2NMe_2$ |
| 1-Morpholinyl | $CH_2SEt$ | $SCH_2CN$ | O-2-Oxazolyl |
| $CO_2CH_2CF_3$ | O-2-Pyrazinyl | $SCONMe_2$ | O-6-Cl-3-Pyridazinyl |
| COSMe | $F_3CCONH$ | $PhSO_2$ | $Me_2NCONH$ |
| $COCF_3$ | C(=NOMe)Me | COPh | PhCONH |
| C(=NOH)Me | | | |

$R^3$ is Me, $R^4$ is Me, X is N, $R^5$ is Cl, $R^9$ is $CF_3$ and $R^8$ is selected from

| | | | |
|---|---|---|---|
| $B(OH)_2$ | O-2-Pyrimidinyl | S-2-Pyrimidinyl | $OSO_2Me$ |
| SH | O-4-Pyrimidinyl | S-4-Pyrimidinyl | $OSO_2CF_3$ |
| SCN | O-2-Pyridinyl | S-2-Pyridinyl | $OCH_2CN$ |
| $OSiMe_3$ | O-(5-Cl-2-Pyridinyl) | S-(5-Cl-2-Pyridinyl) | $OCH_2CH_2CN$ |
| SSMe | O-4-Pyridinyl | S-4-Pyridinyl | OCH(Me)CN |
| $SF_5$ | O-2-Thiazolyl | S-2-Thiazolyl | $OCH_2CH=CH_2$ |
| MeCONH | $CSNH_2$ | S-2-Oxazolyl | O-Propargyl |
| MeOCONH | CSNHMe | S-6-Cl-3-Pyridazinyl) | $OCH_2C(Cl)=CH_2$ |
| MeNHCONH | $CH_2OH$ | S-2-Pyrazinyl | $OCH_2CH=C(Cl)_2$ |
| $(EtO)_2PO$ | $CH_2NHCOMe$ | SPh | O-c-Pr |
| $MeSO_2$ | $CH_2NHCO_2Me$ | $CH_2OMe$ | O-c-Pentyl |
| $MeSO_2NH$ | $CH_2NHCOCF_3$ | $CH_2OEt$ | $OCH_2$-c-Pr |
| 2-Pyrimidinyl | $CH_2NHSO_2Me$ | $CH_2O$-i-Pr | $OCH_2CO_2Me$ |
| 4-Pyrimidinyl | $CH_2NHSO_2NMe_2$ | $CH_2NMe_2$ | $OCH_2OMe$ |
| 2-Pyridinyl | $CH_2CN$ | $CH_2SiMe_3$ | $OCH_2OCH_2CF_3$ |
| 3-Pyridinyl | $CH_2OCH_2OCH_3$ | S-(4-ClPh) | $OCH_2SiMe_3$ |
| 4-Pyridinyl | $CH_2OCH_2CF_3$ | $SCH_2CH=CH_2$ | OCONHMe |
| 2-Thiazolyl | $CH_2SMe$ | S-Propargyl | $OCONMe_2$ |
| 2-Oxazolyl | $CH_2SCF_3$ | S-c-Pr | $OSO_2NMe_2$ |
| 1-Morpholinyl | $CH_2SEt$ | $SCH_2CN$ | O-2-Oxazolyl |
| $CO_2CH_2CF_3$ | O-2-Pyrazinyl | $SCONMe_2$ | O-6-Cl-3-Pyridazinyl |
| COSMe | $F_3CCONH$ | $PhSO_2$ | $Me_2NCONH$ |
| $COCF_3$ | C(=NOMe)Me | COPh | PhCONH |
| C(=NOH)Me | | | |

$R^3$ is i-Pr, $R^4$ is Cl, X is N, $R^5$ is Cl, $R^9$ is $CF_3$ and $R^8$ is selected from

| | | | |
|---|---|---|---|
| $B(OH)_2$ | O-2-Pyrimidinyl | S-2-Pyrimidinyl | $OSO_2Me$ |
| SH | O-4-Pyrimidinyl | S-4-Pyrimidinyl | $OSO_2CF_3$ |
| SCN | O-2-Pyridinyl | S-2-Pyridinyl | $OCH_2CN$ |
| $OSiMe_3$ | O-(5-Cl-2-Pyridinyl) | S-(5-Cl-2-Pyridinyl) | $OCH_2CH_2CN$ |
| SSMe | O-4-Pyridinyl | S-4-Pyridinyl | OCH(Me)CN |
| $SF_5$ | O-2-Thiazolyl | S-2-Thiazolyl | $OCH_2CH=CH_2$ |
| MeCONH | $CSNH_2$ | S-2-Oxazolyl | O-Propargyl |
| MeOCONH | CSNHMe | S-6-Cl-3-Pyridazinyl) | $OCH_2C(Cl)=CH_2$ |
| MeNHCONH | $CH_2OH$ | S-2-Pyrazinyl | $OCH_2CH=C(Cl)_2$ |
| $(EtO)_2PO$ | $CH_2NHCOMe$ | SPh | O-c-Pr |
| $MeSO_2$ | $CH_2NHCO_2Me$ | $CH_2OMe$ | O-c-Pentyl |
| $MeSO_2NH$ | $CH_2NHCOCF_3$ | $CH_2OEt$ | $OCH_2$-c-Pr |
| 2-Pyrimidinyl | $CH_2NHSO_2Me$ | $CH_2O$-i-Pr | $OCH_2CO_2Me$ |
| 4-Pyrimidinyl | $CH_2NHSO_2NMe_2$ | $CH_2NMe_2$ | $OCH_2OMe$ |
| 2-Pyridinyl | $CH_2CN$ | $CH_2SiMe_3$ | $OCH_2OCH_2CF_3$ |
| 3-Pyridinyl | $CH_2OCH_2OCH_3$ | S-(4-ClPh) | $OCH_2SiMe_3$ |
| 4-Pyridinyl | $CH_2OCH_2CF_3$ | $SCH_2CH=CH_2$ | OCONHMe |
| 2-Thiazolyl | $CH_2SMe$ | S-Propargyl | $OCONMe_2$ |
| 2-Oxazolyl | $CH_2SCF_3$ | S-c-Pr | $OSO_2NMe_2$ |
| 1-Morpholinyl | $CH_2SEt$ | $SCH_2CN$ | O-2-Oxazolyl |
| $CO_2CH_2CF_3$ | O-2-Pyrazinyl | $SCONMe_2$ | O-6-Cl-3-Pyridazinyl |
| COSMe | $F_3CCONH$ | $PhSO_2$ | $Me_2NCONH$ |
| $COCF_3$ | C(=NOMe)Me | COPh | PhCONH |
| C(=NOH)Me | | | |

$R^3$ is Me, $R^4$ is Me, X is CH, $R^5$ is Cl, $R^9$ is $CF_3$ and $R^8$ is selected from

| | | | |
|---|---|---|---|
| $B(OH)_2$ | O-2-Pyrimidinyl | S-2-Pyrimidinyl | $OSO_2Me$ |
| SH | O-4-Pyrimidinyl | S-4-Pyrimidinyl | $OSO_2CF_3$ |

TABLE 2-continued

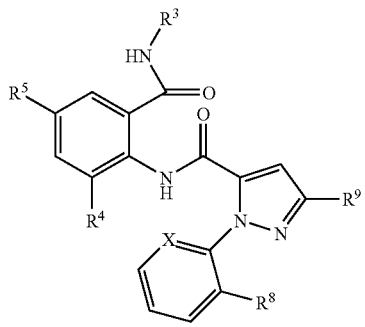

| | | | |
|---|---|---|---|
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$CH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$CH=CH$_2$ |
| MeCONH | CSNH$_2$ | S-2-Oxazolyl | O-Propargyl |
| MeOCONH | CSNHMe | S-6-Cl-3-Pyridazinyl | OCH$_2$C(Cl)=CH$_2$ |
| MeNHCONH | CH$_2$OH | S-2-Pyrazinyl | OCH$_2$CH=C(Cl)$_2$ |
| (EtO)$_2$PO | CH$_2$NHCOMe | SPh | O-c-Pr |
| MeSO$_2$ | CH$_2$NHCO$_2$Me | CH$_2$OMe | O-c-Pentyl |
| MeSO$_2$NH | CH$_2$NHCOCF$_3$ | CH$_2$OEt | OCH$_2$-c-Pr |
| 2-Pyrimidinyl | CH$_2$NHSO$_2$Me | CH$_2$O-i-Pr | OCH$_2$CO$_2$Me |
| 4-Pyrimidinyl | CH$_2$NHSO$_2$NMe$_2$ | CH$_2$NMe$_2$ | OCH$_2$OMe |
| 2-Pyridinyl | CH$_2$CN | CH$_2$SiMe$_3$ | OCH$_2$OCH$_2$CF$_3$ |
| 3-Pyridinyl | CH$_2$OCH$_2$OCH$_3$ | S-(4-ClPh) | OCH$_2$SiMe$_3$ |
| 4-Pyridinyl | CH$_2$OCH$_2$CF$_3$ | SCH$_2$CH=CH$_2$ | OCONHMe |
| 2-Thiazolyl | CH$_2$SMe | S-Propargyl | OCONMe$_2$ |
| 2-Oxazolyl | CH$_2$SCF$_3$ | S-c-Pr | OSO$_2$NMe$_2$ |
| 1-Morpholinyl | CH$_2$SEt | SCH$_2$CN | O-2-Oxazolyl |
| CO$_2$CH$_2$CF$_3$ | O-2-Pyrazinyl | SCONMe$_2$ | O-6-Cl-3-Pyridazinyl |
| COSMe | F$_3$CCONH | PhSO$_2$ | Me$_2$NCONH |
| COCF$_3$ | C(=NOMe)Me | COPh | PhCONH |
| C(=NOH)Me | | | |

R$^3$ is i-Pr, R$^4$ is Me, X is N, R$^5$ is Cl, R$^9$ is Cl and R$^8$ is selected from

| | | | |
|---|---|---|---|
| B(OH)$_2$ | O-2-Pyrimidinyl | S-2-Pyrimidinyl | OSO$_2$Me |
| SH | O-4-Pyrimidinyl | S-4-Pyrimidinyl | OSO$_2$CF$_3$ |
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$CH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$CH=CH$_2$ |
| MeCONH | CSNH$_2$ | S-2-Oxazolyl | O-Propargyl |
| MeOCONH | CSNHMe | S-6-Cl-3-Pyridazinyl | OCH$_2$C(Cl)=CH$_2$ |
| MeNHCONH | CH$_2$OH | S-2-Pyrazinyl | OCH$_2$CH=C(Cl)$_2$ |
| (EtO)$_2$PO | CH$_2$NHCOMe | SPh | O-c-Pr |
| MeSO$_2$ | CH$_2$NHCO$_2$Me | CH$_2$OMe | O-c-Pentyl |
| MeSO$_2$NH | CH$_2$NHCOCF$_3$ | CH$_2$OEt | OCH$_2$-c-Pr |
| 2-Pyrimidinyl | CH$_2$NHSO$_2$Me | CH$_2$O-i-Pr | OCH$_2$CO$_2$Me |
| 4-Pyrimidinyl | CH$_2$NHSO$_2$NMe$_2$ | CH$_2$NMe$_2$ | OCH$_2$OMe |
| 2-Pyridinyl | CH$_2$CN | CH$_2$SiMe$_3$ | OCH$_2$OCH$_2$CF$_3$ |
| 3-Pyridinyl | CH$_2$OCH$_2$OCH$_3$ | S-(4-ClPh) | OCH$_2$SiMe$_3$ |
| 4-Pyridinyl | CH$_2$OCH$_2$CF$_3$ | SCH$_2$CH=CH$_2$ | OCONHMe |
| 2-Thiazolyl | CH$_2$SMe | S-Propargyl | OCONMe$_2$ |
| 2-Oxazolyl | CH$_2$SCF$_3$ | S-c-Pr | OSO$_2$NMe$_2$ |
| 1-Morpholinyl | CH$_2$SEt | SCH$_2$CN | O-2-Oxazolyl |
| CO$_2$CH$_2$CF$_3$ | O-2-Pyrazinyl | SCONMe$_2$ | O-6-Cl-3-Pyridazinyl |
| COSMe | F$_3$CCONH | PhSO$_2$ | Me$_2$NCONH |
| COCF$_3$ | C(=NOMe)Me | COPh | PhCONH |
| C(=NOH)Me | | | |

R$^3$ is Me, R$^4$ is Me, X is N, R$^5$ is Cl, R$^9$ is Cl and R$^8$ is selected from

| | | | |
|---|---|---|---|
| B(OH)$_2$ | O-2-Pyrimidinyl | S-2-Pyrimidinyl | OSO$_2$Me |
| SH | O-4-Pyrimidinyl | S-4-Pyrimidinyl | OSO$_2$CF$_3$ |
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$CH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$CH=CH$_2$ |
| MeCONH | CSNH$_2$ | S-2-Oxazolyl | O-Propargyl |
| MeOCONH | CSNHMe | S-6-Cl-3-Pyridazinyl | OCH$_2$C(Cl)=CH$_2$ |
| MeNHCONH | CH$_2$OH | S-2-Pyrazinyl | OCH$_2$CH=C(Cl)$_2$ |
| (EtO)$_2$PO | CH$_2$NHCOMe | SPh | O-c-Pr |
| MeSO$_2$ | CH$_2$NHCO$_2$Me | CH$_2$OMe | O-c-Pentyl |
| MeSO$_2$NH | CH$_2$NHCOCF$_3$ | CH$_2$OEt | OCH$_2$-c-Pr |

TABLE 2-continued

[Structure: benzamide with R3-NH-C(=O) group, R4 and R5 substituents on benzene ring, connected via NH-C(=O) to a pyrazole bearing R9, with N-substituted phenyl group (X, R8)]

| | | | |
|---|---|---|---|
| 2-Pyrimidinyl | CH$_2$NHSO$_2$Me | CH$_2$O-i-Pr | OCH$_2$CO$_2$Me |
| 4-Pyrimidinyl | CH$_2$NHSO$_2$NMe$_2$ | CH$_2$NMe$_2$ | OCH$_2$OMe |
| 2-Pyridinyl | CH$_2$CN | CH$_2$SiMe$_3$ | OCH$_2$OCH$_2$CF$_3$ |
| 3-Pyridinyl | CH$_2$OCH$_2$OCH$_3$ | S-(4-ClPh) | OCH$_2$SiMe$_3$ |
| 4-Pyridinyl | CH$_2$OCH$_2$CF$_3$ | SCH$_2$CH=CH$_2$ | OCONHMe |
| 2-Thiazolyl | CH$_2$SMe | S-Propargyl | OCONMe$_2$ |
| 2-Oxazolyl | CH$_2$SCF$_3$ | S-c-Pr | OSO$_2$NMe$_2$ |
| 1-Morpholinyl | CH$_2$SEt | SCH$_2$CN | O-2-Oxazolyl |
| CO$_2$CH$_2$CF$_3$ | O-2-Pyrazinyl | SCONMe$_2$ | O-6-Cl-3-Pyridazinyl |
| COSMe | F$_3$CCONH | PhSO$_2$ | Me$_2$NCONH |
| COCF$_3$ | C(=NOMe)Me | COPh | PhCONH |
| C(=NOH)Me | | | |

R$^3$ is Me, R$^4$ is Cl, X is N, R$^5$ is Cl, R$^9$ is Cl and R$^8$ is selected from

| | | | |
|---|---|---|---|
| B(OH)$_2$ | O-2-Pyrimidinyl | S-2-Pyrimidinyl | OSO$_2$Me |
| SH | O-4-Pyrimidinyl | S-4-Pyrimidinyl | OSO$_2$CF$_3$ |
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$CH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$CH=CH$_2$ |
| MeCONH | CSNH$_2$ | S-2-Oxazolyl | O-Propargyl |
| MeOCONH | CSNHMe | S-6-Cl-3-Pyridazinyl | OCH$_2$C(Cl)=CH$_2$ |
| MeNHCONH | CH$_2$OH | S-2-Pyrazinyl | OCH$_2$CH=C(Cl)$_2$ |
| (EtO)$_2$PO | CH$_2$NHCOMe | SPh | O-c-Pr |
| MeSO$_2$ | CH$_2$NHCO$_2$Me | CH$_2$OMe | O-c-Pentyl |
| MeSO$_2$NH | CH$_2$NHCOCF$_3$ | CH$_2$OEt | OCH$_2$-c-Pr |
| 2-Pyrimidinyl | CH$_2$NHSO$_2$Me | CH$_2$O-i-Pr | OCH$_2$CO$_2$Me |
| 4-Pyrimidinyl | CH$_2$NHSO$_2$NMe$_2$ | CH$_2$NMe$_2$ | OCH$_2$OMe |
| 2-Pyridinyl | CH$_2$CN | CH$_2$SiMe$_3$ | OCH$_2$OCH$_2$CF$_3$ |
| 3-Pyridinyl | CH$_2$OCH$_2$OCH$_3$ | S-(4-ClPh) | OCH$_2$SiMe$_3$ |
| 4-Pyridinyl | CH$_2$OCH$_2$CF$_3$ | SCH$_2$CH=CH$_2$ | OCONHMe |
| 2-Thiazolyl | CH$_2$SMe | S-Propargyl | OCONMe$_2$ |
| 2-Oxazolyl | CH$_2$SCF$_3$ | S-c-Pr | OSO$_2$NMe$_2$ |
| 1-Morpholinyl | CH$_2$SEt | SCH$_2$CN | O-2-Oxazolyl |
| CO$_2$CH$_2$CF$_3$ | O-2-Pyrazinyl | SCONMe$_2$ | O-6-Cl-3-Pyridazinyl |
| COSMe | F$_3$CCONH | PhSO$_2$ | Me$_2$NCONH |
| COCF$_3$ | C(=NOMe)Me | COPh | PhCONH |
| C(=NOH)Me | | | |

R$^3$ is i-Pr, R$^4$ is Me, X is N, R$^5$ is Cl, R$^9$ is Br and R$^8$ is selected from

| | | | |
|---|---|---|---|
| B(OH)$_2$ | O-2-Pyrimidinyl | S-2-Pyrimidinyl | OSO$_2$Me |
| SH | O-4-Pyrimidinyl | S-4-Pyrimidinyl | OSO$_2$CF$_3$ |
| SCN | O-2-Pyridinyl | S-2-Pyridinyl | OCH$_2$CN |
| OSiMe$_3$ | O-(5-Cl-2-Pyridinyl) | S-(5-Cl-2-Pyridinyl) | OCH$_2$CH$_2$CN |
| SSMe | O-4-Pyridinyl | S-4-Pyridinyl | OCH(Me)CN |
| SF$_5$ | O-2-Thiazolyl | S-2-Thiazolyl | OCH$_2$CH=CH$_2$ |
| MeCONH | CSNH$_2$ | S-2-Oxazolyl | O-Propargyl |
| MeOCONH | CSNHMe | S-6-Cl-3-Pyridazinyl | OCH$_2$C(Cl)=CH$_2$ |
| MeNHCONH | CH$_2$OH | S-2-Pyrazinyl | OCH$_2$CH=C(Cl)$_2$ |
| (EtO)$_2$PO | CH$_2$NHCOMe | SPh | O-c-Pr |
| MeSO$_2$ | CH$_2$NHCO$_2$Me | CH$_2$OMe | O-c-Pentyl |
| MeSO$_2$NH | CH$_2$NHCOCF$_3$ | CH$_2$OEt | OCH$_2$-c-Pr |
| 2-Pyrimidinyl | CH$_2$NHSO$_2$Me | CH$_2$O-i-Pr | OCH$_2$CO$_2$Me |
| 4-Pyrimidinyl | CH$_2$NHSO$_2$NMe$_2$ | CH$_2$NMe$_2$ | OCH$_2$OMe |
| 2-Pyridinyl | CH$_2$CN | CH$_2$SiMe$_3$ | OCH$_2$OCH$_2$CF$_3$ |
| 3-Pyridinyl | CH$_2$OCH$_2$OCH$_3$ | S-(4-ClPh) | OCH$_2$SiMe$_3$ |
| 4-Pyridinyl | CH$_2$OCH$_2$CF$_3$ | SCH$_2$CH=CH$_2$ | OCONHMe |
| 2-Thiazolyl | CH$_2$SMe | S-Propargyl | OCONMe$_2$ |
| 2-Oxazolyl | CH$_2$SCF$_3$ | S-c-Pr | OSO$_2$NMe$_2$ |
| 1-Morpholinyl | CH$_2$SEt | SCH$_2$CN | O-2-Oxazolyl |
| CO$_2$CH$_2$CF$_3$ | O-2-Pyrazinyl | SCONMe$_2$ | O-6-Cl-3-Pyridazinyl |

TABLE 2-continued

[Structure: benzamide with R5, R4 substituents and pyrazole-carboxamide with R8, R9, X substituents]

| | | | |
|---|---|---|---|
| COSMe | F₃CCONH | PhSO₂ | Me₂NCONH |
| COCF₃ | C(=NOMe)Me | COPh | PhCONH |
| C(=NOH)Me | | | |

R³ is Me, R⁴ is Me, X is N, R⁵ is Cl, R⁹ is Br and R⁸ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCONH | CSNH₂ | S-2-Oxazolyl | O-Propargyl |
| MeOCONH | CSNHMe | S-6-Cl-3-Pyridazinyl) | OCH₂C(Cl)=CH₂ |
| MeNHCONH | CH₂OH | S-2-Pyrazinyl | OCH₂CH=C(Cl)₂ |
| (EtO)₂PO | CH₂NHCOMe | SPh | O-c-Pr |
| MeSO₂ | CH₂NHCO₂Me | CH₂OMe | O-c-Pentyl |
| MeSO₂NH | CH₂NHCOCF₃ | CH₂OEt | OCH₂-c-Pr |
| 2-Pyrimidinyl | CH₂NHSO₂Me | CH₂O-i-Pr | OCH₂CO₂Me |
| 4-Pyrimidinyl | CH₂NHSO₂NMe₂ | CH₂NMe₂ | OCH₂OMe |
| 2-Pyridinyl | CH₂CN | CH₂SiMe₃ | OCH₂OCH₂CF₃ |
| 3-Pyridinyl | CH₂OCH₂OCH₃ | S-(4-ClPh) | OCH₂SiMe₃ |
| 4-Pyridinyl | CH₂OCH₂CF₃ | SCH₂CH=CH₂ | OCONHMe |
| 2-Thiazolyl | CH₂SMe | S-Propargyl | OCONMe₂ |
| 2-Oxazolyl | CH₂SCF₃ | S-c-Pr | OSO₂NMe₂ |
| 1-Morpholinyl | CH₂SEt | SCH₂CN | O-2-Oxazolyl |
| CO₂CH₂CF₃ | O-2-Pyrazinyl | SCONMe₂ | O-6-Cl-3-Pyridazinyl |
| COSMe | F₃CCONH | PhSO₂ | Me₂NCONH |
| COCF₃ | C(=NOMe)Me | COPh | PhCONH |
| C(=NOH)Me | | | |

R³ is Me, R⁴ is Cl, X is N, R⁵ is Cl, R⁹ is Br and R⁸ is selected from

| | | | |
|---|---|---|---|
| B(OH)₂ | O-2-Pyrimidinyl | S-2-Pyrimidinyl | OSO₂Me |
| SH | O-4-Pyrimidinyl | S-4-Pyrimidinyl | OSO₂CF₃ |
| SCN | O-2-Pyridinyl | S-2-Pyridinyl | OCH₂CN |
| OSiMe₃ | O-(5-Cl-2-Pyridinyl) | S-(5-Cl-2-Pyridinyl) | OCH₂CH₂CN |
| SSMe | O-4-Pyridinyl | S-4-Pyridinyl | OCH(Me)CN |
| SF₅ | O-2-Thiazolyl | S-2-Thiazolyl | OCH₂CH=CH₂ |
| MeCONH | CSNH₂ | S-2-Oxazolyl | O-Propargyl |
| MeOCONH | CSNHMe | S-6-Cl-3-Pyridazinyl) | OCH₂C(Cl)=CH₂ |
| MeNHCONH | CH₂OH | S-2-Pyrazinyl | OCH₂CH=C(Cl)₂ |
| (EtO)₂PO | CH₂NHCOMe | SPh | O-c-Pr |
| MeSO₂ | CH₂NHCO₂Me | CH₂OMe | O-c-Pentyl |
| MeSO₂NH | CH₂NHCOCF₃ | CH₂OEt | OCH₂-c-Pr |
| 2-Pyrimidinyl | CH₂NHSO₂Me | CH₂O-i-Pr | OCH₂CO₂Me |
| 4-Pyrimidinyl | CH₂NHSO₂NMe₂ | CH₂NMe₂ | OCH₂OMe |
| 2-Pyridinyl | CH₂CN | CH₂SiMe₃ | OCH₂OCH₂CF₃ |
| 3-Pyridinyl | CH₂OCH₂OCH₃ | S-(4-ClPh) | OCH₂SiMe₃ |
| 4-Pyridinyl | CH₂OCH₂CF₃ | SCH₂CH=CH₂ | OCONHMe |
| 2-Thiazolyl | CH₂SMe | S-Propargyl | OCONMe₂ |
| 2-Oxazolyl | CH₂SCF₃ | S-c-Pr | OSO₂NMe₂ |
| 1-Morpholinyl | CH₂SEt | SCH₂CN | O-2-Oxazolyl |
| CO₂CH₂CF₃ | O-2-Pyrazinyl | SCONMe₂ | O-6-Cl-3-Pyridazinyl |
| COSMe | F₃CCONH | PhSO₂ | Me₂NCONH |
| COCF₃ | C(=NOMe)Me | COPh | PhCONH |
| C(=NOH)Me | | | |

TABLE 3

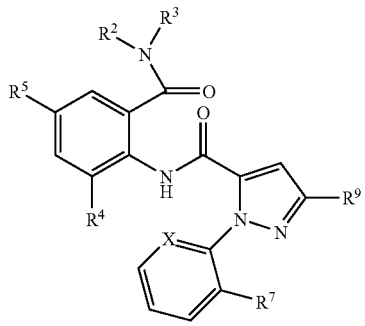

R² is i-Pr, R⁴ is Me, X is N, R⁷ is Cl, R⁹ is CF₃, R⁵ is Cl and R³ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NHt2 | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R² is Me, R⁴ is Me, X is N, R⁷ is Cl, R⁹ is CF₃, R⁵ is Cl and R³ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNHEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R² is i-Pr, R⁴ is Me, X is N, R⁷ is Cl, R⁹ is Cl, R⁵ is Cl and R³ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R² is Me, R⁴ is Me, X is N, R⁷ is Cl, R⁹ is Cl, R⁵ is Cl and R³ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R² is i-Pr, R⁴ is Me, X is N, R⁷ is Cl, R⁹ is Cl, R⁵ is Cl and R³ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R⁷ is Me, R⁴ is Me, X is N, R⁷ is Cl, R⁹ is Br, R⁵ is Cl and R³ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |

TABLE 3-continued

| | | | | |
|---|---|---|---|---|
| S-t-Bu | SNMe(Et) | CH$_2$OCONHMe | CH$_2$NHCO$_2$Me | SN(Me)CO$_2$-n-Hexyl |
| SPh | SNEt$_2$ | SCOMe | CH$_2$NHCO$_2$Et | SN(Me)CO$_2$-i-Pr |
| S(O)Me | S(O)NMe$_2$ | SCO$_2$Me | SN(Et)CO$_2$Et | CH$_2$N(Me)CO$_2$Et |
| S(O)Ph | S-4-morpholinyl | SCONHMe | SN(Me)COMe | SN(Me)SO$_2$NHMe |

TABLE 4

R$^3$ is i-Pr, R$^4$ is Me, X is N, R$^7$ is Cl, R$^9$ is CF$_3$, R$^5$ is Cl and R$^1$ is selected from

| | | | | |
|---|---|---|---|---|
| SCF$_3$ | S-n-Hexyl | CH$_2$OCONHEt | CH$_2$NMe$_2$ | SN(Me)CO$_2$Me |
| SCCl$_3$ | S-(4-Cl-Ph) | CH$_2$OCONMe$_2$ | CH$_2$NEt$_2$ | SN(Et)CO$_2$Me |
| SMe | S-(3-Cl-Ph) | CH$_2$OCOMe | CH$_2$NMe(Et) | SN-(i-Pr)-CO$_2$Me |
| SEt | S-(2-Cl-Ph) | CH$_2$OCO-t-Bu | CH$_2$NHCOMe | SN(Me)CO$_2$Et |
| S-i-Pr | SNMe$_2$ | CH$_2$OCO$_2$Et | CH$_2$NHCOEt | SN(Me)CO$_2$-n-Pr |
| S-t-Bu | SNMe(Et) | CH$_2$OCONHMe | CH$_2$NHCO$_2$Me | SN(Me)CO$_2$-n-Hexyl |
| SPh | SNEt$_2$ | SCOMe | CH$_2$NHCO$_2$Et | SN(Me)CO$_2$-i-Pr |
| S(O)Me | S(O)NMe$_2$ | SCO$_2$Me | SN(Et)CO$_2$Et | CH$_2$N(Me)CO$_2$Et |
| S(O)Ph | S-4-morpholinyl | SCONHMe | SN(Me)COMe | SN(Me)SO$_2$NHMe |

R$^3$ is Me, R$^4$ is Me, X is N, R$^7$ is Cl, R$^9$ is CF$_3$, R$^5$ is Cl and R$^1$ is selected from

| | | | | |
|---|---|---|---|---|
| SCF$_3$ | S-n-Hexyl | CH$_2$OCONHEt | CH$_2$NMe$_2$ | SN(Me)CO$_2$Me |
| SCCl$_3$ | S-(4-Cl-Ph) | CH$_2$OCONMe$_2$ | CH$_2$NEt$_2$ | SN(Et)CO$_2$Me |
| SMe | S-(3-Cl-Ph) | CH$_2$OCOMe | CH$_2$NMe(Et) | SN-(i-Pr)-CO$_2$Me |
| SEt | S-(2-Cl-Ph) | CH$_2$OCO-t-Bu | CH$_2$NHCOMe | SN(Me)CO$_2$Et |
| S-i-Pr | SNMe$_2$ | CH$_2$OCO$_2$Et | CH$_2$NHCOEt | SN(Me)CO$_2$-n-Pr |
| S-t-Bu | SNMe(Et) | CH$_2$OCONHMe | CH$_2$NHCO$_2$Me | SN(Me)CO$_2$-n-Hexyl |
| SPh | SNEt$_2$ | SCOMe | CH$_2$NHCO$_2$Et | SN(Me)CO$_2$-i-Pr |
| S(O)Me | S(O)NMe$_2$ | SCO$_2$Me | SN(Et)CO$_2$Et | CH$_2$N(Me)CO$_2$Et |
| S(O)Ph | S-4-morpholinyl | SCONHMe | SN(Me)COMe | SN(Me)SO$_2$NHMe |

R$^3$ is i-Pr, R$^4$ is Me, X is N, R$^7$ is Cl, R$^9$ is Cl, R$^5$ is Cl and R$^1$ is selected from

| | | | | |
|---|---|---|---|---|
| SCF$_3$ | S-n-Hexyl | CH$_2$OCONHEt | CH$_2$NMe$_2$ | SN(Me)CO$_2$Me |
| SCCl$_3$ | S-(4-Cl-Ph) | CH$_2$OCONMe$_2$ | CH$_2$NEt$_2$ | SN(Et)CO$_2$Me |
| SMe | S-(3-Cl-Ph) | CH$_2$OCOMe | CH$_2$NMe(Et) | SN-(i-Pr)-CO$_2$Me |
| SEt | S-(2-Cl-Ph) | CH$_2$OCO-t-Bu | CH$_2$NHCOMe | SN(Me)CO$_2$Et |
| S-i-Pr | SNMe$_2$ | CH$_2$OCO$_2$Et | CH$_2$NHCOEt | SN(Me)CO$_2$-n-Pr |
| S-t-Bu | SNMe(Et) | CH$_2$OCONHMe | CH$_2$NHCO$_2$Me | SN(Me)CO$_2$-n-Hexyl |
| SPh | SNEt$_2$ | SCOMe | CH$_2$NHCO$_2$Et | SN(Me)CO$_2$-i-Pr |
| S(O)Me | S(O)NMe$_2$ | SCO$_2$Me | SN(Et)CO$_2$Et | CH$_2$N(Me)CO$_2$Et |
| S(O)Ph | S-4-morpholinyl | SCONHMe | SN(Me)COMe | SN(Me)SO$_2$NHMe |

R$^3$ is Me, R$^4$ is Me, X is N, R$^7$ is Cl, R$^9$ is Cl, R$^5$ is Cl and R$^1$ is selected from

| | | | | |
|---|---|---|---|---|
| SCF$_3$ | S-n-Hexyl | CH$_2$OCONHEt | CH$_2$NMe$_2$ | SN(Me)CO$_2$Me |
| SCCl$_3$ | S-(4-Cl-Ph) | CH$_2$OCONMe$_2$ | CH$_2$NEt$_2$ | SN(Et)CO$_2$Me |

TABLE 4-continued

[Structure: benzamide with R3, R5, R4, R1 substituents linked to N-pyrazole carboxamide with R9, and X-containing ring with R7]

| | | | | |
|---|---|---|---|---|
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R³ is i-Pr, R⁴ is Me, X is N, R⁷ is Cl, R⁹ is Br, R⁵ is Cl and R¹ is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

R³ is Me, R⁴ is Me, X is N, R⁷ is Cl, R⁹ is Br, R⁵ is Cl and H1 is selected from

| | | | | |
|---|---|---|---|---|
| SCF₃ | S-n-Hexyl | CH₂OCONHEt | CH₂NMe₂ | SN(Me)CO₂Me |
| SCCl₃ | S-(4-Cl-Ph) | CH₂OCONMe₂ | CH₂NEt₂ | SN(Et)CO₂Me |
| SMe | S-(3-Cl-Ph) | CH₂OCOMe | CH₂NMe(Et) | SN-(i-Pr)-CO₂Me |
| SEt | S-(2-Cl-Ph) | CH₂OCO-t-Bu | CH₂NHCOMe | SN(Me)CO₂Et |
| S-i-Pr | SNMe₂ | CH₂OCO₂Et | CH₂NHCOEt | SN(Me)CO₂-n-Pr |
| S-t-Bu | SNMe(Et) | CH₂OCONHMe | CH₂NHCO₂Me | SN(Me)CO₂-n-Hexyl |
| SPh | SNEt₂ | SCOMe | CH₂NHCO₂Et | SN(Me)CO₂-i-Pr |
| S(O)Me | S(O)NMe₂ | SCO₂Me | SN(Et)CO₂Et | CH₂N(Me)CO₂Et |
| S(O)Ph | S-4-morpholinyl | SCONHMe | SN(Me)COMe | SN(Me)SO₂NHMe |

TABLE 5

[Structure: benzamide with R3, R5, R4 substituents linked to NH-pyrazole carboxamide with R9, and X-containing ring with R7]

R⁴ is Me, X is N, R⁵ is Cl, R⁹ is CF₃, R⁷ is Cl, and R³ is selected from

| | | | | |
|---|---|---|---|---|
| CH₂CONH₂ | CH₂CH₂OCO₂Me | CH₂CH₂N(Me)COMe | CH(Me)CH₂OCOMe | |
| CH₂CSNH₂ | C(Me)₂CH₂CONH₂ | CH₂CH₂NHCO₂Me | CH(Me)CH₂OCO₂Me | |
| CH₂CH₂OCOMe | CH₂CH₂NHCO₂Et | CH₂CH₂NHCONHMe | CH(Me)CH₂OCO₂Et | |
| CH₂CH₂NHSO₂Me | CH₂CH₂NHCOMe | CH(Me)CH₂NHCOMe | CH(Me)CH₂CONH₂ | |
| CH₂CH₂CONH₂ | CH₂CH(=NOH) | CH(Me)CH₂N(Me)COMe | CH(Me)CH₂OCONHMe | |
| CH₂CH(=NOH) | CH(Me)C(Me)(=NOMe) | CH(Me)CH₂NHCO₂Me | CH₂CH₂NHSO₂CF₃ | |
| CH₂CH(=NOMe) | CH(Me)C(Me)(=NOEt) | CH(Me)CH₂NHCO₂Et | CH(Me)CH₂OCONMe₂ | |
| CH₂CH(=NOEt) | C(Me)₂CH(=NOH) | CH₂CH₂N(Me)CONHMe | CH(Me)CH₂CONCHMe | |
| CH₂C(Me)(=NOH) | C(Me)₂CH(=NOMe) | CH(Me)CH₂NHPO(OEt)₂ | CH(Me)CH₂NHSO₂Me | |
| CH₂C(Me)(=NOMe) | C(Me)₂CH2(=NOEt) | CH₂CH₂CH(=NO-i-Pr) | CH(Me)C(Me)(=NO-i-Pr) | |

TABLE 5-continued

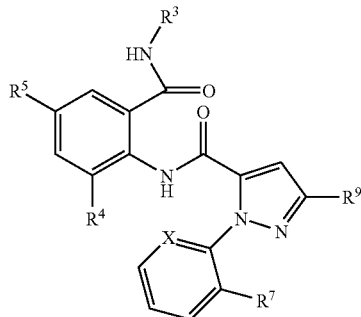

| | | | |
|---|---|---|---|
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

R⁴ is Me, X is N, R⁵ is Cl, R⁹ is Cl, R⁷ is Cl, and R³ is selected from

| | | | |
|---|---|---|---|
| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH(Me)CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NO-i-Pr) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

R⁴ is Me, X is N, R⁵ is Cl, R⁹ is Br, R⁷ is Cl, and R³ is selected from

| | | | |
|---|---|---|---|
| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH(Me)CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NOEt) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

R⁴ is Me, X is CH, R⁵ is Cl, R⁹ is CF₃, R⁷ is Cl, and R³ is selected from

| | | | |
|---|---|---|---|
| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH(Me)CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NOEt) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

TABLE 5-continued

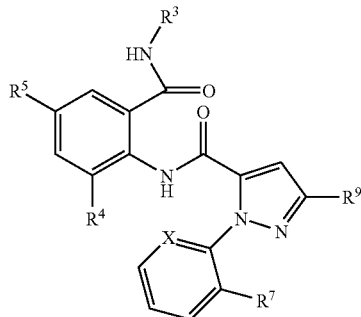

| R⁴ is Me, X is CH, R⁵ is Cl, R⁹ is Cl, R⁷ is Cl, and R³ is selected from |

| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH(Me)CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NOEt) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

| R⁴ is Me, X is CH, R⁵ is Cl, R⁹ is Br, R⁷ is Cl, and R³ is selected from |

| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH₂CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NOEt) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

| R⁴ is Cl, X is N, R⁵ is Cl, R⁹ is CF₃, R⁷ is Cl, and R³ is selected from |

| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH₂CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NOEt) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

| R⁴ is Cl, X is N, R⁵ is Cl, R⁹ is Cl, R⁷ is Cl, and R³ is selected from |

| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |

TABLE 5-continued

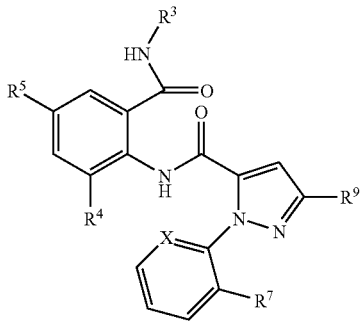

| | | | |
|---|---|---|---|
| CH$_2$CH(=NOMe) | CH(Me)C(Me)(=NOEt) | CH(Me)CH$_2$NHCO$_2$Et | CH(Me)CH$_2$OCONMe$_2$ |
| CH$_2$CH(=NOEt) | C(Me)$_2$CH(=NOH) | CH$_2$CH$_2$N(Me)CONHMe | CH(Me)CH$_2$CONCHMe |
| CH$_2$C(Me)(=NOH) | C(Me)$_2$CH(=NOMe) | CH(Me)CH$_2$NHPO(OEt)$_2$ | CH(Me)CH$_2$NHSO$_2$Me |
| CH$_2$C(Me)(=NOMe) | C(Me)$_2$CH2(=NOEt) | CH$_2$CH$_2$CH(=NO-i-Pr) | CH(Me)C(Me)(=NO-i-Pr) |
| CH$_2$C(Me)(=NOEt) | CH$_2$CH$_2$CH(=NOH) | CH(Me)CH$_2$CH(=NOH) | CH(Me)CH$_2$CH(=NO-i-Pr) |
| CH(Me)CH(=NOH) | CH$_2$CH$_2$CH(=NOMe) | CH(Me)CH$_2$CH(=NOMe) | C(Me)$_2$C(Me)(=NO-i-Pr) |
| CH(Me)CH(=NOMe) | CH$_2$CH$_2$CH(=NOEt) | CH(Me)CH$_2$CH(=NOEt) | C(Me)$_2$CH$_2$CH(=NOH) |
| CH(Me)CH(=NOEt) | CH(Me)CH(=NO-i-Pr) | C(Me)$_2$C(Me)(=NOH) | C(Me)$_2$CH$_2$CH(=NOMe) |
| CH$_2$CH(=NO-i-Pr) | C(Me)$_2$CH(=NO-i-Pr) | C(Me)$_2$C(Me)(=NOMe) | C(Me)$_2$CH$_2$CH(=NOEt) |
| CH$_2$CH$_2$OCO$_2$Et | CH$_2$C(Me)(=NO-i-Pr) | C(Me2)C(Me)(=NOEt) | C(Me)$_2$CH$_2$CH(=NO-i-Pr) |

R$^4$ is Cl, X is N, R$^5$ is Cl, R$^9$ is Br, R$^7$ is Cl, and R$^3$ is selected from

| | | | |
|---|---|---|---|
| CH$_2$CONH$_2$ | CH$_2$CH$_2$OCO$_2$Me | CH$_2$CH$_2$N(Me)COMe | CH(Me)CH$_2$OCOMe |
| CH$_2$CSNH$_2$ | C(Me)$_2$CH$_2$CONH$_2$ | CH$_2$CH$_2$NHCO$_2$Me | CH(Me)CH$_2$OCO$_2$Me |
| CH$_2$CH$_2$OCOMe | CH$_2$CH$_2$NHCO$_2$Et | CH$_2$CH$_2$NHCONHMe | CH(Me)CH$_2$OCO$_2$Et |
| CH$_2$CH$_2$NHSO$_2$Me | CH$_2$CH$_2$NHCOMe | CH(Me)CH$_2$NHCOMe | CH(Me)CH$_2$CONH$_2$ |
| CH$_2$CH$_2$CONH$_2$ | CH(Me)C(Me)(=NOH) | CH(Me)CH$_2$N(Me)COMe | CH(Me)CH$_2$OCONHMe |
| CH$_2$CH(=NOH) | CH(Me)C(Me)(=NOMe) | CH(Me)CH$_2$NHCO$_2$Me | CH$_2$CH$_2$NHSO$_2$CF$_3$ |
| CH$_2$CH(=NOMe) | CH(Me)C(Me)(=NOEt) | CH(Me)CH$_2$NHCO$_2$Et | CH(Me)CH$_2$OCONMe$_2$ |
| CH$_2$CH(=NOEt) | C(Me)$_2$CH(=NOH) | CH$_2$CH$_2$N(Me)CONHMe | CH(Me)CH$_2$CONCHMe |
| CH$_2$C(Me)(=NOH) | C(Me)$_2$CH(=NOMe) | CH(Me)CH$_2$NHPO(OEt)$_2$ | CH(Me)CH$_2$NHSO$_2$Me |
| CH$_2$C(Me)(=NOMe) | C(Me)$_2$CH2(=NOEt) | CH$_2$CH$_2$CH(=NO-i-Pr) | CH(Me)C(Me)(=NO-i-Pr) |
| CH$_2$C(Me)(=NOEt) | CH$_2$CH$_2$CH(=NOH) | CH(Me)CH$_2$CH(=NOH) | CH(Me)CH$_2$CH(=NO-i-Pr) |
| CH(Me)CH(=NOH) | CH$_2$CH$_2$CH(=NOMe) | CH(Me)CH$_2$CH(=NOMe) | C(Me)$_2$C(Me)(=NO-i-Pr) |
| CH(Me)CH(=NOMe) | CH$_2$CH$_2$CH(=NOEt) | CH(Me)CH$_2$CH(=NOEt) | C(Me)$_2$CH$_2$CH(=NOH) |
| CH(Me)CH(=NOEt) | CH(Me)CH(=NO-i-Pr) | C(Me)$_2$C(Me)(=NOH) | C(Me)$_2$CH$_2$CH(=NOMe) |
| CH$_2$CH(=NO-i-Pr) | C(Me)$_2$CH(=NO-i-Pr) | C(Me)$_2$C(Me)(=NOMe) | C(Me)$_2$CH$_2$CH(=NOEt) |
| CH$_2$CH$_2$OCO$_2$Et | CH$_2$C(Me)(=NO-i-Pr) | C(Me2)C(Me)(=NOEt) | C(Me)$_2$CH$_2$CH(=NO-i-Pr) |

R$^4$ is Cl, X is CH2 R$^5$ is Cl, P2 is CF$_3$, R$^7$ is Cl, and R$^3$ is selected from

| | | | |
|---|---|---|---|
| CH$_2$CONH$_2$ | CH$_2$CH$_2$OCO$_2$Me | CH$_2$CH$_2$N(Me)COMe | CH(Me)CH$_2$OCOMe |
| CH$_2$CSNH$_2$ | C(Me)$_2$CH$_2$CONH$_2$ | CH$_2$CH$_2$NHCO$_2$Me | CH(Me)CH$_2$OCO$_2$Me |
| CH$_2$CH$_2$OCOMe | CH$_2$CH$_2$NHCO$_2$Et | CH$_2$CH$_2$NHCONHMe | CH(Me)CH$_2$OCO$_2$Et |
| CH$_2$CH$_2$NHSO$_2$Me | CH$_2$CH$_2$NHCOMe | CH(Me)CH$_2$NHCOMe | CH(Me)CH$_2$CONH$_2$ |
| CH$_2$CH$_2$CONH$_2$ | CH(Me)C(Me)(=NOH) | CH(Me)CH$_2$N(Me)COMe | CH(Me)CH$_2$OCONHMe |
| CH$_2$CH(=NOH) | CH(Me)C(Me)(=NOMe) | CH(Me)CH$_2$NHCO$_2$Me | CH$_2$CH$_2$NHSO$_2$CF$_3$ |
| CH$_2$CH(=NOMe) | CH(Me)C(Me)(=NOEt) | CH(Me)CH$_2$NHCO$_2$Et | CH(Me)CH$_2$OCONMe$_2$ |
| CH$_2$CH(=NOEt) | C(Me)$_2$CH(=NOH) | CH$_2$CH$_2$N(Me)CONHMe | CH(Me)CH$_2$CONCHMe |
| CH$_2$C(Me)(=NOH) | C(Me)$_2$CH(=NOMe) | CH(Me)CH$_2$NHPO(OEt)$_2$ | CH(Me)CH$_2$NHSO$_2$Me |
| CH$_2$C(Me)(=NOMe) | C(Me)$_2$CH2(=NOEt) | CH$_2$CH$_2$CH(=NO-i-Pr) | CH(Me)C(Me)(=NO-i-Pr) |
| CH$_2$C(Me)(=NOEt) | CH$_2$CH$_2$CH(=NOH) | CH(Me)CH$_2$CH(=NOH) | CH(Me)CH$_2$CH(=NO-i-Pr) |
| CH(Me)CH(=NOH) | CH$_2$CH$_2$CH(=NOMe) | CH(Me)CH$_2$CH(=NOMe) | C(Me)$_2$C(Me)(=NO-i-Pr) |
| CH(Me)CH(=NOMe) | CH$_2$CH$_2$CH(=NOEt) | CH(Me)CH$_2$CH(=NOEt) | C(Me)$_2$CH$_2$CH(=NOH) |
| CH(Me)CH(=NOEt) | CH(Me)CH(=NO-i-Pr) | C(Me)$_2$C(Me)(=NOH) | C(Me)$_2$CH$_2$CH(=NOMe) |
| CH$_2$CH(=NO-i-Pr) | C(Me)$_2$CH(=NO-i-Pr) | C(Me)$_2$C(Me)(=NOMe) | C(Me)$_2$CH$_2$CH(=NOEt) |
| CH$_2$CH$_2$OCO$_2$Et | CH$_2$C(Me)(=NO-i-Pr) | C(Me2)C(Me)(=NOEt) | C(Me)$_2$CH$_2$CH(=NO-i-Pr) |

R$^4$ is Cl, X is CH, R$^5$ is Cl, R$^9$ is Cl, R$^7$ is Cl, and R$^3$ is selected from

| | | | |
|---|---|---|---|
| CH$_2$CONH$_2$ | CH$_2$CH$_2$OCO$_2$Me | CH$_2$CH$_2$N(Me)COMe | CH(Me)CH$_2$OCOMe |
| CH$_2$CSNH$_2$ | C(Me)$_2$CH$_2$CONH$_2$ | CH$_2$CH$_2$NHCO$_2$Me | CH(Me)CH$_2$OCO$_2$Me |
| CH$_2$CH$_2$OCOMe | CH$_2$CH$_2$NHCO$_2$Et | CH$_2$CH$_2$NHCONHMe | CH(Me)CH$_2$OCO$_2$Et |
| CH$_2$CH$_2$NHSO$_2$Me | CH$_2$CH$_2$NHCOMe | CH(Me)CH$_2$NHCOMe | CH(Me)CH$_2$CONH$_2$ |
| CH$_2$CH$_2$CONH$_2$ | CH(Me)C(Me)(=NOH) | CH(Me)CH$_2$N(Me)COMe | CH(Me)CH$_2$OCONHMe |
| CH$_2$CH(=NOH) | CH(Me)C(Me)(=NOMe) | CH(Me)CH$_2$NHCO$_2$Me | CH$_2$CH$_2$NHSO$_2$CF$_3$ |
| CH$_2$CH(=NOMe) | CH(Me)C(Me)(=NOEt) | CH(Me)CH$_2$NHCO$_2$Et | CH(Me)CH$_2$OCONMe$_2$ |
| CH$_2$CH(=NOEt) | C(Me)$_2$CH(=NOH) | CH$_2$CH$_2$N(Me)CONHMe | CH(Me)CH$_2$CONCHMe |
| CH$_2$C(Me)(=NOH) | C(Me)$_2$CH(=NOMe) | CH(Me)CH$_2$NHPO(OEt)$_2$ | CH(Me)CH$_2$NHSO$_2$Me |
| CH$_2$C(Me)(=NOMe) | C(Me)$_2$CH2(=NOEt) | CH$_2$CH$_2$CH(=NO-i-Pr) | CH(Me)C(Me)(=NO-i-Pr) |
| CH$_2$C(Me)(=NOEt) | CH$_2$CH$_2$CH(=NOH) | CH(Me)CH$_2$CH(=NOH) | CH(Me)CH$_2$CH(=NO-i-Pr) |
| CH(Me)CH(=NOH) | CH$_2$CH$_2$CH(=NOMe) | CH(Me)CH$_2$CH(=NOMe) | C(Me)$_2$C(Me)(=NO-i-Pr) |
| CH(Me)CH(=NOMe) | CH$_2$CH$_2$CH(=NOEt) | CH(Me)CH$_2$CH(=NOEt) | C(Me)$_2$CH$_2$CH(=NOH) |
| CH(Me)CH(=NOEt) | CH(Me)CH(=NO-i-Pr) | C(Me)$_2$C(Me)(=NOH) | C(Me)$_2$CH$_2$CH(=NOMe) |

TABLE 5-continued

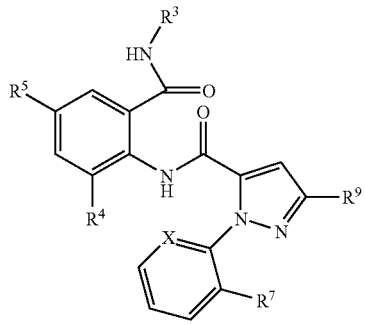

| | | | |
|---|---|---|---|
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

R⁴ is Cl, X is CH, R⁵ is Cl, R⁹ is Br, R⁷ is Cl, and R³ is selected from

| | | | |
|---|---|---|---|
| CH₂CONH₂ | CH₂CH₂OCO₂Me | CH₂CH₂N(Me)COMe | CH(Me)CH₂OCOMe |
| CH₂CSNH₂ | C(Me)₂CH₂CONH₂ | CH₂CH₂NHCO₂Me | CH(Me)CH₂OCO₂Me |
| CH₂CH₂OCOMe | CH₂CH₂NHCO₂Et | CH₂CH₂NHCONHMe | CH(Me)CH₂OCO₂Et |
| CH₂CH₂NHSO₂Me | CH₂CH₂NHCOMe | CH(Me)CH₂NHCOMe | CH(Me)CH₂CONH₂ |
| CH₂CH₂CONH₂ | CH(Me)C(Me)(=NOH) | CH(Me)CH₂N(Me)COMe | CH(Me)CH₂OCONHMe |
| CH₂CH(=NOH) | CH(Me)C(Me)(=NOMe) | CH(Me)CH₂NHCO₂Me | CH₂CH₂NHSO₂CF₃ |
| CH₂CH(=NOMe) | CH(Me)C(Me)(=NOEt) | CH(Me)CH₂NHCO₂Et | CH(Me)CH₂OCONMe₂ |
| CH₂CH(=NOEt) | C(Me)₂CH(=NOH) | CH₂CH₂N(Me)CONHMe | CH(Me)CH₂CONCHMe |
| CH₂C(Me)(=NOH) | C(Me)₂CH(=NOMe) | CH(Me)CH₂NHPO(OEt)₂ | CH(Me)CH₂NHSO₂Me |
| CH₂C(Me)(=NOMe) | C(Me)₂CH2(=NOEt) | CH₂CH₂CH(=NO-i-Pr) | CH(Me)C(Me)(=NO-i-Pr) |
| CH₂C(Me)(=NOEt) | CH₂CH₂CH(=NOH) | CH(Me)CH₂CH(=NOH) | CH(Me)CH₂CH(=NO-i-Pr) |
| CH(Me)CH(=NOH) | CH₂CH₂CH(=NOMe) | CH(Me)CH₂CH(=NOMe) | C(Me)₂C(Me)(=NO-i-Pr) |
| CH(Me)CH(=NOMe) | CH₂CH₂CH(=NOEt) | CH(Me)CH₂CH(=NOEt) | C(Me)₂CH₂CH(=NOH) |
| CH(Me)CH(=NOEt) | CH(Me)CH(=NO-i-Pr) | C(Me)₂C(Me)(=NOH) | C(Me)₂CH₂CH(=NOMe) |
| CH₂CH(=NO-i-Pr) | C(Me)₂CH(=NO-i-Pr) | C(Me)₂C(Me)(=NOMe) | C(Me)₂CH₂CH(=NOEt) |
| CH₂CH₂OCO₂Et | CH₂C(Me)(=NO-i-Pr) | C(Me2)C(Me)(=NOEt) | C(Me)₂CH₂CH(=NO-i-Pr) |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, fi, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 14; Klingman, *Weed Control as a Science*, John Wiley and Sons, Inc., New York, 1961, pp 81-96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

| Wettable Powder | |
|---|---|
| Compound 4 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
|---|---|
| Compound 19 | 10.0% |
| attapulgite granules (low volatile matter, 0.71/0.30 mm; U.S.S. No. 25-50 sieves) | 90.0%. |

EXAMPLE C

| Extruded Pellet | |
|---|---|
| Compound 56 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

| Emulsifiable Concentrate | |
|---|---|
| Compound 19 | 20.0% |
| blend of oil soluble sulfonates and polyoxyethylene ethers | 10.0% |
| isophorone | 70.0%. |

EXAMPLE E

| Granule | |
|---|---|
| Compound 56 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops, of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g. migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepismia saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis*

Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoima lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphosmethyl, bifenthrin, binfenazate, buprofezin, carbofuran, chlorfenapyr, chlorfluazuron, chlorpyrifos, chlorpyrifos-methyl chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, flufenerim, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl, clothiazoben/benclothiaz and fenamiphos; bactericides such as streptomycin; acaricides such as amidoflumet, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as *Bacillus thuringiensis* toxin). The effect of exogenously applied invertebrate pest control compounds of this invention may be synergistic with the expressed toxin proteins.

A general reference for these agricultural protectants is *The Pesticide Manual*, 12th Edition, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

Of note are compositions of this invention that comprise, in addition to the Formula I component (and any surfactant and/or diluent) at least one additional compound or agent for controlling an invertebrate pest. In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound or agent is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A through D for compound descriptions. The following abbreviations are used in the Index Tables that follow: Me means methyl, Et means ethyl, i-Pr means isopropyl, c-Pr means cyclopropyl, t-Bu means tertary butyl and Ph means phenyl. The abbreviation "Ex." stands for "Example" and is followed by a number indicating in which example the compound is prepared. The abbreviation "dec." stands for "decomposed."

Index Table A

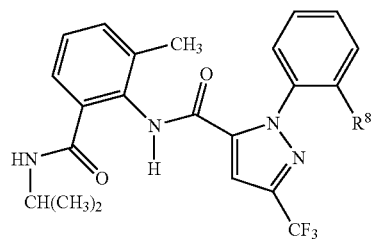

| Compound | $R^8$ | Physical Properties* |
|---|---|---|
| 2 | $CH_2NH_2$ | * |
| 3 | $CH_2NHCOCF_3$ | * |
| 4 (Ex.1) | $CH_2OH$ | * |

*See NMR data in Index Table C

Index Table B

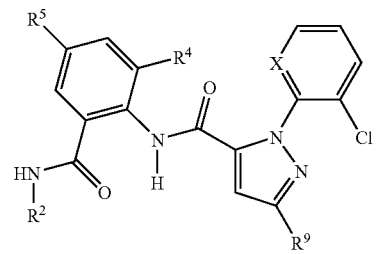

| Compound | $R^2$ | $R^4$ | $R^5$ | X | $R^9$ | m.p. ° C. |
|---|---|---|---|---|---|---|
| 5 | i-Pr | Me | NHCONHEt | N | $CF_3$ | 231-233 |
| 6 | i-Pr | Me | $NHCOCH_3$ | N | $CF_3$ | 232-234 |
| 7 | i-Pr | Me | $NHCOCF_3$ | N | $CF_3$ | 156 |
| 8 | i-Pr | Me | NHCOO-t-Bu | N | $CF_3$ | 225 |
| 9 | i-Pr | Me | NHCONH-i-Pr | N | $CF_3$ | 247(dec.) |
| 10 (Ex. 5) | i-Pr | Me | NHCOPh | N | $CF_3$ | * |
| 11 | i-Pr | Me | NHCONHPh | N | $CF_3$ | * |
| 12 (Ex. 2) | i-Pr | Me | $CO_2Me$ | N | $CF_3$ | 204-206 |
| 13 | i-Pr | Me | $CH_2OH$ | N | $CF_3$ | 199-201 |
| 14 | i-Pr | Me | CONHMe | N | $CF_3$ | 168-170 |
| 15 | Me | Me | $CO_2Me$ | N | $CF_3$ | 156-158 |
| 16 | i-Pr | Me | $CO_2H$ | N | $CF_3$ | 198-200 |
| 17 | i-Pr | Me | CONH-c-Pr | N | $CF_3$ | 194-196 |

-continued

Index Table B

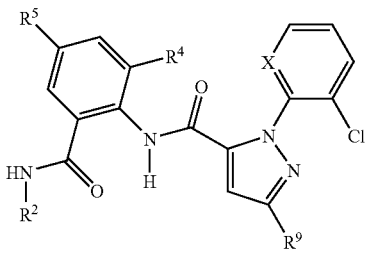

| Compound | R² | R⁴ | R⁵ | X | R⁹ | m.p. ° C. |
|---|---|---|---|---|---|---|
| 18 | i-Pr | Me | CO₂Et | N | CF₃ | 197-199 |
| 19 (Ex. 3) | i-Pr | Me | COMe | N | CF₃ | 135-137 |
| 20 | i-Pr | Me | CO₂Me | N | Br | 182-184 |
| 21 | i-Pr | Me | CONH-i-Pr | N | CF₃ | 152-154 |
| 22 | i-Pr | Me | C(=NOH)Me | N | CF₃ | 152-153 |
| 23 | i-Pr | Me | C(=NOMe)Me | N | CF₃ | 208-210 |
| 24 (Ex. 4) | i-Pr | Me | NH₂ | N | CF₃ | * |
| 25 | i-Pr | Me | NH₂ | CH | CF₃ | * |
| 26 | i-Pr | Me | NHCONMe₂ | CH | CF₃ | * |
| 27 | i-Pr | Me | NHCONH₂ | CH | CF₃ | * |
| 28 | i-Pr | Cl | NH₂ | N | CF₃ | * |
| 29 | Me | Me | NH₂ | N | CF₃ | * |
| 30 | t-Bu | Me | NH₂ | N | CF₃ | * |
| 31 | i-Pr | Me | NHCO(CH₂)₂CO₂H | N | CF₃ | 164-165 |
| 32 | i-Pr | Me | NHCO(CH₂)₃CO₂H | N | CF₃ | 202-204 |
| 33 | i-Pr | Me | NHCO[3-(CO₂H)-2-pyridinyl] | N | CF₃ | * |

*See NMR data in Index Table D

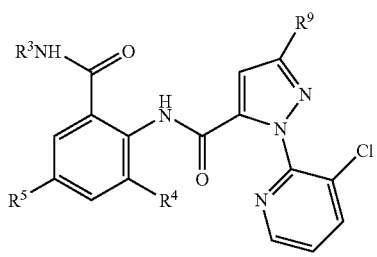

Index Table C

| Compound | R³ | R⁴ | R⁵ | R⁹ | Phys |
|---|---|---|---|---|---|
| 34 | CH₂CONH₂ | Me | H | CF₃ | 185-190 |
| 35 | CH(Me)CONH₂ | Me | H | CF₃ | 153-154 |
| 36 | CH(Me)CONMe₂ | Cl | Cl | Cl | 115-117 |
| 37 | CH(Me)CONMe₂ | Cl | Cl | Br | 122-124 |
| 38 | CH(Me)CONMe₂ | Cl | Cl | CF₃ | 124-126 |
| 39 | CH(Me)CONMe₂ | Me | Cl | Cl | 125-130 |
| 40 | CH(Me)CONMe₂ | Me | Cl | CF₃ | 125-126 |
| 41 | CH(Me)CONEt₂ | Cl | Cl | Cl | 125-127 |
| 42 | CH(Me)CONEt₂ | Cl | Cl | Br | 120-122 |
| 43 | CH(Me)CONEt₂ | Cl | Cl | CF₃ | 119-120 |
| 44 | CH(Me)CONEt₂ | Me | Cl | Cl | 128-129 |
| 45 | CH(Me)CONEt₂ | Me | Cl | Br | 115-116 |
| 46 | CH(Me)CONEt₂ | Me | Cl | CF₃ | 128-129 |
| 47 | CH(Me)CONH₂ | Br | Br | Br | 250 |
| 48 | CH(Me)CONH₂ | Cl | F | Br | 243-244 |
| 49 | CH(Me)CONMe₂ | Me | Cl | Br | 133-134 |
| 50 | CH(=NOMe) | Cl | Cl | Cl | 165-166 |
| 51 | CH(=NOMe) | Cl | Cl | Br | 148-149 |
| 52 | CH(=NOMe) | Cl | Cl | CF₃ | 157-158 |
| 53 | CH(=NOMe) | Me | Cl | Cl | 157-158 |
| 54 | CH(=NOMe) | Me | Cl | Br | 134-136 |
| 55 | CH(=NOMe) | Me | Cl | CF₃ | 159-160 |
| 56 | CH(=NOMe) | Me | Cl | Cl | 196-197 |

-continued

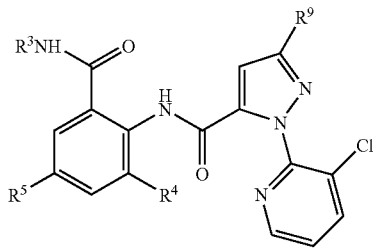

| | | | | | |
|---|---|---|---|---|---|
| 57 | CH(=NOMe) | Cl | Cl | CF$_3$ | 126-127 |
| 58 | CH(=NOMe) | Cl | Cl | Br | 212-213 |
| 59 | CH(Me)CH$_2$OCONHEt | Cl | Cl | Cl | 156-157 |
| 60 | CH(Me)CH$_2$OCONHEt | Cl | Cl | Br | 157-158 |
| 61 | CH(Me)CH$_2$OCONHEt | Cl | Cl | CF$_3$ | 152-153 |
| 62 | CH(Me)CH$_2$OCONHEt | Me | Cl | Cl | 141-142 |
| 63 | CH(Me)CH$_2$OCONHEt | Me | Cl | Br | 158-159 |
| 64 | CH(Me)CH$_2$OCONHEt | Me | Cl | CF$_3$ | |

INDEX TABLE D
$^1$H NMR Data (CDCl$_3$ solution unless indicated otherwise)$^a$ 2 (DMSO-d6): δ 10.45 (s, 1H), 8.35 (bs, 2H), 8.05 (s, 1H), 7.70-7.26 (m, 8H), 3.93 (m, 1H), 3.74 (s, 2H), 2.15 (s, 3H), 1.05 (d, 6H).

3 δ 10.23 (s, 1H), 7.96 )s, 1H), 7.52 (m, 2H), 7.40 (m, 1H), 7.30 (m, 1H), 7.20 (m, 4H), 5.91 (d, 1H), 4.37 (s, 1H), 4.15 (m, 1H), 2.18 (s, 3H), 1.22 (d, 6H).

4 δ 9.81 (s, 1H), 7.65 (m, 1H), 7.51 (m, 1H), 7.38 (m, 1H), 7.20 (m, 5H <5.90 (d, 1H), 4.44 (s, 2H), 4.11 (m, 1H), 3.58 (bs, 1H), 2.15 (s, 3H), 1.22 (d, 6H).

10 (DMSO-d$_6$): δ 10.36 (s, 1H), 10.22 (s, <1H), 8.56 (d, 1H), 8.21 (d, 1H), 7.98-7-92 (m, 3H), 7.82 (distorted s, 1H), 7.78 (s, 1H), 7.70-7.50 (m, 5H), 3.93 (septet. 1H), 2.18 (s, 1H), 1.03 (d, 6H).

11 (DMSO-d$_6$): δ 8.81 (s, 1H), 8.64 (s, 2H), 8.52 (d, 1H), 8.20 (d, 1H), 7.91 (d, 1H), 7 77 (s, 1H), 7.63 (dd, 1H), 7.43 (d, >2H), 7.31 (m, 1H), 7.27 (t, >2H), 6.97 (t, >1H), 3.93 (m, 1H), 2.12 (s, 3H), 1.02 (d, 6H).

24 δ 9.80 (br s, 1H), 8.50 (dd, 1H), 7.82 (dd, 1H), 7.42 (s, 1H), 7.39 (m, 1H), 6.50 (br d, 2H), 6.02 (m, 1H), 2.10 (s, 3H), 1.11 (d, 6H).

25 (DMSO-d$_6$): δ 9.77 (s, 1H), 7.67-7.42 (m, 7H), 6.75 (d, 1H), 6.46 (s, 2H), 5.20 (d, 1H), 3.88 (m, 1H), 2.00 (s, 3H), 1.00 (d, 6H).

26 (DMSO-d$_6$): δ 10.01 (s, 1H), 8.39 (s, 1H), 7.84 (d, 1H), 7.70 (s, >1H), 7.6-7.4 (m, >5H), 7.39 (distorted d, 1H), 3.9 (m, 1H), 3.3 (s, 3H), 2.91 (distorted s, 3H), 2.10 (distorted s, 3H), 1.01 (d, 6H).

27 (DMSO-d$_6$): δ 10.00 (s, 1H), 8.63 (s, 1H), 7.89 (d, 1H), 7.70 (s, 1H), 7.63-7.42 (m, >5H), 7.22 (d, J=2.3 Hz, 1H), 5.87 (br s, 2H), 3.91 (m, 1H), 2.10 (s, 3H), 1.01 (d, 6H).

28 δ 9.78 (s, 1H), 8.47 (dd, 1H), 7.85 (m, 1H), 7.63 (s, 1H), 7.40 (dd, 1H), 6.62 (d, 1H), 6.53 (d, 1H), 6.37 (br d, 1H), 4.9 (brs, >2H), 4.05 (m, 1H), 1.07 (d, 6H).

29 (DMSO-d$_6$): δ 9.97 (s, 1H), 8.55 (dd, 1H), 8.20 (dd, 1H), 7.9 (q, <1H), 7.68 (s, 1H), 7.63 (m, 1H), 6.55 (m, 2H), 2.63 (d, 3H), 2.02 (s, 3H).

30 (DMSO-d$_6$): δ 9.96 (s, 1H), 8.52 (dd, 1H), 8.20 (dd, 1H), 7.71 (s, 1H), 7.65 (m, 1H), 7.09 (s, 1H), 6.43 (m, 2H), 5.20 (m, 2H), 1.98 (s, 3H), 1.20 (s, 9H).

33 (DMSO-d$_6$): δ 10.66 (s, 1H), 10.22 (s, 1H), 8.79 (d, 1H), 8.75 (d, 1H), 8.55 (d, 1H), 8.22 (m, 2H), 7.99 (s, 1H), 7.82 (s, 1H), 7.78 (s, 1H), 7.72-7.60 (m, 3H), 3.93 (m, 1H), 2.09 (s, 3H), 1.03 (d, 6H).

$^a$ $^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on apiece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 50 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (20% or less feeding damage): 2, 3, 4, 6, 7, 8, 9, 10, 11, 12, 13, 15, 16, 17, 18, 19, 20, 21, 22, 23, 25, 26, 28, 29, 30, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 and 64.

Test B

For evaluating control of fall armyworm (*Spodoptera frugiperda*) the test unit consisted of a small open container with a 4-5-day-old corn (maize) plant inside. This was pre-infested with 10-15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 2, 3, 4, 6, 7, 8, 9, 10, 11, 12, 14, 15, 16, 18, 19, 20, 21, 22, 23, 24, 25, 26, 27, 28, 29, 30, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 and 64.

Test C

For evaluating control of tobacco budworm (*Heliothis virescens*) the test unit consisted of a small open container with a 6-7 day old cotton plant inside. This was pre-infested with 8 2-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 6, 7, 8, 11, 12, 14, 15, 16, 18, 19, 20, 21, 22, 23, 24, 25, 26, 27, 28, 29, 30, 32, 34, 35, 36, 37, 38, 39, 40, 41, 42, 43, 44, 45, 46 and 48.

Test D

For evaluating control of beet armyworm (*Spodoptera exigua*) the test unit consisted of a small open container with a 4-5-day-old corn plant inside. This was pre-infested with 10-15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 6, 7, 8, 11, 12, 14, 15, 16, 18, 19, 20, 21, 22, 23, 24, 25, 28, 29, 30, 32, 34, 41, 42, 43, 44, 45, 46 and 48.

Test E

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm and replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds tested, the following resulted in at least 80% mortality: 6, 7, 14, 16, 19, 20, 22, 23, 24, 28, 29, 30, 36, 37, 38, 41, 42, 50, 51, 52, 53, 54, 55, 56, 57, 58, 60 and 61.

Test F

For evaluating control of cotton melon aphid (*Aphis gossypii*) through contact and/or systemic means, the test unit consisted of a small open container with a 6-7-day-old cotton plant inside. This was pre-infested with 30-40 aphids on a piece of leaf according to the cut-leaf method described for Test E, and the soil of the test unit was covered with a layer of sand.

Test compounds were formulated and sprayed at 250 ppm as described for Test E. The applications were replicated three times. After spraying, the test units were maintained in a growth chamber and then visually rated as described for Test E.

Of the compounds tested, the following resulted in at least 80% mortality: 19, 20, 24, 36, 37, 38, 39, 40, 42, 50, 51, 54, 56, 57, 58 and 61.

Test G

For evaluating control of Coin Planthopper (*Peregrinus maidis*) through contact and/or systemic means, the test unit consisted of a small open container with a 3-4 day old coin (maize) plant (spike) inside. White sand was added to the top of the soil prior to application. Test compounds were formulated and sprayed at 250 ppm and replicated three times as described for Test E. After spraying, the test units were allowed to dry for 1 hour before they were post-infested with 10-20 Corn Planthoppers (18 to 20 day old nymphs) by sprinkling them onto the sand with a salt shaker. A black, screened cap is placed on the top of the cylinder. The test units were held for 6 days in a growth chamber at 19-21° C. and 50-70% relative humidity. Each test unit was then visually assessed for insect mortality.

Of the compounds tested, the following resulted in at least 80% mortality: 14, 36, 37, 40 and 56.

Test H

For evaluating control of Potato Leafhopper (*Empoasca fabae* Harris) through contact and/or systemic means, the test unit consisted of a small open container with a 5-6 day old Longio bean plant primary leaves emerged) inside. White sand was added to the top of the soil and one of the primary leaves was excised prior to application. Test compounds were formulated and sprayed at 250 ppm and replicated three times as described for Test E. After spraying, the test units were allowed to dry for 1 hour before they were post-infested with 5 Potato Leafhoppers (18 to 21 day old adults). A black, screened cap is placed on the top of the cylinder. The test units were held for. 6 days in a growth chamber at 19-21° C. and 50-70% relative humidity. Each test unit was then visually assessed for insect mortality.

Of the compounds tested, the following resulted in at least 80% mortality: 17, 19, 35, 48, 50, 51, 52, 53, 54, 55, 56, 57, 58 and 59.

What is claimed is:

1. A compound of Formula I, an N-oxide or a salt thereof,

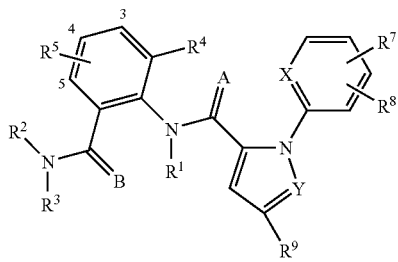

wherein

A and B are independently O or S;

X is $CR^{10}$;

Y is N;

$R^1$ is H; $R^{11}$; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of $R^6$, halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, and $R^{11}$;

$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;

$R^3$ is H; $R^{11}$; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl; $C_2$-$C_6$ alkylcarbonyl; or $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of $R^6$, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_3$-$C_6$ trialkylsilyl, $R^{11}$, a phenyl ring, and a phenoxy ring, each phenyl or phenoxy ring optionally substituted with from one to three substituents independently selected from W and optionally substituted with one $R^{12}$;

$R^4$ is $C_1$-$C_4$ alkyl, $C_1$-$C_4$ haloalkyl, CN, halogen, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, or $C_1$-$C_4$ haloalkylsulfonyl;

$R^5$ and $R^8$ are each independently H; $C_1$-$C_4$ alkyl; halogen; $R^{12}$; G; O-G; $S(O)_p$-G; $S(O)_p$-phenyl optionally substituted with one to three substituents independently selected from W and optionally substituted with one $R^{12}$; $C_1$-$C_{10}$ alkyl, $C_2$-$C_6$ alkenyl, $C_2$-$C_6$ alkynyl, $C_1$-$C_4$ alkoxy or $C_1$-$C_4$ alkythio, each substituted with one or more substituents selected from the group consisting of G, $R^6$, halogen, CN, $NO_2$, $NH_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_2$-$C_6$ alkoxycarbonyl, $C_2$-$C_6$ alkylcarbonyl, $C_3$-$C_6$ trialkylsilyl, a phenyl ring and a phenoxy ring, each phenyl and phenoxy ring optionally substituted with from one to three substituents independently selected from W and optionally substituted with one $R^{12}$;

each G is independently $C_3$-$C_7$ cycloalkyl, $C_3$-$C_7$ halocycloalkyl, $C_3$-$C_7$ cyanocycloalkyl, $C_4$-$C_7$ alkylcycloalkyl, $C_4$-$C_8$ cycloalkylalkyl, or $C_4$-$C_8$ halocycloalkylalkyl;

each $R^6$ is independently $R^{13}C(=E)$-; $R^{14}C(=E)L$-; $R^{13}LC(=E)$-; $(R^{14})LC(=E)L$-; —O(Q=)P($OR^{14}$)$_2$; —$SO_2LR^{13}$; or $R^{14}SO_2L$-;

each E is independently O, S, $NR^{15}$, $NOR^{15}$, $NN(R^{15})_2$, N—S=O, N—CN or N—$NO_2$;

$R^7$ is H, $C_1$-$C_4$ alkyl, $C_1$-$C_4$ haloalkyl, halogen, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, or $C_1$-$C_4$ haloalkylsulfonyl;

$R^9$ is $CF_3$, $OCF_3$, $OCHF_2$, $OCH_2CF_3$, $S(O)_pCF_3$, $S(O)_pCHF_2$ or halogen;

$R^{10}$ is H, $C_1$-$C_4$ alkyl, $C_1$-$C_4$ haloalkyl, halogen, CN or $C_1$-$C_4$ haloalkoxy;

each $R^{11}$ is independently $C_1$-$C_6$ alkylthio; $C_1$-$C_6$ haloalkythio; phenylthio; $SN(R^{16})_2$; $R^{13}C(=O)$—; $R^{14}C(=O)L$-; $R^{13}LC(=O)$—; or $R^{13}LC(=O)NR^{13}S$—;

each L is independently O, $NR^{13}$ or S;

each $R^{12}$ is independently $B(OR^{17})_2$; $NH_2$; SH; thiocyanato; $C_3$-$C_8$ trialkylsilyloxy; $C_1$-$C_4$ alkyldisulfide; $SF_5$; $R^{13}C(=E)$-; $R^{14}C(=E)L$-; $R^{13}LC(=E)$-; $(R^{13})LC(=E)L$-; —OP(=Q)($OR^{14}$)$_2$; —$SO_2LR^{13}$; or $R^{14}SO_2L$-;

Q is O or S;

each $R^{13}$ is independently hydrogen; $C_1$-$C_6$ alkyl, or $C_1$-$C_6$ haloalkyl;

each $R^{14}$ is $C_1$-$C_6$ alkyl, $C_1$-$C_6$ haloalkyl or phenyl optionally substituted with from one to three substituents independently selected from W and optionally substituted with $R^{12}$;

each $R^{15}$ is independently H; $C_1$-$C_6$ haloalkyl; $C_1$-$C_4$ alkyl optionally substituted with one or more substituents selected from the group consisting of CN, $NO_2$, $R^6$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_2$-$C_6$ alkoxycarbonyl, $C_2$-$C_6$ alkylcarbonyl, $C_3$-$C_6$ trialkylsilyl, and a phenyl ring optionally substituted with one to three substituents independently selected from W and optionally substituted with one $R^{12}$; or phenyl optionally substituted with one to three substituents independently selected from W and optionally substituted with $R^{12}$;

each $R^{17}$ is independently H or $C_1$-$C_4$ alkyl;

each W is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$(alkyl)cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; and each p is independently 0, 1 or 2;

provided that when both (a) $R^5$ is H, $C_1$-$C_4$ alkyl, $C_1$-$C_6$ haloalkyl, $C_2$-$C_6$ haloalkenyl, $C_2$-$C_6$ haloalkynyl, $C_1$-$C_4$ haloalkoxy, $C_1$-$C_4$ haloalkylthio, halogen, $C_3$-$C_6$ cycloalkyl, $C_3$-$C_6$ halocycloalkyl or optionally substituted benzyl; and (b) $R^8$ is H, $C_1$-$C_4$ alkyl, $C_1$-$C_6$ haloalkyl, $C_2$-$C_6$ haloalkenyl, $C_2$-$C_6$ haloalkynyl, $C_1$-$C_4$ haloalkoxy, $C_1$-$C_4$ haloalkylthio, halogen, $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl; then both (c) at least one substituent selected from the group consisting of $R^6$, $R^{11}$ and $R^{12}$ is present; and (d) at least one $R^6$ is other than $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl; and/or at least one $R^{11}$ is other than $C_1$-$C_4$ alkylthio, $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl; and/or at least one $R^{12}$, if present, is other than $C_2$-$C_6$ alkylcarbonyl, $C_2$-$C_6$ alkoxycarbonyl, $C_2$-$C_6$ alkylamioncarbonyl or $C_3$-$C_8$ dialkylaminocarbonyl.

2. A compound of claim 1 wherein

A and B are both O.

3. A compound of claim 2 wherein one substituent selected from the group consisting of $R^6$, $R^{11}$ and $R^{12}$ is present.

4. A compound of claim 3 with the Formula Is

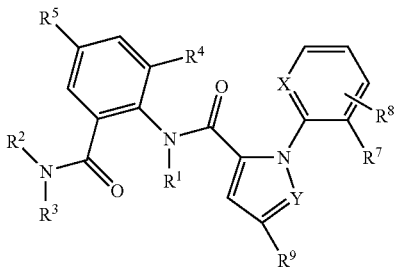

wherein
- $R^1$ is H; or $R^{11}$;
- $R^2$ is $C_1$-$C_6$ alkyl;
- $R^3$ is H; or $R^{11}$;
- $R^4$ is $C_1$-$C_4$ alkyl or halogen;
- $R^5$ is H, $C_1$-$C_4$ alkyl, $C_1$-$C_4$ haloalkyl or halogen;
- $R^7$ is $C_1$-$C_4$ haloalkyl or halogen;
- $R^8$ is H;
- $R^9$ is $CF_3$, $OCF_3$, $OCHF_2$, $OCH_2CF_3$, $S(O)_pCF_3$, $S(O)_pCHF_2$ or halogen;
- L is $NR^{13}$ or S;
- each $R^{13}$ is independently hydrogen; $C_1$-$C_6$ alkyl, $C_1$-$C_6$ haloalkyl;
- each $R^{14}$ is $C_1$-$C_6$ alkyl, $C_1$-$C_6$ haloalkyl or phenyl optionally substituted with one to three substituents independently selected from W; and
- $R^{16}$ is $C_1$-$C_4$ alkyl or $C_1$-$C_4$ haloalkyl;
- provided that one $R^{11}$ is present.

5. A compound of claim 4 wherein
- $R^4$ is $CH_3$, F, Cl or Br;
- $R^5$ is H, $CF_3$, F, Cl, Br or I;
- $R^7$ is Cl or Br;
- $R^9$ is $CF_3$, $OCHF_2$, $OCH_2CF_3$, Cl or Br; and
- $R^{10}$ is H.

6. A compound of claim 3 wherein
- $R^1$ is H;
- $R^2$ is H or $C_1$-$C_6$ alkyl;
- $R^3$ is $C_1$-$C_6$ alkyl;
- $R^5$ is $C_1$-$C_{10}$ alkyl substituted with one substituent selected from the group consisting of CN, $NO_2$, $NH_2$, hydroxy and $R^6$; or $R^{12}$;
- $R^6$ is $R^{13}C(=E)-$; $R^{14}C(=E)L-$; $R^{13}LC(=E)-$; or $(R^{14})LC(=E)L-$;
- $R^{12}$ is $NH_2$; $R^{13}C(=E)-$; $R^{14}C(=E)L-$; $R^{13}LC(=E)-$; or $(R^{13})LC(=E)L-$;
- each E is independently O or $NOR^{15}$;
- each L is independently O or $NR^{13}$; and
- each $R^{15}$ is independently H or $C_1$-$C_4$ alkyl.

7. A compound of claim 6 wherein
- $R^5$ is $R^{12}$;
- $R^{12}$ is $R^{14}C(=O)L-$ or $(R^{13})LC(=O)L-$; and
- each L is independently $NR^{13}$.

8. A compound of claim 6 wherein
- $R^5$ is $C_1$-$C_{10}$ alkyl substituted with hydroxy; or $R^{12}$;
- $R^{12}$ is $R^{13}C(=E)-$ or $R^{13}LC(=O)-$;
- E is O or $NOR^{15}$;
- L is O or $NR^{13}$; and
- $R^{15}$ is H or $C_1$-$C_4$ alkyl.

9. A compound of claim 3 wherein
- $R^1$ is H;
- $R^2$ is H or $C_1$-$C_6$ alkyl;
- $R^3$ is $C_1$-$C_6$ alkyl;
- $R^5$ is H, $C_1$-$C_4$ haloalkyl or halogen;
- $R^8$ is $C_1$-$C_{10}$ alkyl substituted with one substituent selected from the group consisting of CN, $NO_2$, $NH_2$, hydroxy and $R^6$; or $R^{12}$;
- $R^6$ is $R^{13}C(=E)-$; $R^{14}C(=E)L-$; $R^{13}LC(=E)-$; or $(R^{14})LC(=E)L-$;
- $R^{12}$ is $R^{13}C(=E^1)-$; $R^{14}C(=E^2)L-$; $R^{13}LC(=E^1)-$ or $(R^{13})LC(=E^2)L-$;
- each E is independently O or $NOR^{15}$;
- each $E^1$ is $NOR^{15}$;
- each $E^2$ is independently O or $NOR^{15}$;
- each L is independently O or $NR^{13}$; and
- each $R^{15}$ is independently H or $C_1$-$C_4$ alkyl.

10. A compound of claim 9 wherein
- $R^8$ is $C_1$-$C_{10}$ alkyl substituted with one substituent selected from the group consisting of $NH_2$, hydroxy and $R^6$; or $R^{12}$;
- $R^6$ is $R^{14}C(=O)L-$;
- $R^{12}$ is $R^{13}LC(=E^1)-$; and
- each L is independently $NR^{13}$.

11. The compound of claim 10 that is selected from the group consisting of
- 1-[2-(Aminomethyl)phenyl]-N-[2-methyl-6-[[(1-methylethyl)amino]carbonyl]phenyl]-3-(trifluoromethyl)-1H-pyrazole-5-carboxamide,
- 1-[2-[[(trifluoroacetyl)amino]methyl]phenyl]-N-[2-methyl-6-[[(1-methylethyl)amino]carbonyl]phenyl]-3-(trifluoromethyl)-1H-pyrazole-5-carboxamide and
- 1-[2-(hydroxymethyl)phenyl]-N-(2-methyl-6-[[(1-methylethyl)amino]carbonyl]phenyl]-3-(trifluoromethyl)-1H-pyrazole-5-carboxamide.

12. A compound of claim 3 wherein
- $R^1$ is H;
- $R^2$ is H or $C_1$-$C_6$ alkyl;
- $R^3$ is $C_1$-$C_6$ alkyl substituted with one $R^6$;
- $R^4$ is $C_1$-$C_4$ alkyl or halogen;
- $R^5$ is H, $C_1$-$C_4$ haloalkyl or halogen;
- $R^6$ is $R^{13}C(=E^1)-$; $R^{14}C(=E^2)L-$; $R^{13}LC(=E^1)-$ or $(R^{14})LC(=E^2)L-$;
- each $E^1$ is independently S, $NR^{15}$, $NOR^{15}$, or $NN(R^{15})_2$;
- each $E^2$ is independently O, S, $NR^{15}$, $NOR^{15}$, or $NN(R^{15})_2$;
- each L is independently O or $NR^{13}$;
- $R^7$ is $C_1$-$C_4$ haloalkyl or halogen;
- $R^8$ is H;
- $R^9$ is $CF_3$, $OCF_3$, $OCHF_2$, $OCH_2CF_3$, $S(O)_pCF_3$, $S(O)_pCHF_2$ or halogen;
- each $R^{15}$ is independently H; $C_1$-$C_6$ haloalkyl; $C_1$-$C_4$ alkyl optionally substituted with one substituent selected from the group consisting of CN, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl and $C_1$-$C_4$ haloalkylsulfonyl; and
- each p is independently 0, 1 or 2.

13. A compound of claim 12 wherein
- $R^3$ is $C_1$-$C_6$ alkyl substituted with one $R^6$;
- $R^6$ is $R^{13}C(=E^1)-$; and
- $E^1$ is $NOR^{15}$.

14. A compound of claim 1 wherein $R^5$ is $NH_2$.

15. A method for controlling an invertebrate pest comprising: contacting the invertebrate pest or its environment with a biologically effective amount of a compound of claim 1, an N-oxide thereof or a salt thereof.

16. A composition for controlling an invertebrate pest comprising: a biologically effective amount of a compound of claim 1; and at least one additional component selected from the group consisting of surfactants, solid diluents and liquid diluents.

17. A compound of Formula Is that is selected from the group consisting of:

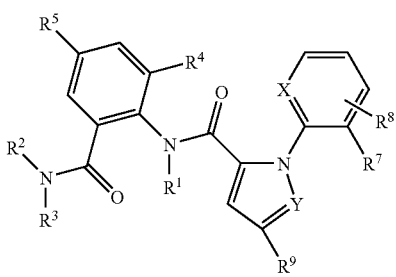

Is the compound wherein X is CH, Y is N, $R^1$ is H, $R^2$ is $CH(Me)_2$, $R^3$ is H, $R^4$ is Me, $R^5$ is $NH_2$, $R^7$ is Cl, $R^8$ is H and $R^9$ is $CF_3$;

the compound wherein X is CH, Y is N, $R^1$ is H, $R^2$ is $CH(Me)_2$, $R^3$ is H, $R^4$ is Me, $R^5$ is $NH_2CONMe_2$, $R^7$ is Cl, $R^8$ is H and $R^9$ is $CF_3$; and the compound wherein X is CH, Y is N, $R^1$ is H, $R^2$ is $CH(Me)_2$, $R^3$ is H, $R^4$ is Me, $R^5$ is $NH_2CONH_2$, $R^7$ is Cl, $R^8$ is H and $R^9$ is $CF_3$.

* * * * *

UNITED STATES PATENT AND TRADEMARK OFFICE
CERTIFICATE OF CORRECTION

| | | |
|---|---|---|
| PATENT NO. | : 7,541,377 B2 | |
| APPLICATION NO. | : 11/700584 | |
| DATED | : June 2, 2009 | |
| INVENTOR(S) | : Bruce Lawrence Finkelstein et al. | |

It is certified that error appears in the above-identified patent and that said Letters Patent is hereby corrected as shown below:

Column 51, second heading "$R^3$ is Me, $R^4$ is M; X is N, $R^7$ is Cl, $R^9$ is $CF_3$ and $R^5$ is selected from" should read -- $R^3$ is Me, $R^4$ is Me; X is N, $R^7$ is Cl, $R^9$ is $CF_3$ and $R^5$ is selected from --

Column 55, under the first heading, 4$^{th}$ column, 9$^{th}$ line "$OCH_2CH=O(Cl)_2$" should read -- $OCH_2CH=C(Cl)_2$ --

Column 73, second heading "$R^3$ is Me, $R^4$ is Me, X is N, $R^7$ is Cl, $R^9$ is Br, $R^5$ is Cl and H1 is selected from" should read -- $R^3$ is Me, $R^4$ is Me, X is N, $R^7$ is Cl, $R^9$ is Br, $R^5$ is Cl and R1 is selected from --

Column 79, second heading "$R^4$ is Cl, X is CH2 $R^5$ is Cl, P2 is $CF_3$, $R^7$ is Cl, and $R^3$ is selected from" should read -- $R^4$ is Cl, X is CH, $R^5$ is Cl, $R^9$ is $CF_3$, $R^7$ is Cl, and $R^3$ is selected from --

The unit "°C." should be replaced with "°C" in all the following places:

Column 31, line 66

Column 35, lines 49, 50, 52

Column 37, line 42

Column 38, lines 58, 59

Column 39, line 34

Column 41, lines 17, 21

Column 45, line 31

Column 46, lines 21, 34, 41, 43, 59

Signed and Sealed this
Seventh Day of August, 2012

David J. Kappos
*Director of the United States Patent and Trademark Office*

The unit ""°C."" should be replaced with ""°C"" in all the following places:

Column 47, lines 12, 32, 60

Column 48, lines 12, 13, 43 (2 places), 64

Column 49, lines 18, 33, 34, 40, 57, 63

Column 50, lines 12, 13, 39

Column 96, line 54

Column 98, lines 3, 42, 62